United States Patent
Dobbles et al.

(10) Patent No.: US 9,452,259 B2
(45) Date of Patent: Sep. 27, 2016

(54) INTEGRATED INSULIN DELIVERY SYSTEM WITH CONTINUOUS GLUCOSE SENSOR

(71) Applicant: DexCom, Inc., San Diego, CA (US)

(72) Inventors: John Michael Dobbles, San Clemente, CA (US); Apurv Ullas Kamath, San Diego, CA (US); Aarthi Mahalingam, San Diego, CA (US); James H. Brauker, Addison, MI (US)

(73) Assignee: DexCom, Inc., San Diego, CA (US)

( * ) Notice: Subject to any disclaimer, the term of this patent is extended or adjusted under 35 U.S.C. 154(b) by 523 days.

(21) Appl. No.: 14/063,941

(22) Filed: Oct. 25, 2013

(65) Prior Publication Data

US 2014/0052095 A1 Feb. 20, 2014

Related U.S. Application Data

(63) Continuation of application No. 13/885,604, filed as application No. PCT/US2007/080848 on Oct. 9, 2007.

(51) Int. Cl.
*A61M 5/172* (2006.01)
*A61B 5/145* (2006.01)
*A61M 5/142* (2006.01)
(Continued)

(52) U.S. Cl.
CPC ........ *A61M 5/1723* (2013.01); *A61B 5/14532* (2013.01); *A61B 5/14546* (2013.01); *A61M 5/14244* (2013.01); *G06F 19/3468* (2013.01); *A61B 5/0031* (2013.01); *A61M 5/003* (2013.01); *A61M 5/178* (2013.01); *A61M 5/30* (2013.01); *A61M 11/00* (2013.01); *A61M 15/00* (2013.01); *A61M 2005/14296* (2013.01); *A61M 2230/201* (2013.01)

(58) Field of Classification Search
CPC ........ A61M 5/1723; A61M 5/14244; A61M 2230/201; A61M 2005/14296; A61M 5/003; A61M 5/178; A61M 15/00; A61M 11/00; A61M 5/30; G06F 19/3468; A61B 5/14546; A61B 5/14532; A61B 5/0031
USPC .............. 604/65–67, 131, 151; 128/DIG. 12, 128/DIG. 13; 600/316, 365, 300
See application file for complete search history.

(56) References Cited

U.S. PATENT DOCUMENTS

| 4,703,756 A | 11/1987 | Gough et al. |
|---|---|---|
| 5,019,974 A | 5/1991 | Beckers |

(Continued)

FOREIGN PATENT DOCUMENTS

| EP | 1338295 A1 | 8/2003 |
|---|---|---|
| WO | WO 03/022327 | 3/2003 |

(Continued)

OTHER PUBLICATIONS

Diabetes Care 30(Supp. 1):S3 (Jan. 2007): Summary of Revisions for the 2007 Clinical Practice Recommendations.
(Continued)

*Primary Examiner* — Manuel Mendez
(74) *Attorney, Agent, or Firm* — Knobbe Martens Olson & Bear, LLP

(57) ABSTRACT

Systems and methods for integrating a continuous glucose sensor 12, including a receiver 14, a medicament delivery device 16, a controller module, and optionally a single point glucose monitor 18 are provided. Integration may be manual, semi-automated and/or fully automated.

19 Claims, 16 Drawing Sheets

(51) Int. Cl.

| | |
|---|---|
| G06F 19/00 | (2011.01) |
| A61B 5/00 | (2006.01) |
| A61M 5/00 | (2006.01) |
| A61M 5/178 | (2006.01) |
| A61M 5/30 | (2006.01) |
| A61M 11/00 | (2006.01) |
| A61M 15/00 | (2006.01) |

(56) References Cited

U.S. PATENT DOCUMENTS

| | | | |
|---|---|---|---|
| 5,101,814 | A | 4/1992 | Palti |
| 5,429,602 | A | 7/1995 | Hauser |
| 5,474,552 | A | 12/1995 | Palti |
| 5,569,186 | A | 10/1996 | Lord et al. |
| 5,660,565 | A | 8/1997 | Williams |
| 5,665,065 | A | 9/1997 | Colman et al. |
| 5,674,289 | A | 10/1997 | Fourner et al. |
| 5,733,259 | A * | 3/1998 | Valcke ............ A61M 5/1723 128/DIG. 12 |
| 5,919,216 | A | 7/1999 | Houben et al. |
| 5,925,021 | A | 7/1999 | Castellano et al. |
| 6,135,978 | A | 10/2000 | Houben et al. |
| 6,163,720 | A | 12/2000 | Gyory et al. |
| 6,175,752 | B1 | 1/2001 | Say et al. |
| 6,234,964 | B1 | 5/2001 | Iliff |
| 6,248,067 | B1 | 6/2001 | Causey et al. |
| 6,302,855 | B1 | 10/2001 | Lav et al. |
| 6,312,388 | B1 | 11/2001 | Marcovecchio et al. |
| 6,424,847 | B1 | 7/2002 | Mastrototaro et al. |
| 6,477,395 | B2 | 11/2002 | Schulman et al. |
| 6,512,939 | B1 | 1/2003 | Colvin et al. |
| 6,544,212 | B2 | 4/2003 | Galley et al. |
| 6,549,796 | B2 | 4/2003 | Schrab |
| 6,558,320 | B1 | 5/2003 | Causey et al. |
| 6,558,351 | B1 | 5/2003 | Steil et al. |
| 6,558,955 | B1 | 5/2003 | Kristal et al. |
| 6,562,001 | B2 | 5/2003 | Lebel et al. |
| 6,565,509 | B1 | 5/2003 | Say et al. |
| 6,571,128 | B2 | 5/2003 | Lebel et al. |
| 6,572,545 | B2 * | 6/2003 | Knobbe ............ A61B 5/0002 600/300 |
| 6,577,899 | B2 | 6/2003 | Lebel et al. |
| 6,620,138 | B1 | 9/2003 | Marrgi et al. |
| 6,635,014 | B2 | 10/2003 | Starkweather et al. |
| 6,648,821 | B2 | 11/2003 | Lebel et al. |
| 6,740,072 | B2 | 5/2004 | Starkweather et al. |
| 6,750,055 | B1 | 6/2004 | Connelly et al. |
| 6,832,200 | B2 | 12/2004 | Greeven et al. |
| 6,875,195 | B2 | 4/2005 | Choi |
| 6,936,029 | B2 | 8/2005 | Mann et al. |
| 7,025,743 | B2 | 4/2006 | Mann et al. |
| 7,060,059 | B2 | 6/2006 | Keith et al. |
| 7,267,665 | B2 | 9/2007 | Steil et al. |
| 7,278,983 | B2 | 10/2007 | Ireland et al. |
| 7,282,029 | B1 | 10/2007 | Poulsen et al. |
| 7,344,500 | B2 | 3/2008 | Talbot et al. |
| 7,519,408 | B2 | 4/2009 | Rasdal et al. |
| 7,569,030 | B2 | 8/2009 | Lebel et al. |
| 7,591,801 | B2 | 9/2009 | Brauker et al. |
| 7,647,237 | B2 | 1/2010 | Malave et al. |
| 7,670,288 | B2 * | 3/2010 | Sher ............... A61B 5/14532 600/345 |
| 7,901,394 | B2 | 3/2011 | Ireland et al. |
| 7,946,985 | B2 | 5/2011 | Mastrototaro et al. |
| 8,512,276 | B2 | 8/2013 | Talbot et al. |
| 2002/0045808 | A1 | 4/2002 | Ford et al. |
| 2002/0065453 | A1 | 5/2002 | Lesho et al. |
| 2003/0028089 | A1 | 2/2003 | Galley |
| 2003/0060692 | A1 | 3/2003 | Ruchti et al. |
| 2003/0060753 | A1 | 3/2003 | Starkweather et al. |
| 2003/0114836 | A1 | 6/2003 | Estes et al. |
| 2003/0187338 | A1 | 10/2003 | Say et al. |
| 2003/0208113 | A1 | 11/2003 | Mault et al. |
| 2004/0044272 | A1 | 3/2004 | Moerman et al. |
| 2004/0122353 | A1 * | 6/2004 | Shahmirian ...... A61M 5/14276 604/65 |
| 2004/0162678 | A1 | 8/2004 | Hetzel et al. |
| 2005/0027462 | A1 | 2/2005 | Goode et al. |
| 2005/0113653 | A1 | 5/2005 | Fox et al. |
| 2005/0203360 | A1 | 9/2005 | Brauker et al. |
| 2005/0245904 | A1 | 11/2005 | Estes et al. |
| 2006/0173406 | A1 * | 8/2006 | Hayes ............... A61B 5/14532 604/67 |
| 2007/0032706 | A1 * | 2/2007 | Kamath ............ A61B 5/14532 600/300 |
| 2007/0066956 | A1 | 3/2007 | Finkel |
| 2007/0100222 | A1 | 5/2007 | Mastrototaro et al. |
| 2007/0106135 | A1 | 5/2007 | Sloan et al. |
| 2007/0112298 | A1 | 5/2007 | Mueller et al. |
| 2007/0173761 | A1 | 7/2007 | Kanderian et al. |
| 2007/0179434 | A1 | 8/2007 | Weinert et al. |
| 2007/0293742 | A1 | 12/2007 | Simonsen et al. |
| 2008/0097289 | A1 | 4/2008 | Steil et al. |
| 2008/0269723 | A1 | 10/2008 | Mastrototaro et al. |
| 2012/0227737 | A1 | 9/2012 | Mastrototaro et al. |
| 2012/0259278 | A1 | 10/2012 | Hayes et al. |

FOREIGN PATENT DOCUMENTS

| | | |
|---|---|---|
| WO | WO 2004/009161 | 1/2004 |
| WO | WO 2006-021430 | 3/2006 |

OTHER PUBLICATIONS

American Diabetes Association, Diabetes Care 30(Supp. 1):S3 (Jan. 2007): Summary of Revisions for the 2007 Clinical Practice Recommendations.

American Diabetes Association, Diabetes Care 30(Supp. 1):S4 (Jan. 2007): Standards of Medical Care in Diabetes—2007.

American Diabetes Association, Diabetes Care 30(Suppl. 1):S42 (Jan. 2007): Diagnosis and Classification of Diabetes Mellitus.

Aussedat et al., Am. J. Physiol. Endocrinol. Metab. 278:E716-E728 (2000): Interstitial Glucose Concentration and Glycemia: Implications for Continuous Subcutaneous Glucose Monitoring.

Chase et al., Diabetes Technology & Therapeutics 7:274 (Nov. 2, 2005): Targeted Glycemic Reduction in Critical Care Using Closed-Loop Control.

El-Khatib et al., J. Diabetes Sci. & Technology 1(2):181 (Mar. 2007): Adaptive Closed-Loop Control Provides Blood-Glucose Regulation Using Dual Subcutaneous Insulin and Glucagon Infusion in Diabetic Swine.

Frohnauer et al., Diabetes Technology & Therapeutics 3(3):419 (2001): Graphical Human Insulin Time-Activity Profiles Using Standardized Definitions.

Garg et al . Diabetes Care 27(3):734 (Mar. 2004): Improved Glucose Excursions Using an Implantable Real-Time Continuous Glucose Sensor in Adults with Type 1 Diabetes.

Garg, Satish K., Diabetes Technology & Therapeutics 7(5):813 (2005): New Insulin Analogues.

Hagvik, Joakim, J. Diabetes Sci. & Technology 1(2):169 (Mar. 2007): Glucose Measurement: Time for a Gold Standard.

Heinemann et al., Diabetes Technology & Therapeutics 6(5):698 (2004): (Review) Measurement of Insulin Absorption and Insulin Action.

Heinemann, Lutz, Diabetes Technology & Therapeutics 4(5):2002): (Review) Variability of Insulin Absorption and Insulin Action.

Heinemann, Lutz, J. Diabetes Sci. & Technology 1(2):178 (Mar. 2007): Measurement Quality of Blood Glucose Meters: Is There A Need for an Institution with an Unbiased View?

Hovorka et al., Diabetes Technology & Therapeutics 6(3):307 (2004): Closing the Loop: The Adicol Experience.

Hunsley et al., J. Diabetes Sci. & Technology 1(2):173 (Mar. 2007): Whole Blood Glucose Standard is Key to Accurate Insulin Dosages.

Jones et al., Diabetes Technology & Therapeutics 7(2):233 (2005): Optimal Insulin Pump Dosing and Postprandial Glycemia Following a Pizza Meal Using the Continuous Glucose Monitoring System.

Kizilel et al., Diabetes Technology & Therapeutics 7(6):968 (2005): (Review) The Bioartificial Pancreas: Progress and Challenges.

(56) References Cited

OTHER PUBLICATIONS

Klonoff, David C., Diabetes Technology & Therpeutics 4(5):582 (2002): (Editorial) Current, Emerging, and Future Trends in Metabolic Monitoring.

Koschinsky et al., Diabetes Technology & Therapeutics 5(5):829 (2003): (Review) Glucose Sensors and the Alternate Site Testing-Like Phenomenon: Relationship Between Rapid Blood Glucose Changes and Glucose Sensor Signals.

Lee et al., J. Diabetes Sci. & Technology 1(3):400 (May 2007): Combined Insulin Pump Therapy with Real-Time Continuous Glucose Monitoring Significantly Improves Glycemic Control Compared to Multiple Daily Injection Therapy.

Ristic et al., Diabetes Technology & Therapeutics 5(1):57 (2003): (Review) Effects of Rapid-Acting Insulin Analogs on Overall Glycemic Control in Type 1 and Type 2 Diabetes Mellitus.

Thennadil et al., Diabetes Technology & Therapeutics 3(3):357 (2001): Comparison to Glucose Concentration in Interstitial Fluid, and Capillary and Venous Blood During Rapid Changes in Blood Glucose Levels.

Vesper et al., Diabetes Technology & Therapeutics 8(1):76 (2006): Assessment of Trueness of a Glucose Monitor Using Interstitial Fluid and Whole Blood as Specimen Matrix.

Wenthoit et al., Diabetes Technology & Therapeutics 9(2):169 (2007): Relationship Between Interstitial and Blood Glucose in Type 1 Diabetes Patients: Delay and the Push-Pull Phenomenon Revisited.

Wolpert, Howard A., Diabetes Technology & Therapeutics 5(5):843 (2003): (Commentary) A Clinicians Perspective on Some of the Challenges in "Closed Loop".

NewsRx (Aug. 3, 2003). Medical Letter on the CDC & FDA via NewsRx.com. "Glucose Monitoring: FDA OKs new device to manage diabetes".

Renard, Eric (2002), Current Opinion in Pharmacology 2:708-716. Implantable closed-loop glucose sensing and insulin delivery: the future for insulin pump therapy.

* cited by examiner

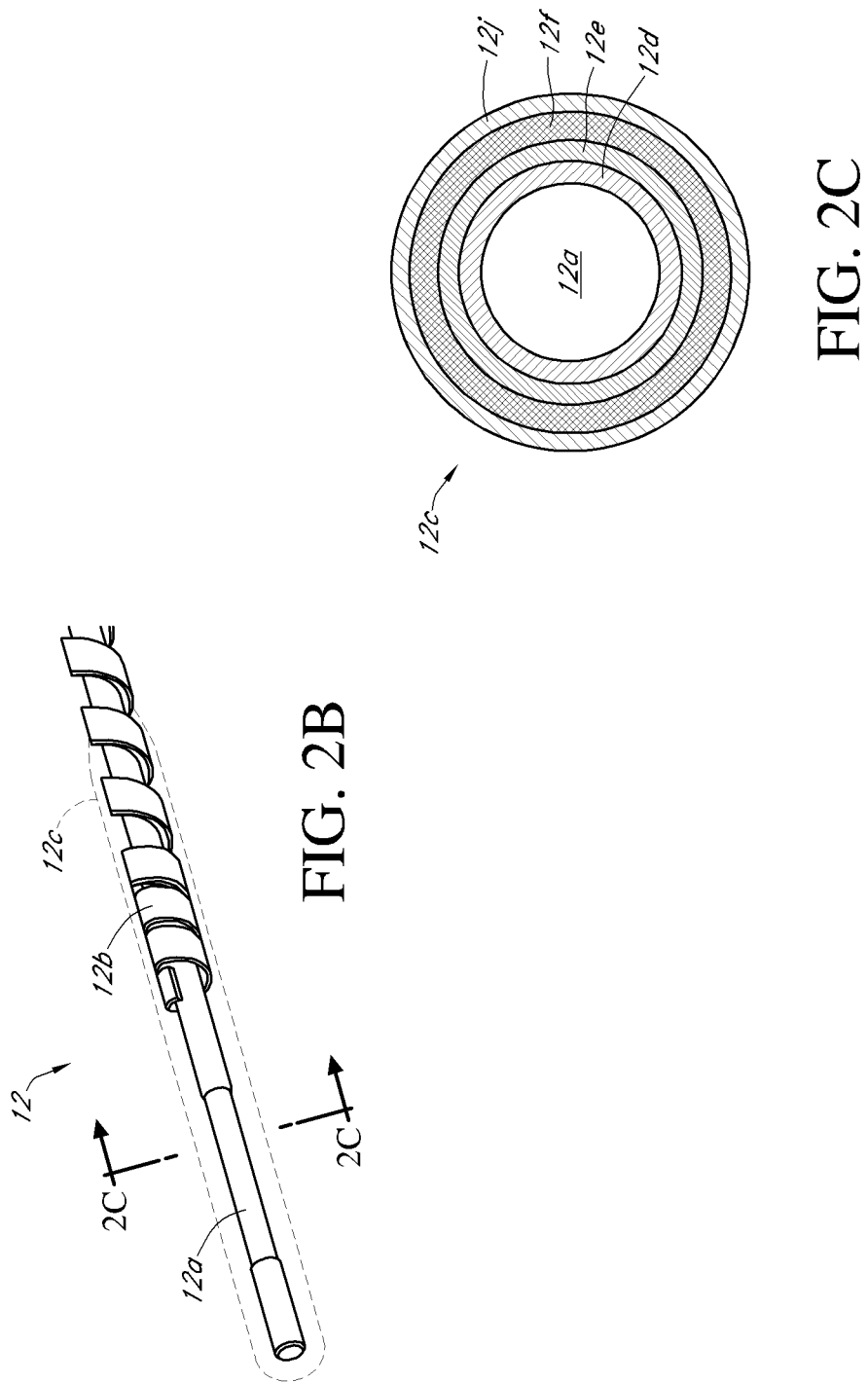

INTEGRATED INSULIN DELIVERY SYSTEM WITH CONTINUOUS GLUCOSE SENSOR

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 13/885,604, filed on May 15, 2013, which is the national phase under 35 U.S.C. §371 of prior PCT International Application No. PCT/US2007/080848 filed on Oct. 9, 2007. Each of the aforementioned applications is incorporated by reference herein in its entirety, and each is hereby expressly made a part of this specification.

FIELD OF THE INVENTION

The present invention relates generally to systems and methods monitoring glucose in a host. More particularly, the present invention relates to an integrated medicament delivery device and continuous glucose sensor.

BACKGROUND OF THE INVENTION

Diabetes mellitus is a disorder in which the pancreas cannot create sufficient insulin (Type I or insulin dependent) and/or in which insulin is not effective (Type 2 or non-insulin dependent). In the diabetic state, the victim suffers from high glucose, which may cause an array of physiological derangements (for example, kidney failure, skin ulcers, or bleeding into the vitreous of the eye) associated with the deterioration of small blood vessels. A hypoglycemic reaction (low glucose) may be induced by an inadvertent overdose of insulin, or after a normal dose of insulin or glucose-lowering agent accompanied by extraordinary exercise or insufficient food intake.

Conventionally, a diabetic person carries a self-monitoring blood glucose (SMBG) monitor, which typically comprises uncomfortable finger pricking methods. Due to the lack of comfort and convenience, a diabetic generally measures his glucose level only two to four times per day. Unfortunately, these time intervals are spread so far apart that the diabetic will likely find out too late that he has entered a hyper- or hypo-glycemic condition, sometimes incurring dangerous side effects. In fact, it is not only unlikely that a diabetic will take a timely SMBG value, but he will not know if his blood glucose is going up (higher) or down (lower), which inhibits his ability to make educated insulin therapy decisions.

Home diabetes therapy requires personal discipline of the user, appropriate education from a doctor, proactive behavior under sometimes-adverse situations, patient calculations to determine appropriate therapy decisions, including types and amounts of administration of insulin and glucose into his or her system, and is subject to human error. Technologies are needed that ease the burdens faced by diabetic patients, simplify the processes involved in treating the disease, and minimize user error which may cause unnecessarily dangerous situations in some circumstances.

SUMMARY OF THE INVENTION

In a first aspect, an integrated system for monitoring a glucose concentration in a host and for delivering insulin to a host is provided, the system comprising a continuous glucose sensor, wherein the continuous glucose sensor is configured to substantially continuously measure a glucose concentration in a host, and to provide sensor data associated with the glucose concentration in the host; an electronics module comprising an on/off controller module configured to iteratively determine an insulin therapy instruction in response to an evaluation of a relationship of internally derived data and a glucose boundary, wherein the insulin therapy instruction comprises an instruction selected from the group consisting of on and off; and an insulin delivery device configured to deliver insulin to the host, wherein the insulin delivery device is at least one of physically connected to a receiver and operably connected to a receiver, wherein the insulin delivery device is configured to receive the insulin therapy instruction from the controller.

In an embodiment of the first aspect, the insulin therapy instruction is determined solely on internally derived data and the glucose boundary.

In an embodiment of the first aspect, the glucose boundary is programmable by at least one of the host, a caretaker of the host, the on/off controller module, and a manufacturer of the integrated system.

In an embodiment of the first aspect, the glucose boundary is a glucose concentration of from about 70 mg/dl to about 160 mg/dl.

In an embodiment of the first aspect, an on insulin therapy instruction is determined when the glucose concentration exceeds the glucose boundary.

In an embodiment of the first aspect, the insulin delivery device is configured to deliver insulin automatically in response to selection of the on insulin therapy instruction.

In an embodiment of the first aspect, the insulin is flash insulin.

In an embodiment of the first aspect, the insulin delivery device is further configured to deliver insulin at a programmable delivery rate, wherein the delivery rate is programmable by at least one of the host, a caretaker of the host, the on/off controller module, and a manufacturer of the system.

In an embodiment of the first aspect, the insulin delivery device is further configured to deliver insulin at a programmed delivery rate and wherein the on/off controller module is configured to iteratively determine the insulin therapy instruction in response to internally derived data and the glucose boundary, wherein the on/off controller module comprises programming configured to adjust an insulin delivery rate in response to internally derived data and the glucose boundary.

In an embodiment of the first aspect, the on/off controller module is further configured to iteratively determine the insulin therapy instruction in response to a host's metabolic response to an insulin therapy, wherein the on/off controller module comprises programming configured to adjust an insulin delivery rate in response to the host's metabolic response.

In an embodiment of the first aspect, the off insulin therapy instruction is selected when the glucose concentration falls below the glucose boundary.

In an embodiment of the first aspect, the insulin delivery device is configured to automatically terminate insulin delivery in response to selection of the off insulin therapy instruction.

In an embodiment of the first aspect, the insulin delivery device is configured to provide delivery device data associated with insulin delivery.

In an embodiment of the first aspect, the internally derived data comprises at least one of sensor data, processed sensor data, delivery device data, and processed delivery device data.

The integrated system of Claim 14, wherein the internally derived data further comprises at least one of a glucose concentration, a glucose concentration range, a change in glucose concentration, a glucose concentration rate of change, an acceleration of a glucose concentration rate of change, a host insulin sensitivity, a change in host insulin sensitivity, a host metabolic response to insulin therapy, an amount of insulin delivered, a time of insulin delivery, an insulin on board, and a time.

In an embodiment of the first aspect, the integrated system further comprises an auxiliary sensor configured to provide auxiliary sensor data associated with at least one measurement made by the auxiliary sensor in the host, wherein the internally derived data further comprises auxiliary sensor data.

In an embodiment of the first aspect, the auxiliary sensor comprises at least one of an accelerometer, a pressure sensor, a pH sensor, a temperature sensor, an oxygen sensor, an auxiliary glucose sensor, an analyte sensor configured to measure an analyte other than glucose, a proximity sensor, and an orientation sensor.

In a second aspect, an integrated system for monitoring a glucose concentration in a host and for delivering insulin to a host is provided, the system comprising a continuous glucose sensor, wherein the continuous glucose sensor is configured to substantially continuously measure a glucose concentration in a host, and to provide sensor data associated with a glucose concentration of the host; an electronics module comprising a basal controller module configured to iteratively determine an insulin therapy instruction in response to an evaluation of a relationship of internally derived data and a basal profile, wherein the basal profile comprises at least one time block associated with a maximum insulin delivery rate; and an insulin delivery device configured to deliver insulin to the host, wherein the insulin delivery device is at least one of physically connected to a receiver and operably connected to a receiver, wherein the insulin delivery device is configured to receive the insulin therapy instruction from the controller module, wherein the insulin therapy instruction is constrained by a maximum insulin delivery rate associated with a current time block.

In an embodiment of the second aspect, the insulin therapy instruction is determined solely on internally derived data and the basal profile.

In an embodiment of the second aspect, the maximum insulin delivery rate is an insulin delivery rate of from about 0.01 U/hour to about 6.0 U/hour.

In an embodiment of the second aspect, the insulin delivery device is configured to deliver insulin automatically in response to receiving the insulin therapy instruction.

In an embodiment of the second aspect, the insulin therapy instruction instructs delivery of insulin at less than the maximum insulin delivery rate associated with the current time block.

In an embodiment of the second aspect, the basal profile is programmable by at least one of the host and a caretaker of the host.

In an embodiment of the second aspect, the basal profile is programmable by at least one of the basal controller module and a manufacturer of the integrated system.

In an embodiment of the second aspect, the basal controller module is configured to iteratively determine the insulin therapy instruction in response to internally derived data and the basal profile, wherein the basal controller module comprises programming to adjust the basal profile in response to internally derived data.

In an embodiment of the second aspect, the basal controller module is further configured to iteratively determine the insulin therapy instruction in response to a host's metabolic response to an insulin therapy, wherein the basal controller module comprises programming to adjust the basal profile in response to the host's metabolic response.

In an embodiment of the second aspect, the insulin delivery device is configured to provide delivery device data associated with insulin delivery.

In an embodiment of the second aspect, the internally derived data comprises at least one of sensor data, processed sensor data, delivery device data, and processed delivery device data.

In an embodiment of the second aspect, the internally derived data further comprises at least one of a glucose concentration, a glucose concentration range, a change in glucose concentration, a glucose concentration rate of change, an acceleration of the glucose concentration rate of change, a host insulin sensitivity, a change in host insulin sensitivity, a host metabolic response to insulin therapy, an amount of insulin delivered, a time of insulin delivery, an insulin on board, and a time.

In an embodiment of the second aspect, the integrated system further comprises an auxiliary sensor configured to provide auxiliary sensor data associated with at least one measurement made by the auxiliary sensor in the host, wherein the internally derived data further comprises auxiliary sensor data.

In an embodiment of the second aspect, the auxiliary sensor comprises at least one of an accelerometer, a pressure sensor, a pH sensor, a temperature sensor, an oxygen sensor, an auxiliary glucose sensor, an analyte sensor configured to measure an analyte other than glucose, a proximity sensor, and an orientation sensor.

In a third embodiment, an integrated system for monitoring a glucose concentration in a host and for delivering insulin to a host is provided, the system comprising a continuous glucose sensor, wherein the continuous glucose sensor is configured to substantially continuously measure a glucose concentration in a host, and to provide sensor data associated with the glucose concentration of the host; an electronics module comprising a bolus controller module configured to iteratively determine an insulin therapy instruction in response to an evaluation of a relationship of internally derived data and an engageable bolus constraint, wherein a relationship of internally derived data to the bolus constraint is evaluated in response to engagement of the bolus constraint, and wherein the bolus constraint comprises a maximum total insulin dose that can be delivered within a predefined time period in response to engagement of the bolus constraint; and an insulin delivery device configured to deliver insulin to the host, wherein the insulin delivery device is at least one of physically connected to a receiver and operably connected to a receiver, wherein the insulin delivery device is configured to receive the insulin therapy from the controller module.

In an embodiment of the third aspect, the insulin therapy instruction is determined solely on internally derived data and the bolus constraint.

In an embodiment of the third aspect, the system further comprises at least one of a selectable button configured to allow a user to engage the engageable bolus constraint, a scroll wheel configured to allow a user to engage the engageable bolus constraint, and a menu selection configured to allow a user to engage the engageable bolus constraint.

In an embodiment of the third aspect, the insulin therapy instruction comprises an instruction to deliver a portion of the maximum total insulin dose.

In an embodiment of the third aspect, the insulin delivery device is configured to deliver insulin automatically in response to receiving the insulin therapy instruction.

In an embodiment of the third aspect, the bolus constraint is programmable by as least one of the host and a caretaker of the host.

In an embodiment of the third aspect, the bolus constraint is programmable by as least one of the bolus controller module and a manufacturer of the integrated system.

In an embodiment of the third aspect, the bolus controller module is configured to iteratively determine an insulin therapy instruction in response to internally derived data and an engaged bolus constraint, wherein the bolus controller module comprises programming to adjust the bolus constraint in response to internally derived data.

In an embodiment of the third aspect, the bolus controller module is further configured to calculate insulin therapy in response to a host's metabolic response to an insulin therapy, wherein the controller module comprises programming to adjust the bolus constraint in response to the host's metabolic response.

In an embodiment of the third aspect, the insulin delivery device is configured to provide delivery device data associated with insulin delivery.

In an embodiment of the third aspect, the internally derived data comprises at least one of sensor data, processed sensor data, delivery device data and processed delivery device data.

In an embodiment of the third aspect, the internally derived data further comprises at least one of a glucose concentration, a glucose concentration range, a change in glucose concentration, a glucose concentration rate of change, an acceleration of the glucose concentration rate of change, a host insulin sensitivity, a change in host insulin sensitivity, a host metabolic response to insulin therapy, an amount of insulin delivered, a time of insulin delivery, an insulin on board, and a time.

In an embodiment of the third aspect, the integrated system further comprises an auxiliary sensor configured to provide auxiliary sensor data associated with at least one measurement taken by the auxiliary sensor in the host, wherein the internally derived data further comprises auxiliary sensor data.

In an embodiment of the third aspect, the auxiliary sensor comprises at least one of an accelerometer, a pressure sensor, a pH sensor, a temperature sensor, an oxygen sensor, an auxiliary glucose sensor, an analyte sensor configured to measure an analyte other than glucose, a proximity sensor, and an orientation sensor.

BRIEF DESCRIPTION OF THE DRAWINGS

FIG. 2B is a perspective view of an in vivo portion of a transcutaneous continuous glucose sensor in one embodiment.

FIG. 2C is a cross-section of the portion of a transcutaneous continuous glucose sensor, of FIG. 2B, taken along line 2C-2C, in one embodiment.

DETAILED DESCRIPTION OF THE PREFERRED EMBODIMENT

Figure 1:
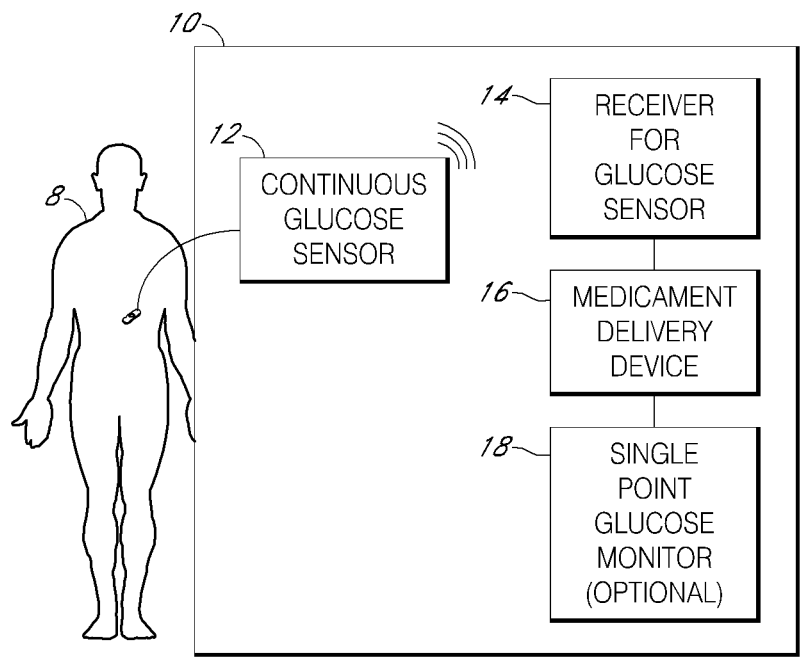
FIG. 1 is a block diagram of an integrated system of the preferred embodiments, including a continuous glucose sensor, a receiver for processing and displaying sensor data, a medicament delivery device, and an optional single point glucose-monitoring device.

The following description and examples illustrate some exemplary embodiments of the disclosed invention in detail.

Those of skill in the art will recognize that there are numerous variations and modifications of this invention that are encompassed by its scope. Accordingly, the description of a certain exemplary embodiment should not be deemed to limit the scope of the present invention.

Definitions

In order to facilitate an understanding of the disclosed invention, a number of terms are defined below.

The term "continuous glucose sensor," as used herein is a broad term, and is to be given its ordinary and customary meaning to a person of ordinary skill in the art (and is not to be limited to a special or customized meaning), and refers without limitation to a device that continuously or continually measures the glucose concentration of a bodily fluid (e.g., blood, plasma, interstitial fluid and the like), for example, at time intervals ranging from fractions of a second up to, for example, 1, 2, or 5 minutes, or longer. It should be understood that continual or continuous glucose sensors can continually measure glucose concentration without requiring user initiation and/or interaction for each measurement, such as described with reference to U.S. Pat. No. 6,001,067, for example.

The phrase "continuous glucose sensing," as used herein is a broad term, and is to be given its ordinary and customary meaning to a person of ordinary skill in the art (and is not to be limited to a special or customized meaning), and refers without limitation to the period in which monitoring of the glucose concentration of a host's bodily fluid (e.g., blood, serum, plasma, extracellular fluid, etc.) is continuously or continually performed, for example, at time intervals ranging from fractions of a second up to, for example, 1, 2, or 5 minutes, or longer. In one exemplary embodiment, the glucose concentration of a host's extracellular fluid is measured every 1, 2, 5, 10, 20, 30, 40, 50 or 60-seconds.

The term "biological sample," as used herein is a broad term, and is to be given its ordinary and customary meaning to a person of ordinary skill in the art (and is not to be limited to a special or customized meaning), and refers without limitation to sample of a host body, for example, blood, interstitial fluid, spinal fluid, saliva, urine, tears, sweat, or the like.

The term "host," as used herein as used herein is a broad term, and is to be given its ordinary and customary meaning to a person of ordinary skill in the art (and is not to be limited to a special or customized meaning), and refers without limitation to mammals such as humans.

The term "biointerface membrane," as used herein is a broad term, and is to be given its ordinary and customary meaning to a person of ordinary skill in the art (and is not to be limited to a special or customized meaning), and refers without limitation to a permeable or semi-permeable membrane that can include two or more domains and is typically constructed of materials of a few microns thickness or more, which can be placed over the sensing region to keep host cells (for example, macrophages) from gaining proximity to, and thereby damaging the sensing membrane or forming a barrier cell layer and interfering with the transport of glucose across the tissue-device interface.

The term "sensing membrane," as used herein is a broad term, and is to be given its ordinary and customary meaning to a person of ordinary skill in the art (and is not to be limited to a special or customized meaning), and refers without limitation to a permeable or semi-permeable membrane that can be comprised of two or more domains and is typically constructed of materials of a few microns thickness or more, which are permeable to oxygen and are optionally permeable to glucose. In one example, the sensing membrane comprises an immobilized glucose oxidase enzyme, which enables an electrochemical reaction to occur to measure a concentration of glucose.

The term "domain," as used herein is a broad term, and is to be given its ordinary and customary meaning to a person of ordinary skill in the art (and is not to be limited to a special or customized meaning), and refers without limitation to regions of a membrane that can be layers, uniform or non-uniform gradients (for example, anisotropic), functional aspects of a material, or provided as portions of the membrane.

As used herein, the term "copolymer," as used herein is a broad term, and is to be given its ordinary and customary meaning to a person of ordinary skill in the art (and is not to be limited to a special or customized meaning), and refers without limitation to polymers having two or more different repeat units and includes copolymers, terpolymers, tetrapolymers, etc.

The term "sensing region," as used herein is a broad term, and is to be given its ordinary and customary meaning to a person of ordinary skill in the art (and is not to be limited to a special or customized meaning), and refers without limitation to the region of a monitoring device (e.g., an analyte sensor) responsible for the detection of a particular analyte, such as but not limited to glucose. In one embodiment, the sensing region generally comprises a non-conductive body, a working electrode (anode), a reference electrode and a counter electrode (cathode) passing through and secured within the body forming an electrochemically reactive surface at one location on the body and an electronic connection at another location on the body, and a sensing membrane affixed to the body and covering the electrochemically reactive surface. The counter electrode typically has a greater electrochemically reactive surface area than the working electrode. During general operation of the sensor a biological sample (for example, blood or interstitial fluid) or a portion thereof contacts (for example, directly or after passage through one or more domains of the sensing membrane) an enzyme (for example, glucose oxidase, GOx); the reaction of the biological sample (or portion thereof) results in the formation of reaction products that allow a determination of the glucose level in the biological sample. In one exemplary embodiment, the sensing region includes at least one working electrode and a second electrode, which can function as a reference and/or counter electrode. In another exemplary embodiment, the sensing region includes a plurality of working electrodes, a counter electrode and a reference electrode.

The term "electrochemically reactive surface," as used herein is a broad term, and is to be given its ordinary and customary meaning to a person of ordinary skill in the art (and is not to be limited to a special or customized meaning), and refers without limitation to the surface of an electrode where an electrochemical reaction takes place. In the case of the working electrode, the hydrogen peroxide produced by the enzyme catalyzed reaction of the glucose being detected reacts creating a measurable electronic current (for example, detection of glucose utilizing glucose oxidase produces $H_2O_2$ as a by product, $H_2O_2$ reacts with the surface of the working electrode producing two protons ($2H^+$), two electrons ($2e^-$) and one molecule of oxygen ($O_2$) which produces the electronic current being detected). In the case of the counter electrode, a reducible species (for example, $O_2$) is reduced at the electrode surface in order to balance the current being generated by the working electrode.

The term "electrochemical cell," as used herein is a broad term, and is to be given its ordinary and customary meaning to a person of ordinary skill in the art (and is not to be limited to a special or customized meaning), and refers without limitation to a device in which chemical energy is converted to electrical energy. Such a cell typically consists of two or more electrodes held apart from each other and in contact with an electrolyte solution. Connection of the electrodes to a source of direct electric current renders one of them negatively charged and the other positively charged. Positive ions in the electrolyte migrate to the negative electrode (cathode) and there combine with one or more electrons, losing part or all of their charge and becoming new ions having lower charge or neutral atoms or molecules; at the same time, negative ions migrate to the positive electrode (anode) and transfer one or more electrons to it, also becoming new ions or neutral particles. The overall effect of the two processes is the transfer of electrons from the negative ions to the positive ions, a chemical reaction.

The term "proximal" as used herein is a broad term, and is to be given its ordinary and customary meaning to a person of ordinary skill in the art (and is not to be limited to a special or customized meaning), and refers without limitation to near to a point of reference such as an origin or a point of attachment. For example, in some embodiments of a sensing membrane that covers an electrochemically reactive surface, the electrolyte domain is located more proximal to the electrochemically reactive surface than the interference domain.

The term "distal" as used herein is a broad term, and is to be given its ordinary and customary meaning to a person of ordinary skill in the art (and is not to be limited to a special or customized meaning), and refers without limitation to spaced relatively far from a point of reference, such as an origin or a point of attachment. For example, in some embodiments of a sensing membrane that covers an electrochemically reactive surface, a resistance domain is located more distal to the electrochemically reactive surfaces than the enzyme domain.

The term "substantially" as used herein is a broad term, and is to be given its ordinary and customary meaning to a person of ordinary skill in the art (and is not to be limited to a special or customized meaning), and refers without limitation to being largely but not necessarily wholly that which is specified, which may include an amount greater than 50 percent, an amount greater than 60 percent, an amount greater than 70 percent, an amount greater than 80 percent, an amount greater than 90 percent or more.

The terms "processor" and "processor module," as used herein are a broad terms, and are to be given their ordinary and customary meaning to a person of ordinary skill in the art (and are not to be limited to a special or customized meaning), and refer without limitation to a computer system, state machine, processor, or the like designed to perform arithmetic or logic operations using logic circuitry that responds to and processes the basic instructions that drive a computer. In some embodiments, the terms can include ROM and/or RAM associated therewith.

The term "ROM," as used herein is a broad term, and is to be given its ordinary and customary meaning to a person of ordinary skill in the art (and is not to be limited to a special or customized meaning), and refers without limitation to read-only memory, which is a type of data storage device manufactured with fixed contents. ROM is broad enough to include EEPROM, for example, which is electrically erasable programmable read-only memory (ROM).

The term "RAM," as used herein is a broad term, and is to be given its ordinary and customary meaning to a person of ordinary skill in the art (and is not to be limited to a special or customized meaning), and refers without limitation to a data storage device for which the order of access to different locations does not affect the speed of access. RAM is broad enough to include SRAM, for example, which is static random access memory that retains data bits in its memory as long as power is being supplied.

The term "A/D Converter," as used herein is a broad term, and is to be given its ordinary and customary meaning to a person of ordinary skill in the art (and is not to be limited to a special or customized meaning), and refers without limitation to hardware and/or software that converts analog electrical signals into corresponding digital signals.

The term "RF module," as used herein is a broad term, and is to be given its ordinary and customary meaning to a person of ordinary skill in the art (and is not to be limited to a special or customized meaning), and refers without limitation to a radio frequency transmitter and/or receiver for transmitting and/or receiving signals.

The terms "raw data stream" and "data stream," as used herein are broad terms, and are to be given their ordinary and customary meaning to a person of ordinary skill in the art (and are not to be limited to a special or customized meaning), and refer without limitation to an analog or digital signal directly related to the analyte concentration measured by the analyte sensor. In one example, the raw data stream is digital data in "counts" converted by an A/D converter from an analog signal (for example, voltage or amps) representative of an analyte concentration. The terms broadly encompass a plurality of time spaced data points from a substantially continuous analyte sensor, which comprises individual measurements taken at time intervals ranging from fractions of a second up to, for example, 1, 2, or 5 minutes or longer.

The term "counts," as used herein is a broad term, and is to be given its ordinary and customary meaning to a person of ordinary skill in the art (and is not to be limited to a special or customized meaning), and refers without limitation to a unit of measurement of a digital signal. In one example, a raw data stream measured in counts is directly related to a voltage (for example, converted by an A/D converter), which is directly related to current from a working electrode.

The term "electronic circuitry," as used herein is a broad term, and is to be given its ordinary and customary meaning to a person of ordinary skill in the art (and is not to be limited to a special or customized meaning), and refers without limitation to the components (for example, hardware and/or software) of a device configured to process data. In the case of an analyte sensor, the data includes biological information obtained by a sensor regarding the concentration of the analyte in a biological fluid. U.S. Pat. Nos. 4,757,022, 5,497,772 and 4,787,398, which are hereby incorporated by reference in their entirety, describe suitable electronic circuits that can be utilized with devices of certain embodiments.

The term "potentiostat," as used herein is a broad term, and is to be given its ordinary and customary meaning to a person of ordinary skill in the art (and is not to be limited to a special or customized meaning), and refers without limitation to an electrical system that controls the potential between the working and reference electrodes of a three-electrode cell at a preset value. The potentiostat forces whatever current is necessary to flow between the working and counter electrodes to keep the desired potential, as long as the needed cell voltage and current do not exceed the compliance limits of the potentiostat.

The terms "operably connected" and "operably linked," as used herein are broad terms, and are to be given their ordinary and customary meaning to a person of ordinary skill in the art (and are not to be limited to a special or customized meaning), and refer without limitation to one or more components being linked to another component(s) in a manner that allows transmission of signals between the components. For example, one or more electrodes can be used to detect the amount of glucose in a sample and convert that information into a signal; the signal can then be transmitted to an electronic circuit. In this case, the electrode is "operably linked" to the electronic circuit. These terms are broad enough to include wired and wireless connectivity.

The term "algorithmically smoothed," as used herein is a broad term, and is to be given its ordinary and customary meaning to a person of ordinary skill in the art (and is not to be limited to a special or customized meaning), and refers without limitation to modification of a set of data to make it smoother and more continuous and remove or diminish outlying points, for example, by performing a moving average of the raw data stream.

The term "algorithm," as used herein is a broad term, and is to be given its ordinary and customary meaning to a person of ordinary skill in the art (and is not to be limited to a special or customized meaning), and refers without limitation to the computational processes (for example, programs) involved in transforming information from one state to another, for example using computer processing.

The term "regression," as used herein is a broad term, and is to be given its ordinary and customary meaning to a person of ordinary skill in the art (and is not to be limited to a special or customized meaning), and refers without limitation to finding a line in which a set of data has a minimal measurement (for example, deviation) from that line. Regression can be linear, non-linear, first order, second order, and so forth. One example of regression is least squares regression.

The terms "recursive filter" and "auto-regressive algorithm," as used herein are broad terms, and are to be given their ordinary and customary meaning to a person of ordinary skill in the art (and are not to be limited to a special or customized meaning), and refer without limitation to an equation in which previous averages are part of the next filtered output. More particularly, the generation of a series of observations whereby the value of each observation is partly dependent on the values of those that have immediately preceded it. One example is a regression structure in which lagged response values assume the role of the independent variables.

The terms "velocity" and "rate of change," as used herein are broad terms, and are to be given their ordinary and customary meaning to a person of ordinary skill in the art (and are not to be limited to a special or customized meaning), and refer without limitation to time rate of change; the amount of change divided by the time required for the change. In one embodiment, these terms refer to the rate of increase or decrease in an analyte for a certain time period.

The term "acceleration" as used herein is a broad term, and is to be given its ordinary and customary meaning to a person of ordinary skill in the art (and is not to be limited to a special or customized meaning), and refers without limitation to the rate of change of velocity with respect to time. This term is broad enough to include deceleration.

The term "clinical risk," as used herein is a broad term, and is to be given its ordinary and customary meaning to a person of ordinary skill in the art (and is not to be limited to a special or customized meaning), and refers without limitation to an identified danger or potential risk to the health of a host based on a measured or estimated analyte concentration, its rate of change, and/or its acceleration.

The term "clinically acceptable," as used herein is a broad term, and is to be given its ordinary and customary meaning to a person of ordinary skill in the art (and is not to be limited to a special or customized meaning), and refers without limitation to an analyte concentration, rate of change, and/or acceleration associated with that measured analyte that is considered to be safe for a host.

The term "time period," as used herein is a broad term, and is to be given its ordinary and customary meaning to a person of ordinary skill in the art (and is not to be limited to a special or customized meaning), and refers without limitation to an amount of time including a single point in time and a path (for example, range of time) that extends from a first point in time to a second point in time.

The term "measured analyte values," as used herein is a broad term, and is to be given its ordinary and customary meaning to a person of ordinary skill in the art (and is not to be limited to a special or customized meaning), and refers without limitation to an analyte value or set of analyte values for a time period for which analyte data has been measured by an analyte sensor. The term is broad enough to include data from the analyte sensor before or after data processing in the sensor and/or receiver (for example, data smoothing, calibration, or the like).

The term "alarm," as used herein is a broad term, and is to be given its ordinary and customary meaning to a person of ordinary skill in the art (and is not to be limited to a special or customized meaning), and refers without limitation to audible, visual, or tactile signal that are triggered in response to detection of clinical risk to a host. In one embodiment, hyperglycemic and hypoglycemic alarms are triggered when present or future clinical danger is assessed based on continuous analyte data.

The term "computer," as used herein is a broad term, and is to be given its ordinary and customary meaning to a person of ordinary skill in the art (and is not to be limited to a special or customized meaning), and refers without limitation to a machine that can be programmed to manipulate data.

The term "modem," as used herein is a broad term, and is to be given its ordinary and customary meaning to a person of ordinary skill in the art (and is not to be limited to a special or customized meaning), and refers without limitation to an electronic device for converting between serial data from a computer and an audio signal suitable for transmission over a telecommunications connection to another modem.

The term "intelligent," as used herein is a broad term, and is to be given its ordinary and customary meaning to a person of ordinary skill in the art (and is not to be limited to a special or customized meaning), and refers without limitation to systems and methods programmed to be able to adjust to changes in the current conditions and make deductions from information being processed.

The term "adaptive," as used herein is a broad term, and is to be given its ordinary and customary meaning to a person of ordinary skill in the art (and is not to be limited to a special or customized meaning), and refers without limitation to an ability (e.g., systems and methods able to) to be adjusted for use in different conditions; to change something to suit different conditions. In some embodiments, an adaptive controller module can be configured to adjust the medicament delivery rate, the medicament volume, the time of delivery, and the like, based on evaluation of internally derived data and the host metabolic response to therapy.

The term "condition," as used herein is a broad term, and is to be given its ordinary and customary meaning to a person of ordinary skill in the art (and is not to be limited to a special or customized meaning), and refers without limitation to a mode or state of being; the physical status of the body as a whole or of one of its parts. For example, a host's condition can refer to his state of health, his metabolic state and the like.

The term "glucose boundary," as used herein is a broad term, and is to be given its ordinary and customary meaning to a person of ordinary skill in the art (and is not to be limited to a special or customized meaning), and refers without limitation to a glucose concentration or range of glucose concentrations. In some embodiments, the system is configured to compare and/or evaluate internally derived data with a glucose boundary. In some embodiments, a glucose boundary can include a maximum glucose concentration.

The term "on/off controller module," as used herein is a broad term, and is to be given its ordinary and customary meaning to a person of ordinary skill in the art (and is not to be limited to a special or customized meaning), and refers without limitation to a mechanism configured to select between two instructions, namely either "on" or "off" An on/off controller module can include a device, such as a switch, programming or a combination thereof, that can actuate and/or de-actuate an insulin delivery device, such that the device is either delivering insulin or not delivering insulin. In some embodiments, the on instruction is sent to the insulin delivery device, which is configured to deliver the insulin, such as to automatically deliver the insulin; similarly, the off instruction can be sent to the insulin delivery device, which terminates insulin delivery upon receipt of the off instruction.

The term "basal," as used herein is a broad term, and is to be given its ordinary and customary meaning to a person of ordinary skill in the art (and is not to be limited to a special or customized meaning), and refers without limitation to the minimum required rate or other value for something to function. For example, in the case of insulin therapy, the term "basal rate" can refer to a regular (e.g., in accordance with fixed order or procedure, such as regularly scheduled for/at a fixed time), periodic or continuous delivery of low levels of insulin, such as but not limited to throughout a 24-hour period.

The term "basal profile," as used herein is a broad term, and is to be given its ordinary and customary meaning to a person of ordinary skill in the art (and is not to be limited to a special or customized meaning), and refers without limitation to an insulin delivery schedule that includes one or more blocks of time (e.g., time blocks), wherein each block is associated with a maximum insulin delivery rate.

The term "dynamic basal controller module," as used herein is a broad term, and is to be given its ordinary and customary meaning to a person of ordinary skill in the art (and is not to be limited to a special or customized meaning), and refers without limitation to a controller module configured to intelligently and adaptively evaluate internally derived data relative to a basal profile and to determine a basal insulin therapy (e.g., an insulin delivery rate) based thereon, wherein the insulin therapy can include a delivery rate of up to the maximum delivery rate associated with a time block of the basal profile.

The term "bolus," as used herein is a broad term, and is to be given its ordinary and customary meaning to a person of ordinary skill in the art (and is not to be limited to a special or customized meaning), and refers without limitation to a single dose of insulin, usually given over a short, defined period of time, that has been calculated and/or estimated to be sufficient to cover an expected rise in blood glucose, such as the rise that generally occurs during/after a meal.

The term "bolus constraint," as used herein is a broad term, and is to be given its ordinary and customary meaning to a person of ordinary skill in the art (and is not to be limited to a special or customized meaning), and refers without limitation to an engageable (e.g., selectable) maximum total insulin therapy (e.g., maximum total dose) that can be delivered during a defined period of time. In some embodiments, the bolus constraint has been calculated/estimated to be sufficient to cover an expected rise in glucose, such as an average glucose increase associate with consumption of a meal. In some embodiments, the host, a caretaker of the host, and/or the manufacturer can program a bolus constraint. In some circumstances, a bolus constraint can be programmed by an intelligent/adaptive controller module.

The term "dynamic bolus controller module," as used herein is a broad term, and is to be given its ordinary and customary meaning to a person of ordinary skill in the art (and is not to be limited to a special or customized meaning), and refers without limitation to a controller module configured to intelligently and adaptively evaluate internally derived data against (e.g., relative to) an engaged bolus constraint and to calculate an therapy based thereon, wherein the calculations are constrained by the engaged bolus constraint. A dynamic bolus controller module can include one or more instructions for calculation and/or delivery of a dynamic basal insulin therapy, such as but not limited to instructions to the insulin delivery device to delivery the bolus therapy automatically.

The term "range," as used herein is a broad term, and is to be given its ordinary and customary meaning to a person of ordinary skill in the art (and is not to be limited to a special or customized meaning), and refers without limitation to a sequence, series, or scale between limits (e.g., maximum and minimum values). For example, a range of glucose concentrations can include glucose concentrations from 60 mg/dl to 200 mg/dl. In another example, a range of insulin delivery rates can include rates from about 0.01 U/hr to about 40 U/hr. In some embodiments, a range is a single value.

The terms "programmed" and "programmable," as used herein are broad terms, and are to be given their ordinary and customary meaning to a person of ordinary skill in the art (and are not to be limited to a special or customized meaning), and refer without limitation to being or able to be arranged, as in a series of steps and/or instructions to be carried out, such as by a computer. As used herein, the terms programmed and programmable includes "pre-programmed," "pre-programmable," "re-programmed" and "re-programmable." In one example, a constraint can be programmed prior to use and/or reprogrammed at a later time.

The term "internally derived data," as used herein is a broad term, and is to be given its ordinary and customary meaning to a person of ordinary skill in the art (and is not to be limited to a special or customized meaning), and refers without limitation to data measured and/or processed by the integrated system, or a component thereof. Internally derived data can include data from a system component, such as but not limited to an analyte sensor (e.g., continuous glucose sensor), an auxiliary sensor, and/or an insulin delivery device. Internally derived data can include data derived (e.g., by processing and/or algorithmic evaluation) from the data received from a system component, such as but not limited to processed data, evaluated raw and/or processed data, host insulin sensitivity, host metabolic response, relationship of insulin sensitivity and/or metabolic response to each other, time, activity level, tracking of internally derived data to establish trends, insulin delivered and/or on-board, and the like. In some circumstances, internally derived data can include older and/or new data, such as but not limited to data received in the past (e.g., minutes, hours, days, weeks or months) and/or recently received data (e.g., currently received, instant, such as but not limited to within the previous 1-15 minutes). In some embodiments, a controller module can evaluate the internally derived data as it is received.

The term "insulin therapy," as used herein is a broad term, and is to be given its ordinary and customary meaning to a person of ordinary skill in the art (and is not to be limited to a special or customized meaning), and refers without limitation to an amount and/or schedule of the insulin to be delivered to the host. An insulin therapy can include one or more doses of insulin, up to the maximum (e.g., dose, therapy) associated with a constraint, such as but not limited to a basal profile and/or a bolus constraint. In some circumstances, the insulin therapy calculated and/or delivered can include a one or more partial doses that sum to an amount less than or equal to the maximum (e.g., dose, therapy) associated with a constraint. In some circumstances, the user can override the insulin therapy calculated by a controller module and/or associated with a constraint, such as, for example, to command the integrated system to deliver a manually entered insulin therapy.

The term "target range," as used herein is a broad term, and is to be given its ordinary and customary meaning to a person of ordinary skill in the art (and is not to be limited to a special or customized meaning), and refers without limitation to a range of glucose concentrations within which a host is to try to maintain his blood sugar. In general, a target range is a range of glucose concentrations considered to be euglycemic. Euglycemic glucose concentrations are discussed in detail in the section entitled "Programming and Processing."

The term "meal," as used herein is a broad term, and is to be given its ordinary and customary meaning to a person of ordinary skill in the art (and is not to be limited to a special or customized meaning), and refers without limitation to an amount of food or beverage consumed by the host. In some circumstances, a meal is associated with a time of day, during which that meal is generally consumed, such as but not limited to breakfast, lunch, dinner, supper, snack, and the like. In some circumstances, a meal is associated with a particular type of food or beverage, such as one that a host consumes only occasionally, such as but not limited to a high fat meal (e.g., pizza) or a high carbohydrate meal (e.g., cake, cookies, candy, ice cream, and the like).

The term "auxiliary sensor," as used herein is a broad term, and is to be given its ordinary and customary meaning to a person of ordinary skill in the art (and is not to be limited to a special or customized meaning), and refers without limitation to a sensor other than the continuous glucose sensor, which is configured to sense glucose or an analyte other than glucose, or to sense a condition, such as but not limited to temperature, pH, host activity level, orientation, pressure, proximity and the like.

Overview

FIG. 1 is a block diagram of an integrated system 10 of the preferred embodiments, including a continuous glucose sensor 12, a receiver 14 for processing and displaying sensor data, a medicament delivery device 16, and optionally a single point glucose-monitoring device 18. The integrated diabetes management system 10 of the preferred embodiments provides improved convenience and accuracy thus affording a diabetic host 8 with improved convenience, functionality, and safety in the care of their disease.

FIG. 1 shows a continuous glucose sensor 12 that measures a concentration of glucose or a substance indicative of the concentration or presence of the glucose. In some embodiments, the glucose sensor 12 is an invasive, minimally invasive, or non-invasive device, for example a subcutaneous, transdermal, intravascular or extracorporeal device. In some embodiments, the sensor 12 can analyze a plurality of intermittent biological samples. The glucose sensor can use any method of glucose-measurement, including enzymatic, chemical, physical, electrochemical, spectrophotometric, polarimetric, calorimetric, radiometric, or the like. In alternative embodiments, the sensor 12 can be any sensor capable of determining the level of an analyte in the body, for example oxygen, lactase, insulin, hormones, cholesterol, medicaments, viruses, or the like. The glucose sensor 12 uses any known method to provide an output signal indicative of the concentration of the glucose. The output signal is typically a raw data stream that is used to provide a useful value of the measured glucose concentration to a host or doctor, for example.

Accordingly, a receiver 14 is provided that receives and processes the raw data stream, including calibrating, validating, and displaying meaningful glucose values to a host, such as described in more detail below. A medicament delivery device 16 is further provided as a part of the integrated system 10. In some embodiments, the medicament delivery device 16 is a manual delivery device, for example a syringe, inhaler, or transdermal patch, which is manually integrated with the receiver 14. In some embodiments, the medicament delivery device 16 is a semi-automated delivery device, for example a pen or jet-type injector, an inhaler, a spray, or pump, which provides a semi-automated integration with the receiver 14. In some embodiments, the medicament delivery device 16 is an automated delivery device, for example a transcutaneous or implantable pump system, which provides an automated integration with the receiver 14. In some embodiments, an optional single point glucose monitor 18 is further provided as a part of the integrated system 10, for example a self-monitoring blood glucose meter (SMBG), non-invasive glucose meter, or the like.

Conventionally, each of these devices separately provides valuable information and or services to diabetic hosts. Thus, a typical diabetic host has numerous individual devices, which they track and consider separately. In some cases, the amount of information provided by these individual devices may require complex understanding of the nuances and implications of each device, for example types and amounts of insulin to deliver. Typically, each individual device is a silo of information that functions as well as the data provided therein, therefore when the devices are able to communicate with each other, enhanced functionality and safety can be realized. For example, when a continuous glucose monitor functions alone (for example, without data other than that which was gathered by the device), sudden changes in glucose level are tracked, but may not be fully understood, predicted, preempted, or otherwise considered in the processing of the sensor data; however, if the continuous glucose sensor were provided with information about time, amount, and type of insulin injections, calories consumed, time or day, meal time, or like, more meaningful, accurate and useful glucose estimation, prediction, and other such processing can be provided, such as described in more detail herein. By integrating these devices, the information from each component can be leveraged to increase the intelligence, benefit provided, convenience, safety, and functionality of the continuous glucose sensor and other integrated components. Therefore, it would be advantageous to provide a device that aids the diabetic host in integrating these individual devices in the treatment of his/her disease.

In the non-diabetic host, pancreatic β-cells generally respond quickly to spikes in blood glucose by releasing stored insulin (e.g., within about 10-minutes). In preferred embodiments, the integrated system 10 is configured to mimic pancreatic β-cells, and thereby to provide substantially physiological detection of glucose levels and/or insulin response. Accordingly, the system 10 includes a continuous analyte sensor, a medicament delivery device (e.g., an infusion pump, a pen, a syringe, an inhaler, a medicament patch, and the like), and associated electronics, as described elsewhere herein. In various embodiments, the electronics include one or more of an on/off controller module, a dynamic basal controller module and/or a dynamic bolus controller module, as described elsewhere herein. In some embodiments, the electronics include two or more controller modules configured to work in concert. The system 10 is configured for use with regular, rapid-acting, fast-acting and/or flash-acting insulins, which are described elsewhere herein. In one exemplary embodiment, the system 10 is configured to determine a medicament dose (e.g., an insulin dose) using solely internally derived data.

Glucose Sensor

Figure 2A:
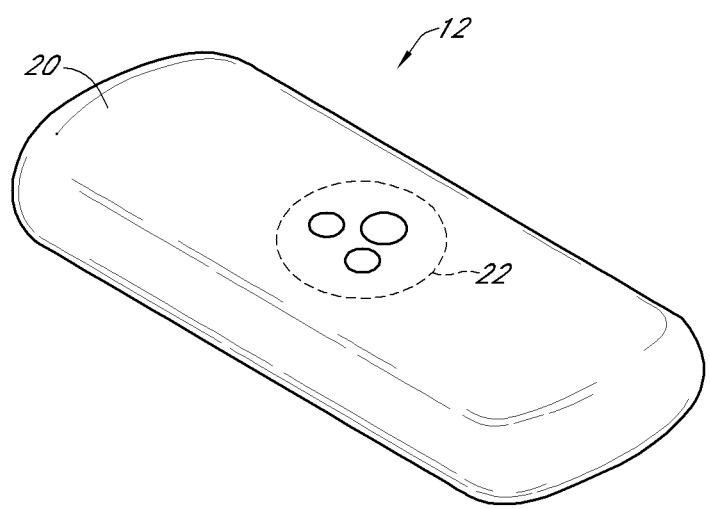
FIG. 2A is a perspective view of a continuous glucose sensor in one embodiment.
Figure 3:
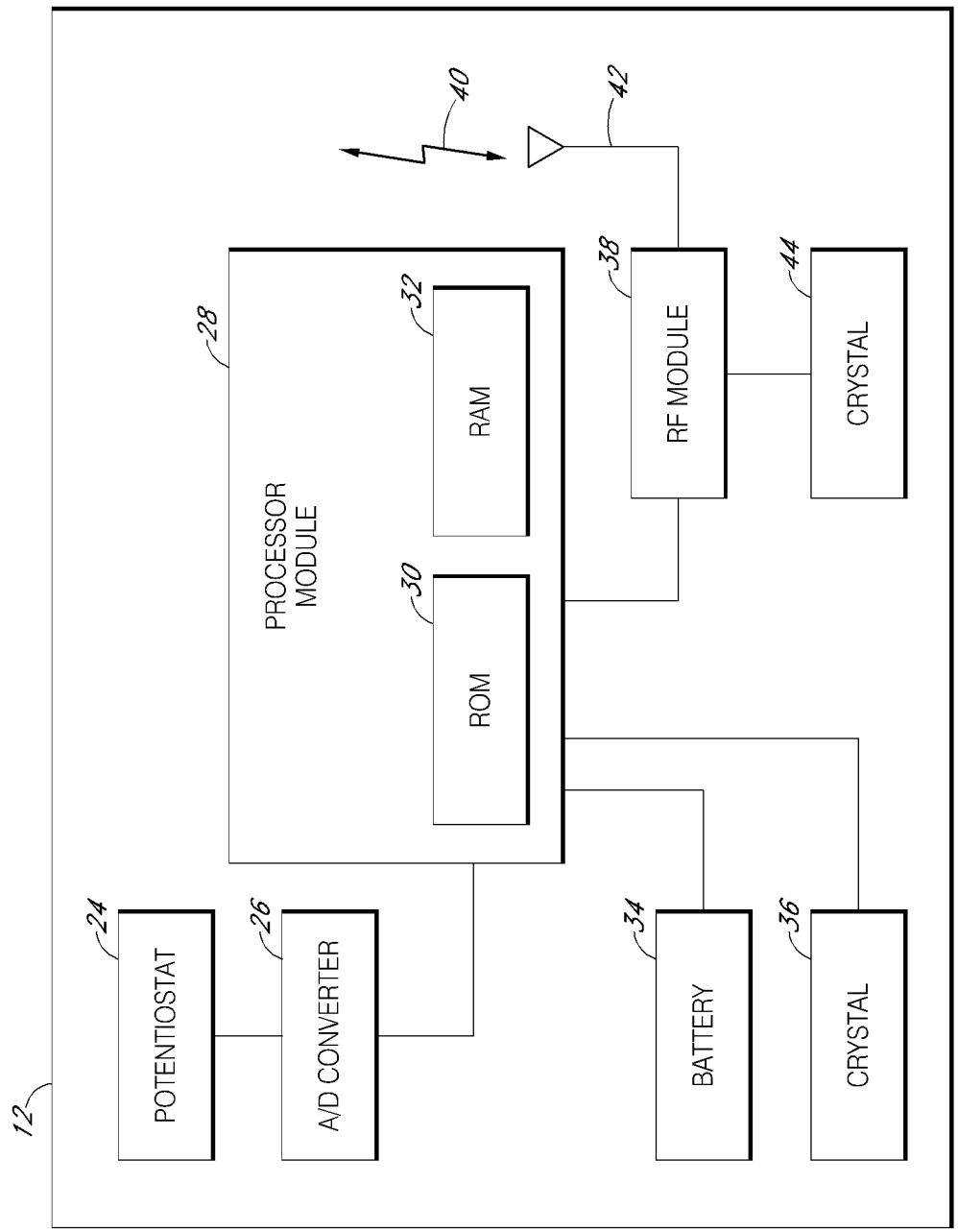
FIG. 3 is a block diagram of the electronics associated with a continuous glucose sensor in one embodiment.

FIG. 2A is a perspective view of one embodiment of a wholly implantable continuous glucose sensor 12 (e.g., the primary analyte sensor). In this embodiment, a body 20 and a sensing region 22 house the electrodes and sensor electronics (FIG. 3). The three electrodes within the sensing region are operably connected to the sensor electronics (FIG. 3) and are covered by a sensing membrane and a biointerface membrane (not shown), which are described in more detail below.

The body 20 is preferably formed from epoxy molded around the sensor electronics, however the body can be formed from a variety of materials, including metals, ceramics, plastics, or composites thereof. U.S. Pat. No. 7,134,999 discloses suitable configurations suitable for the body 20, and is incorporated by reference in its entirety.

In one embodiment, the sensing region 22 comprises three electrodes including a platinum working electrode, a platinum counter electrode, and a silver/silver chloride reference electrode, for example. However a variety of electrode materials and configurations can be used with the implantable glucose sensor of the preferred embodiments. The top ends of the electrodes are in contact with an electrolyte phase (not shown), which is a free-flowing fluid phase disposed between the sensing membrane and the electrodes. In one embodiment, the counter electrode is provided to balance the current generated by the species being measured at the working electrode. In the case of a glucose oxidase based glucose sensor, the species being measured at the working electrode is $H_2O_2$. Glucose oxidase catalyzes the conversion of oxygen and glucose to hydrogen peroxide and gluconate according to the following reaction:

$$Glucose + O_2 \rightarrow Gluconate + H_2O_2$$

The change in $H_2O_2$ can be monitored to determine glucose concentration because for each glucose molecule metabolized, there is a proportional change in the product $H_2O_2$. Oxidation of $H_2O_2$ by the working electrode is balanced by reduction of ambient oxygen, enzyme generated $H_2O_2$, or other reducible species at the counter electrode. The $H_2O_2$ produced from the glucose oxidase reaction further reacts at the surface of working electrode and produces two protons ($2H^+$), two electrons ($2e^-$), and one oxygen molecule ($O_2$).

In one embodiment, a potentiostat (FIG. 3) is employed to monitor the electrochemical reaction at the electroactive surface(s). The potentiostat applies a constant potential to the working and reference electrodes to determine a current value. The current that is produced at the working electrode (and flows through the circuitry to the counter electrode) is substantially proportional to the amount of $H_2O_2$ that diffuses to the working electrode. Accordingly, a raw signal can be produced that is representative of the concentration of glucose in the user's body, and therefore can be utilized to estimate a meaningful glucose value.

In some embodiments, the sensing membrane includes an enzyme, for example, glucose oxidase, and covers the electrolyte phase. In one embodiment, the sensing membrane generally includes a resistance domain most distal from the electrochemically reactive surfaces, an enzyme domain less distal from the electrochemically reactive surfaces than the resistance domain, and an electrolyte domain adjacent to the electrochemically reactive surfaces. However, it is understood that a sensing membrane modified for other devices, for example, by including fewer or additional domains, is within the scope of the preferred embodiments. U.S. Patent Publication No. US-2003-0032874-A1 describes membranes that can be used in some embodiments of the sensing membrane. It is noted that in some embodiments, the sensing membrane can additionally include an interference domain that blocks some interfering species; such as described in the above-cited co-pending patent application. U.S. Patent Publication No. US-2005-0090607-A1 also describes membranes that can be used for the sensing membrane of the preferred embodiments, and is incorporated herein by reference in its entirety.

Preferably, the biointerface membrane supports tissue ingrowth, serves to interfere with the formation of a barrier cell layer, and protects the sensitive regions of the device from host inflammatory response. In one embodiment, the biointerface membrane generally includes a cell disruptive domain most distal from the electrochemically reactive surfaces and a cell impermeable domain less distal from the electrochemically reactive surfaces than the cell disruptive domain. The cell disruptive domain is preferably designed to support tissue ingrowth, disrupt contractile forces typically found in a foreign body response, encourage vascularity within the membrane, and disrupt the formation of a barrier cell layer. The cell impermeable domain is preferably resistant to cellular attachment, impermeable to cells, and composed of a biostable material. U.S. Pat. Nos. 6,702,857, 7,192,450, and U.S. Patent Publication No. US-2005-0251083-A1 describe biointerface membranes that can be used in conjunction with the preferred embodiments, and are incorporated herein by reference in their entireties. It is noted that the preferred embodiments can be used with a short term (for example, 1 to 7 day sensor), in which case a biointerface membrane may not be required. It is noted that the biointerface membranes described herein provide a continuous glucose sensor that has a useable life of greater than about one week, greater than about one month, greater than about three months, or greater than about one year, herein after referred to as "long-term."

In some embodiments, the domains of the biointerface and sensing membranes are formed from materials such as silicone, polytetrafluoroethylene, polyethylene-co-tetrafluoroethylene, polyolefin, polyester, polycarbonate, biostable polytetrafluoroethylene, homopolymers, copolymers and/or terpolymers of polyurethanes, polypropylene (PP), polyvinylchloride (PVC), polyvinylidene fluoride (PVDF), polybutylene terephthalate (PBT), polymethylmethacrylate (PMMA), polyether ether ketone (PEEK), polyurethanes, cellulosic polymers, polysulfones and block copolymers thereof including, for example, di-block, tri-block, alternating, random and graft copolymers.

FIG. 2B is a perspective view of an in vivo portion of a transcutaneous continuous glucose sensor 12, in one embodiment. In this embodiment, the in vivo portion of the sensor includes at least one working electrode 12a and a reference electrode 12b and a sensing membrane 12c.

FIG. 2C is a cross-section of the sensor shown in FIG. 2B, taken on line 2C-2C. In preferred embodiments, the sensing membrane 12c (e.g., a biointerface and/or sensing membrane) includes at least an enzyme domain 12f having an enzyme configured to detect the analyte, such as but not limited to glucose oxidase, as described elsewhere herein. In some preferred embodiments, the sensing membrane 12c can include one or more additional domains, such as but not limited to an electrode domain 12d, an interference domain 12e, a resistance domain 12j, a cell disruptive domain and a cell impermeable domain, for example. Additional sensor and sensing membrane configurations can be found in U.S. Patent Publication No. US-2006-0020187-A1, U.S. Patent Publication No. US-2005-0031689-A1, U.S. Patent Publication No. 2007-0027370-A1, U.S. Patent Publication No. 2006-0229512-A1, U.S. Patent Publication No. 2006-0253012-A1, U.S. Patent Publication No. US-2007-0197890-A1, U.S. application Ser. No. 11/404,417 filed on Apr. 14, 2006 and entitled "SILICONE BASED MEMBRANES FOR USE IN IMPLANTABLE GLUCOSE SENSORS," and U.S. application Ser. No. 11/750,907 filed on May 18, 2007 and entitled "ANALYTE SENSORS HAVING AN OPTIMIZED SIGNAL-TO-NOISE RATIO," each of which is incorporated herein by reference in its entirety.

In preferred embodiments, the analyte sensor 12 is configured to provide response to changes in host glucose concentration, such as but not limited to a sensor response time of about 20-minutes or less. The term "sensor response time" as used herein is a broad term, and is to be given its ordinary and customary meaning to a person of ordinary skill in the art (and is not to be limited to a special or customized meaning), and refers without limitation to the time required for the sensor to measure a stable signal value associated with a change in glucose concentration, from a first concentration to a second concentration. The sensor response time can be measured by in vitro experimentation. For example, sensor response time can be measured by first placing a continuous glucose sensor in a first glucose solution (e.g., 100 mg/dl glucose); then moving the sensor to a second glucose solution (e.g., 200 mg/dl glucose) and allowing the sensor to equilibrate. In some embodiments, the sensor response time is less than about 10-minutes. In preferred embodiments, the sensor response time is less than 1, 2, 3, 4, or 5-minutes. In more preferred embodiments, the sensor response time is less than about 30-seconds. In some alternative embodiments, sensor response time includes an additional period of time required to process the measured glucose concentration change and provide a numerical output to the user (e.g., via a receiver).

FIG. 3 is a block diagram that illustrates the electronics associated with a continuous glucose sensor 12 in one embodiment. In this embodiment, a potentiostat 24 is shown, operably connected to an electrode system (such as described above) and provides a voltage to the electrodes (FIG. 2), which biases the sensor to enable measurement of a current signal indicative of the analyte concentration in the host (also referred to as the analog portion). In some embodiments, the potentiostat includes a resistor (not shown) that translates the current into voltage. In some alternative embodiments, a current to frequency converter is provided that is configured to continuously integrate the measured current, for example, using a charge counting device. An A/D converter 26 digitizes the analog signal into a digital signal, also referred to as "counts" in some embodiments for processing. Accordingly, the resulting raw data stream in counts, also referred to as raw sensor data, is directly related to the current measured by the potentiostat 24.

A processor module 28 includes the central control unit (houses ROM 30 and RAM 32) that controls the processing of the sensor electronics. In some embodiments, the processor module includes a microprocessor, however a computer system other than a microprocessor can be used to process data as described herein, for example an ASIC can be used for some or all of the sensor's central processing. The processor typically provides semi-permanent storage of data, for example, storing data such as sensor identifier (ID) and programming to process data streams (for example, programming for data smoothing and/or replacement of signal artifacts such as is described in U.S. Publication No. US-2005-0043598-A1). The processor additionally can be used for the system's cache memory, for example for temporarily storing recent sensor data. In some embodiments, the processor module comprises memory storage components such as ROM 30, RAM 32, dynamic-RAM, static-RAM, non-static RAM, EEPROM, rewritable ROMs, flash memory, or the like.

In some embodiments, the processor module comprises a digital filter, for example, an infinite impulse response (IIR) or finite impulse response (FIR) filter, configured to smooth the raw data stream from the A/D converter. Generally, digital filters are programmed to filter data sampled at a predetermined time interval (also referred to as a sample rate). In some embodiments, wherein the potentiostat is configured to measure the analyte at discrete time intervals, these time intervals determine the sample rate of the digital filter. In some alternative embodiments, wherein the potentiostat is configured to continuously measure the analyte, for example, using a current-to-frequency converter as described above, the processor module can be programmed to request a digital value from the A/D converter at a predetermined time interval, also referred to as the acquisition time. In these alternative embodiments, the values obtained by the processor are advantageously averaged over the acquisition time due the continuity of the current measurement. Accordingly, the acquisition time determines the sample rate of the digital filter. In preferred embodiments, the processor module is configured with a programmable acquisition time, namely, the predetermined time interval for requesting the digital value from the A/D converter is programmable by a user within the digital circuitry of the processor module. An acquisition time of from about 2 seconds to about 512 seconds is preferred; however any acquisition time can be programmed into the processor module. A programmable acquisition time is advantageous in optimizing noise filtration, time lag, and processing/battery power.

Preferably, the processor module 28 is configured to build the data packet for transmission to an outside source, for example, a Radio Frequency (RF) transmission (e.g., via RF module 38) to a receiver as described in more detail below. Generally, the data packet comprises a plurality of bits that can include a preamble, a unique identifier identifying the electronics unit, the receiver, or both, (e.g., sensor ID code), data (e.g., raw data, filtered data, and/or an integrated value) and/or error detection or correction. Preferably, the data (transmission) packet has a length of from about 8 bits to about 128 bits, preferably about 48 bits; however, larger or smaller packets can be desirable in certain embodiments. The processor module 28 can be configured to transmit any combination of raw and/or filtered data. In one exemplary embodiment, the transmission packet contains a fixed preamble, a unique ID of the electronics unit, a single five-minute average (e.g., integrated) sensor data value, and a cyclic redundancy code (CRC).

In some embodiments, the processor module 28 further comprises a transmitter portion that determines the transmission interval of the sensor data to a receiver, or the like. In some embodiments, the transmitter portion, which determines the interval of transmission, is configured to be programmable. In one such embodiment, a coefficient can be chosen (e.g., a number of from about 1 to about 100, or more), wherein the coefficient is multiplied by the acquisition time (or sampling rate), such as described above, to define the transmission interval of the data packet. Thus, in some embodiments, the transmission interval is programmable from about 2 seconds to about 850 minutes, more preferably from about 30 second to about 5 minutes; however, any transmission interval can be programmable or programmed into the processor module. However, a variety of alternative systems and methods for providing a programmable transmission interval can also be employed. By providing a programmable transmission interval, data transmission can be customized to meet a variety of design criteria (e.g., reduced battery consumption, timeliness of reporting sensor values, etc.).

Conventional glucose sensors measure current in the nanoAmp range. In contrast to conventional glucose sensors, the preferred embodiments are configured to measure the current flow in the picoAmp range, and in some embodiments, femtoAmps. Namely, for every unit (mg/dL) of glucose measured, at least one picoAmp of current is measured. Preferably, the analog portion of the A/D converter 26 is configured to continuously measure the current flowing at the working electrode and to convert the current measurement to digital values representative of the current. In one embodiment, the current flow is measured by a charge counting device (e.g., a capacitor). Preferably, a charge counting device provides a value (e.g., digital value) representative of the current flow integrated over time (e.g., integrated value). In some embodiments, the value is integrated over a few seconds, a few minutes, or longer. In one exemplary embodiment, the value is integrated over 5 minutes; however, other integration periods can be chosen. Thus, a signal is provided, whereby a high sensitivity maximizes the signal received by a minimal amount of measured hydrogen peroxide (e.g., minimal glucose requirements without sacrificing accuracy even in low glucose ranges), reducing the sensitivity to oxygen limitations in vivo (e.g., in oxygen-dependent glucose sensors).

In some embodiments, the electronics unit is programmed with a specific ID, which is programmed (automatically or by the user) into a receiver to establish a secure wireless communication link between the electronics unit and the receiver. Preferably, the transmission packet is Manchester encoded; however, a variety of known encoding techniques can also be employed.

A battery 34 is operably connected to the sensor electronics and provides the power for the sensor 12. In one embodiment, the battery is a lithium manganese dioxide battery; however, any appropriately sized and powered battery can be used (for example, AAA, nickel-cadmium, zinc-carbon, alkaline, lithium, nickel-metal hydride, lithium-ion, zinc-air, zinc-mercury oxide, silver-zinc, and/or hermetically-sealed). In some embodiments, the battery is rechargeable, and/or a plurality of batteries can be used to power the system. The sensor can be transcutaneously powered via an inductive coupling, for example. In some embodiments, a quartz crystal 36 is operably connected to the processor 28 and maintains system time for the computer system as a whole, for example for the programmable acquisition time within the processor module.

An RF module 38 is operably connected to the processor 28 and transmits the sensor data from the sensor 12 to a receiver within a wireless transmission 40 via antenna 42. In some embodiments, a second quartz crystal 44 provides the time base for the RF carrier frequency used for data transmissions from the RF module 38. In some alternative embodiments, however, other mechanisms, such as optical, infrared radiation (IR), ultrasonic, or the like, can be used to transmit and/or receive data.

In the RF telemetry module of the preferred embodiments, the hardware and software are designed for low power requirements to increase the longevity of the device (for example, to enable a life of from about 3 to about 24 months, or more) with maximum RF transmittance from the in vivo environment to the ex vivo environment for wholly implantable sensors (for example, a distance of from about one to ten meters or more). Preferably, a high frequency carrier signal of from about 402 MHz to about 433 MHz is employed in order to maintain lower power requirements. In some embodiments, the RF module employs a one-way RF communication link to provide a simplified ultra low power data transmission and receiving scheme. The RF transmission can be OOK or FSK modulated, preferably with a radiated transmission power (EIRP) fixed at a single power level of typically less than about 100 microwatts, preferably less than about 75 microwatts, more preferably less than about 50 microwatts, and most preferably less than about 25 microwatts.

In one alternative embodiment, the continuous glucose sensor comprises a transcutaneous sensor such as described in U.S. Pat. No. 6,565,509 to Say et al. In another alternative embodiment, the continuous glucose sensor comprises a subcutaneous sensor such as described with reference to U.S. Pat. No. 6,579,690 to Bonnecaze et al. and U.S. Pat. No. 6,484,046 to Say et al. In another alternative embodiment, the continuous glucose sensor comprises a refillable subcutaneous sensor such as described with reference to U.S. Pat. No. 6,512,939 to Colvin et al. In another alternative embodiment, the continuous glucose sensor comprises an intravascular sensor such as described with reference to U.S. Pat. No. 6,477,395 to Schulman et al. In another alternative embodiment, the continuous glucose sensor comprises an intravascular sensor such as described with reference to U.S. Pat. No. 6,424,847 to Mastrototaro et al. All of the above patents are incorporated in their entirety herein by reference. In general, it should be understood that the disclosed embodiments are applicable to a variety of continuous glucose sensor configurations.

Receiver

Figure 9:
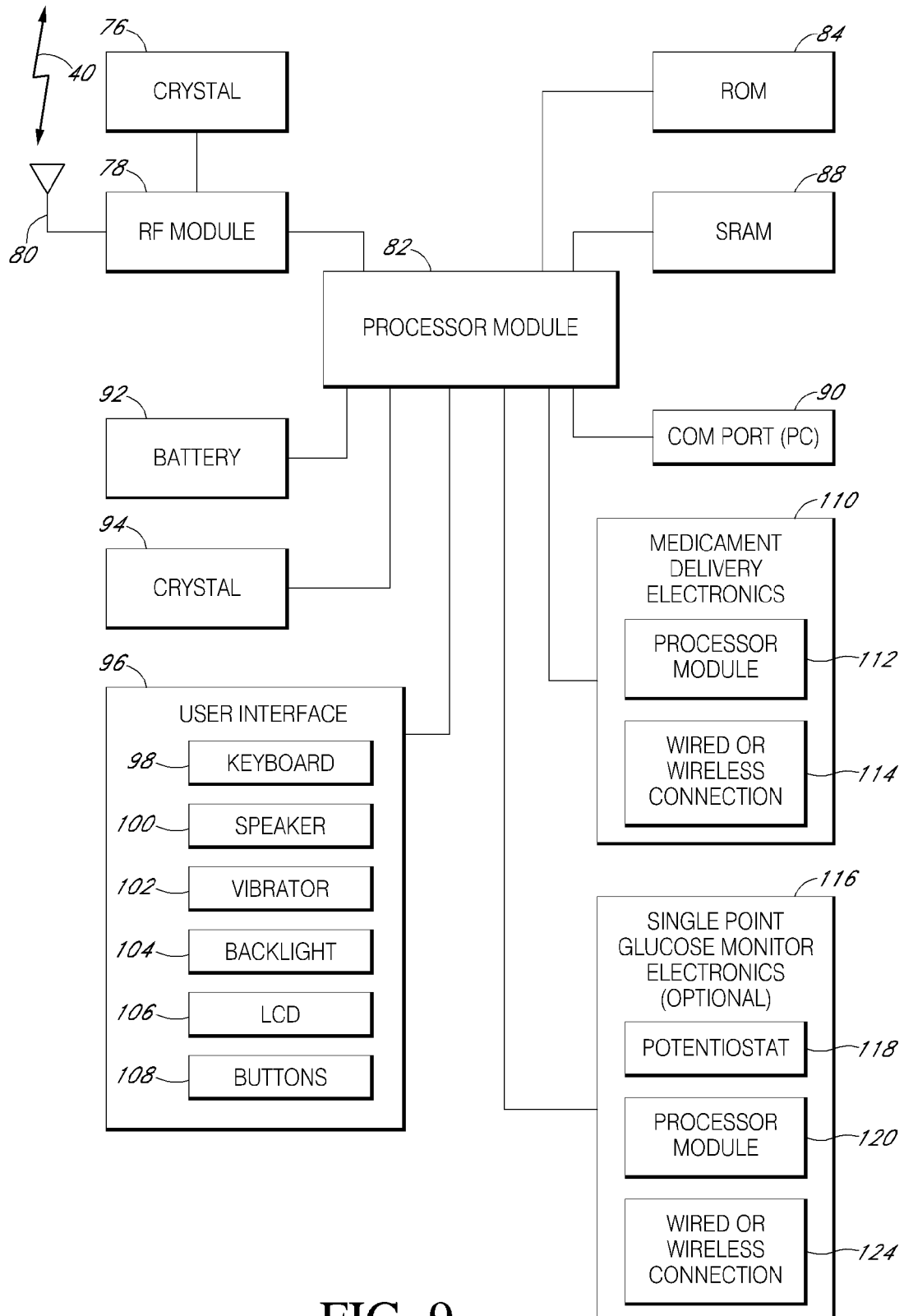
FIG. 9 is a block diagram that illustrates integrated system electronics in one embodiment.
Figure 10:
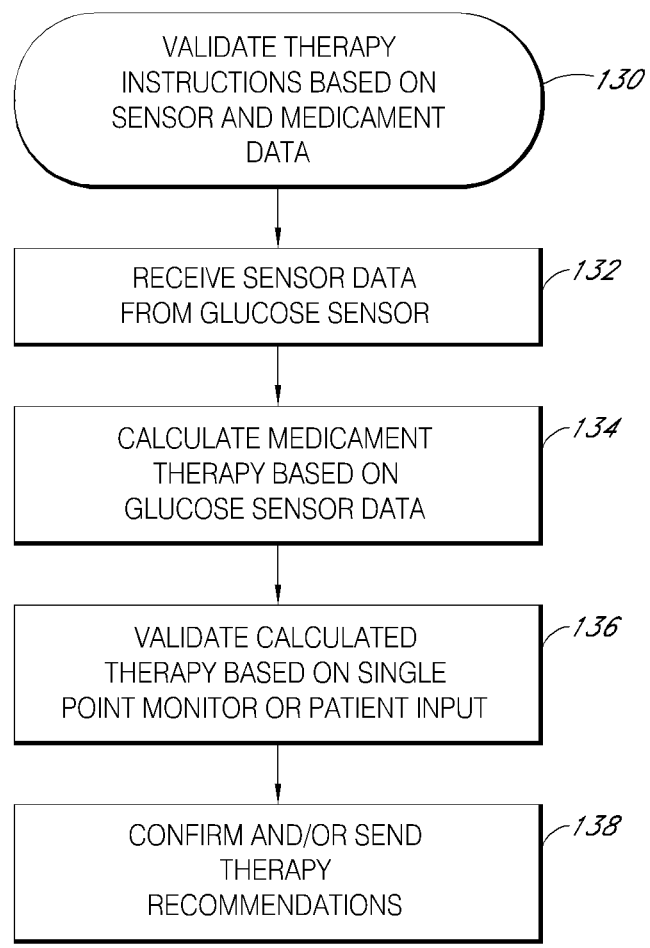
FIG. 10 is a flow chart that illustrates the process of validating therapy instructions prior to medicament delivery in one embodiment.
Figure 11:
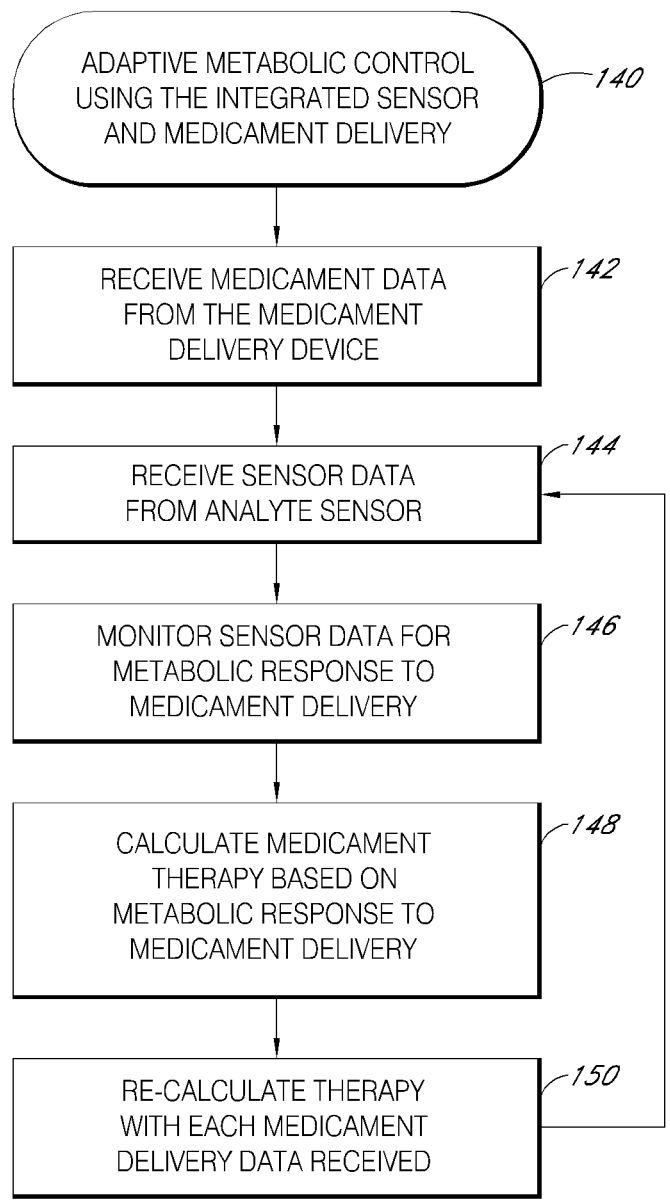
FIG. 11 is a flow chart that illustrates the process of providing adaptive metabolic control using an integrated sensor and medicament delivery device in one embodiment.

The preferred embodiments provide an integrated system, which includes a receiver 14 that receives and processes the raw data stream from the continuous glucose sensor 12. The receiver can perform all or some of the following operations: a calibration, converting sensor data, updating the calibration, evaluating received reference and sensor data, evaluating the calibration for the analyte sensor, validating received reference and sensor data, displaying a meaningful glucose value to a user, calculating therapy recommendations, validating recommended therapy, adaptive programming for learning individual metabolic patterns, and prediction of glucose values, for example. Some complementary systems and methods associated with the receiver are described in more detail with reference to U.S. Patent Publication No. US-2005-0027463-A1 which is incorporated herein by reference in its entirety. FIGS. 9 to 11 describe some processes that can be programmed into the receiver. Additionally, the receiver 14 of the preferred embodiments works together with the other components of the system (for example, the medicament delivery device 16 and the single point glucose monitor 18) to provide enhanced functionality, convenience, and safety, such as described in more detail herein. FIGS. 4 to 7 are illustrates of a few exemplary integrated systems of the preferred embodiments, each of which include the receiver, such as described in more detail herein.

In some embodiments, the receiver 14 is a PDA- or pager-sized housing 46, for example, and comprises a user interface 48 that has a plurality of buttons 50 and a liquid crystal display (LCD) screen, which can include a backlight. In some embodiments, the receiver can take other forms, for example a computer, server, or other such device capable of receiving and processing the data such as described herein. In some embodiments the user interface can also include a keyboard, a speaker, and a vibrator such as described with reference to FIG. 8. The receiver 46 comprises systems (for example, electronics) necessary to receive, process, and display sensor data from the glucose sensor 12, such as described in more detail with reference to FIG. 8. The receiver 14 processes data from the continuous glucose sensor 12 and additionally processes data associated with at least one of the medicament delivery device 16, single point glucose meter 16, and user 8.

In some embodiments, the receiver 14 is integrally formed with at least one of the medicament delivery device 16, and single point glucose monitor 18. In some embodiments, the receiver 14, medicament delivery device 16 and/or single point glucose monitor 18 are detachably connected, so that one or more of the components can be individually detached and attached at the user's convenience. In some embodiments, the receiver 14, medicament delivery device 16, and/or single point glucose monitor 18 are separate from, detachably connectable to, or integral with each other; and one or more of the components are operably connected through a wired or wireless connection, allowing data transfer and thus integration between the components. In some embodiments, one or more of the components are operably linked as described above, while another one or more components (for example, the syringe or patch) are provided as a physical part of the system for convenience to the user and as a reminder to enter data for manual integration of the component with the system. Some exemplary embodiments are described with reference to FIGS. 4 to 7, however suffice it to say that each of the components of the integrated system can be manually, semi-automatically, or automatically integrated with each other, and each component can be in physical and/or data communication with another component, which can include wireless connection, wired connection (for example, via cables or electrical contacts), or the like. In some embodiments, the receiver is configured to process data from the glucose sensor, an auxiliary sensor and/or the medicament delivery device, and can include a controller module.

Medicament Delivery Device

The preferred embodiments provide an integrated system 10, which includes a medicament delivery device 16 for administering a medicament to the host 8. The integrated medicament delivery device can be designed for bolus injection/infusion, basal injection/infusion, continuous injection/infusion, inhalation, transdermal absorption, other method for administering medicament, or any combinations thereof. In one exemplary embodiment, the medicament delivery device is an infusion pump configured for transcutaneous (e.g., injection/infusion and absorption into the subcutaneous tissue), intraperitoneal or intravenous infusion. In some embodiments, the infusion device is wholly implantable. In other embodiments, the infusion device is worn outside of the body, with infusion via a catheter. In some embodiments, the infusion device is configured for one or more maintenance functions, such as but not limited to checking for catheter clogs or monitoring the rate of insulin leaving the infusion device or the remaining volume of insulin within the pump. In some embodiments, the medicament delivery device is an insulin pump configured to deliver insulin to the host. In some embodiments, the insulin pump is further configured to receive and process instructions for delivery of an insulin therapy from a controller module.

In some embodiments, the medicament delivery device is an injection pen configured to inject insulin transcutaneously. In some embodiments, the medicament delivery device is an inhaler that delivers an inhalable insulin formulation. In other embodiments, the medicament delivery device is an oral medicament, such as an insulin preparation formulated for buccal absorption. In still other embodiments, the medicament delivery device is configured for transdermal delivery, such as a transdermal patch. In some embodiments, the at least two insulin delivery devices are used in conjunction with each other. For example, delivery of insulin by an infusion device (e.g., a pump) can be supplemented with delivery of another medicament (e.g., either the same or different types of insulin, or another medicament such as glucagon) with a second medicament delivery device, such as but not limited to a pen, a transdermal patch or an inhaler. For example, in some circumstances, a host can use an infusion pump to deliver rapid acting insulin and a patch to constantly deliver a slow-acting insulin. In another exemplary circumstance, a transcutaneous insulin pump can provide the insulin therapy, which can be supplemented by instructions to provide a therapeutic dose of glucagon via an inhaler or an oral preparation. The term medicament includes any substance used in therapy for a host using the system 10, for example, insulin, glucagon, or derivatives thereof. PCT International Publication No. WO02/43566-A1 describes glucose, glucagon, and vitamins A, C, or D that can be used with the preferred embodiments. U.S. Pat. Nos. 6,051,551 and 6,024,090 describe types of insulin suitable for inhalation that can be used with the preferred embodiments. U.S. Pat. Nos. 5,234,906, 6,319, 893, and European Patent No. EP-760677-B1 describe various derivatives of glucagon that can be used with the preferred embodiments. U.S. Pat. No. 6,653,332 describes a combination therapy that can be used with the preferred embodiments. U.S. Pat. No. 6,471,689 and PCT International Publication No. WO81/01794-A1 describe insulin useful for delivery pumps that can be used with the preferred embodiments. U.S. Pat. No. 5,226,895 describes a method of providing more than one type of insulin that can be used with the preferred embodiments. Each of the above references is incorporated herein by reference in its entirety and the medicaments and methods disclosed can be useful in the preferred embodiments.

As described elsewhere herein, in preferred embodiments, the system is configured to substantially mimic the body's metabolic response to changes in glucose (e.g., the host's blood sugar concentration), similar to the response of a pancreatic β-cell to changes in glucose concentration. As is understood by one skilled in the art, insulin activity can be influenced by a variety of factors, such as but not limited to method/location of delivery (e.g., injected transcutaneously, infused IV or intraperitoneally, inhaled, etc.), the host's insulin sensitivity, method of insulin preparation, and the like. However, it is possible to compare different insulins by comparing their time-activity profiles (TAP), as defined by methods of Frohnauer, et al. 2001, in "Graphical Human Insulin Time-Activity Profiles Using Standardized Definitions," *Diab. Tech. & Therap.* 3(3):419-429. Table 1 presents the TAPs of some purified human insulins (e.g., wild type and/or analogs) and one exemplary flash insulin (described elsewhere herein).

glucose clamp studies (e.g., on human volunteers) and examining the pharmacokinetics of the insulin (e.g., by examining the plasma insulin level or the glucose infusion rate during glucose clamp studies). According to the methods of Frohnauer, et al., "onset" of an insulin's activity can be determined by graphing the insulin's activity over an extended period of time (e.g., about 24- to 38-hours). On a graph of an insulin's activity (see FIG. 4), onset occurs at a time point between last baseline measurement and the first measurement above the baseline. In some circumstances, onset of an insulin's activity can be very abrupt or sharp, occurring within a few minutes. In other circumstances, onset can be prolonged, taking up to several hours. The peak of insulin activity occurs at a time point between the first maximum activity measurement and the last maximum activity measurement. In some circumstances, the peak of activity is very brief, such as a single time point. In other circumstances, the peak is prolonged (e.g., lasts a period of minutes or hours) and falls within a range of consecutive time points. The duration of an insulin's activity is the length of time during which the insulin has been active (e.g., functioning, working in the body), up to the termination of activity. At termination, the insulin's activity generally declines, tapers off and/or plateau's out (e.g., flattens out). On a graph of the insulin's activity, activity termination occurs between the last point above horizontal and the first point on the horizontal. In some circumstances, an insulin's termination can be abrupt, such as at a single point. In other circumstances, an insulin's termination can be extended over a period of several minutes or a few hours.

TABLE 1

| Insulin Formulation | Onset (hrs) | $T_{i50}$ (hrs) | Peak (hrs) | $T_{d50}$ (hrs) | Duration (hrs) |
|---|---|---|---|---|---|
| Humulin R | | | | | |
| Plasma Insulin Level | 0.08-1.0 | | 0.5-3.25 | | 4.0-12.0 |
| Glucose Infusion Rate | 0.25-1.0 | 0.6-1.25 | 1.5-4.0 | 4.0-7.0 | 9.5-12.0 |
| NPH | | | | | |
| Plasma Insulin Level | 0.08-1.5 | | 1.0-8.0 | | 6.0-28.0 |
| Glucose Infusion Rate | 0.25-2.0 | 1.25-3.25 | 3.5-10.0 | 8.5-18.0 | 14.0-27.0 |
| Lente | | | | | |
| Plasma Insulin Level | 0.5-2.25 | | 4.0-6.5 | | 21.0-24.0 |
| Glucose Infusion Rate | 0.75-2.0 | 3.0-4.5 | 9.4-12.0 | 19.25-23.5 | 21.0-24.0 |
| Ultralente | | | | | |
| Plasma Insulin Level | 0.5-3.0 | | 4.0-16.0 | | 9.0-28.0 |
| Glucose Infusion Rate | 0.75-3.0 | 3.5-8.0 | 5.0-14.5 | 17.0-22.0 | 22.5-36.6 |
| Insulin lispro | | | | | |
| Plasma Insulin Level | 0.08-0.25 | | 0.6-1.0 | | 3.0-8.0 |
| Glucose Infusion Rate | 0.16-0.5 | 0.6-0.75 | 1.25-2.0 | 2.5-4.25 | 5.0-7.0 |
| Flash Insulin | | | | | |
| Plasma Insulin Level | ≤0.08-≤0.25 | | ≤0.6-≤1.0 | | ≤3.0-≤8.0 |
| Glucose Infusion Rate | ≤0.25-≤0.5 | ≤0.6-≤0.75 | ≤1.25-≤2.0 | ≤2.5-≤4.25 | ≤5.0-≤7.0 |

Humulin R = a purified wild type human insulin; NPH = a purified human insulin analog (Humulin N)
Lente = another purified human insulin analog (Humulin L)
Ultralente = yet another purified human insulin analog (Humulin U)
$T_{i50}$ = the time point at which insulin activity is half of the maximal activity, as the level increases.
$T_{d50}$ = the time point at which the insulin activity is half of the maximal activity, as the level decreases.

Figure 4:
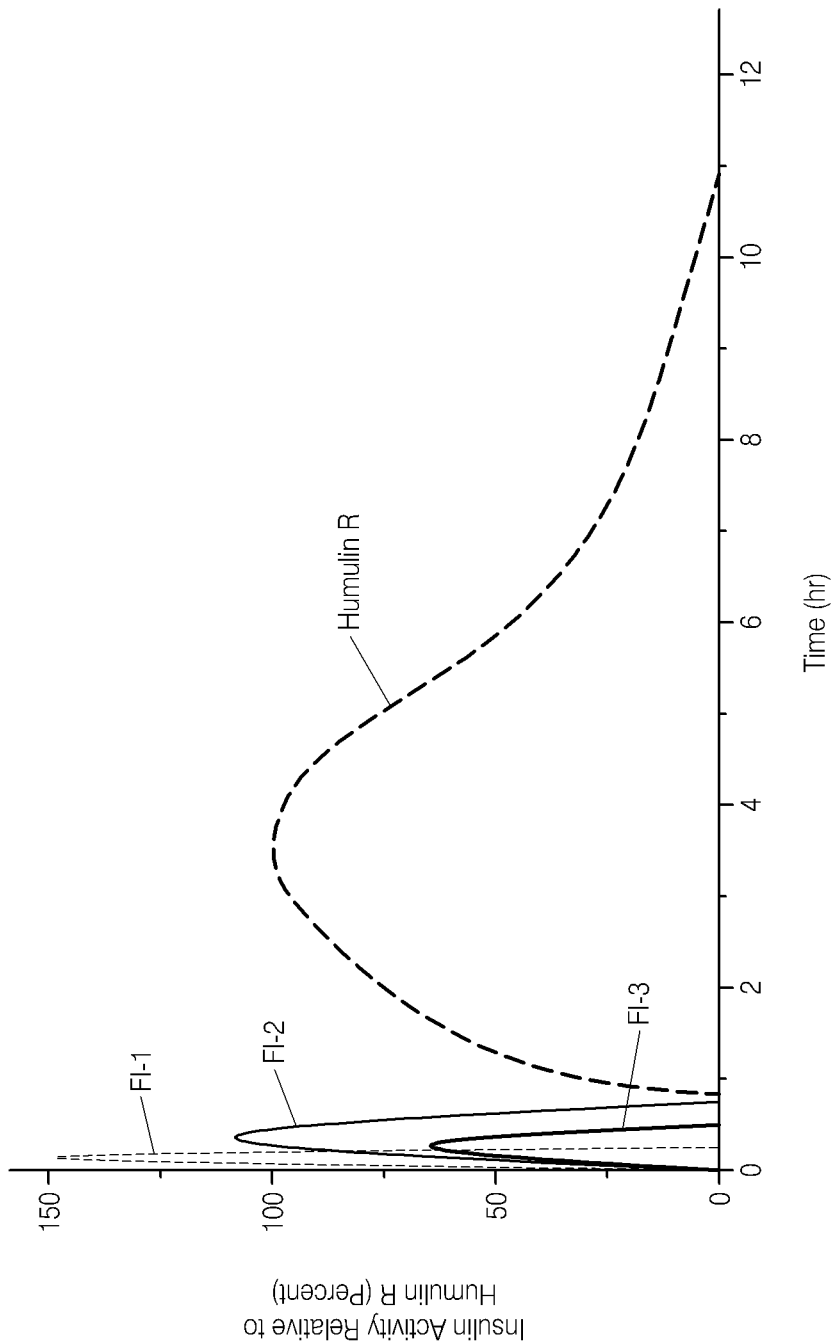
FIG. 4 is a graph comparing the time-activity profiles of some exemplary flash insulins (FI-1, FI2, FI3) to the time-activity profile of Humulin R, as taken from Frohnauer, et al. 2001, in "Graphical Human Insulin Time-Activity Profiles Using Standardized Definitions," *Diab. Tech. & Therap.* 3(3):419-429.

FIG. 4 illustrates the TAP of Humulin R (according to Frohnauer, et al. 2001, in "Graphical Human Insulin Time-Activity Profiles Using Standardized Definitions," *Diab. Tech. & Therap.* 3(3):419-429) and three possible TAPs for a "Flash Insulin," which is described below. As is known to those skilled in the art, the times of onset, peak and duration of an insulin's activity can be determined by conducting In some embodiments, the insulin used in conjunction with the integrated system 10 is configured such that the system mimics the function of a pancreatic β-cell, with a substantially immediate onset of activity, a very rapid peak and a very brief duration (as determined by plasma insulin concentration according to the methods of Frohnauer et al). In some embodiments, the insulin is configured to have an onset time of about 5-minutes to about 10-minutes or less and a peak of activity of about 5-minutes to about 1.25-hours. Additionally, the insulin is configured to have a substantially short (e.g., brief) duration of about 3-hours or less.

In some embodiments, a very rapid-acting insulin is preferred, such that the insulin can be delivered by a system having an on/off controller, as described elsewhere herein. Such an insulin is referred to herein as a "Flash Insulin." In FIG. 4, three possible TAPs, of an exemplary flash insulin, are denoted by the curves labeled FI-1, FI-2 and FI-3. Depending upon the flash insulin developed, other TAPs are possible. In preferred embodiments, a flash insulin is configured to have a substantially "instant on" onset, such that the flash insulin reaches its peak of activity within a short time after delivery. For example, in some embodiments, a flash insulin's onset can occur within about 10-minutes or less (e.g., after delivery), preferably within about 6-minutes or less. In another example, in some embodiments, the flash insulin's peak of activity can occur within about 2-minutes to about 30-minutes, preferably within about 5-minutes to about 15-minutes. In another example, in some embodiments, the flash insulin's duration is substantially short, such as less than about 3, 2 or 1-hours. In some preferred embodiments, the flash insulin's activity peaks within about 4, 5, 8, 10, 15 or 20-minutes of the insulin's onset of activity and/or infusion of the insulin into the host. In some more preferred embodiments, the flash insulin's duration is sufficiently brief that "dose stacking" (e.g., from sequential doses) has substantially no effect on the host's glucose concentration. For example, in some embodiments, the flash insulin's duration is about 10, 20, 30 or 40-minutes, preferably less than about 20-minutes. In some embodiments, the flash insulin is configured for use with an on/off controller (discussed elsewhere herein), such that when the on instruction is selected, the flash insulin is delivered at substantially constant rate.

Manual Integration

In some embodiments, the medicament delivery device 16 is a manual delivery device, for example a syringe, inhaler, transdermal patch, cell transplantation device, and/or manual pump for manual integration with the receiver. Manual integration includes medicament delivery devices wherein a user (for example, host or doctor) manually selects the amount, type, and/or time of delivery. In some embodiments, the medicament delivery device 16 is any syringe suitable for injecting a medicament, as is appreciated by one skilled in the art. One example of a syringe suitable for the medicament delivery device of the preferred embodiments is described in U.S. Pat. No. 5,137,511, which is incorporated herein by reference in its entirety.

Figure 5A:
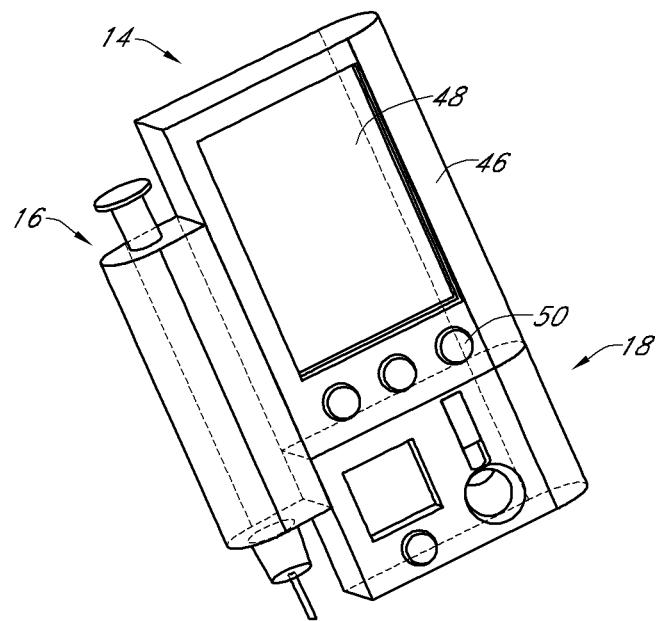
FIGS. 5A and 5B are perspective views of an integrated system 10 in one embodiment, wherein a receiver is integrated with a medicament delivery device in the form of a manual syringe, and optionally includes a single point glucose monitor.
Figure 5B:
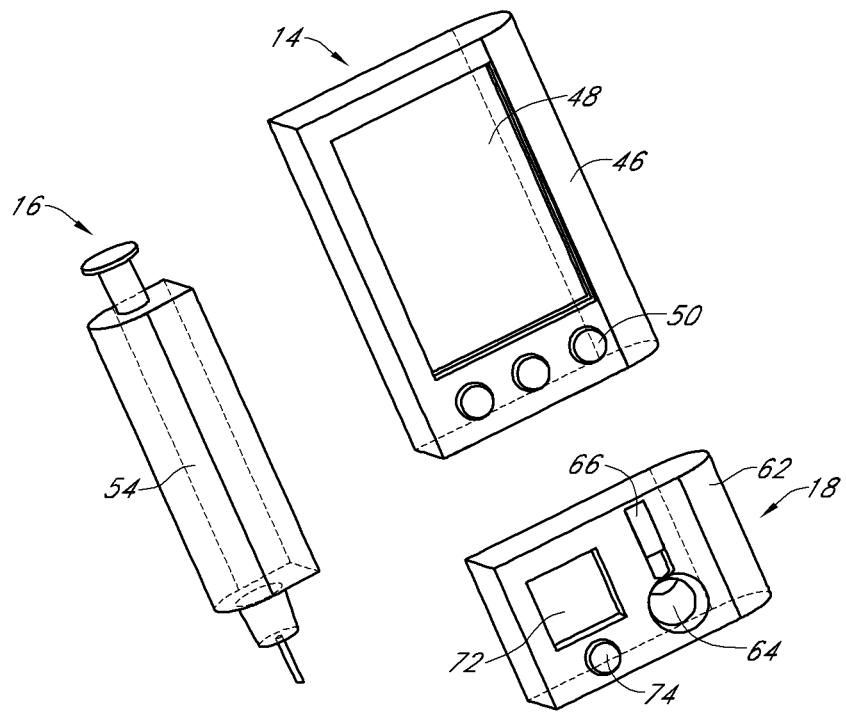

FIGS. 5A and 5B are perspective views of an integrated system 10 in one embodiment, wherein a receiver 14 is integrated with a medicament delivery device 16 in the form of a manual syringe 54, and optionally includes a single point glucose monitor 18, which will be described in more detail elsewhere herein. The receiver 14 receives, processes, and displays data from the continuous glucose monitor 12, such as described in more detail above, and can also receive, process, and display data manually entered by the user. In some embodiments, the receiver includes algorithms that use parameters provided by the continuous glucose sensor, such as glucose concentration, rate-of-change of the glucose concentration, and acceleration of the glucose concentration to more particularly determine the type, amount, and time of medicament administration. The medicament delivery device 16 is in the form of a syringe 54, which can comprise any known syringe configuration, such as described in more detail above. In some embodiments, the syringe 54 includes a housing, which is designed to hold a syringe as well as a plurality of types and amounts of medicament, for example fast-acting insulin, slow-acting insulin, and glucagon. In some embodiments, the syringe is detachably connectable to the receiver 14, and the receiver 14 provides and receives information to and from the host associated with the time, type, and amount of medicament administered. In some embodiments, the syringe is stored in a holder that is integral with or detachably connected to the receiver 14. In some embodiments, the syringe 54 can be detachable connected directly to the receiver, provided in a kit with the receiver, or other configuration, which provides easy association between the syringe and the receiver.

Referring now to the integration between the syringe and the receiver, it is noted that the receiver can be programmed with information about the time, amount, and types of medicament that can be administered with the syringe, for example. In some embodiments during set-up of the system, the host and/or doctor manually enters information about the amounts and types of medicament available via the syringe of the integrated system. In some alternative embodiments, manufacturer-provided data can be downloaded to the receiver so that the host and/or doctor can select appropriate information from menus on the screen, for example, to provide easy and accurate data entry. Thus, by knowing the available medicaments, the receiver can be programmed to customize the host's therapy recommendations considering available types and amounts of medicaments in combination with concentration, rate-of-change, and/or acceleration of the host's glucose. While not wishing to be bound by theory, it is believed that by storing available medicament therapies, the receiver is able to customize medicament calculations and recommend appropriate therapy based glucose on trend information and the preferred types and the amounts of medicament available to the host.

Subsequently in some embodiments, once the host has administered a medicament (including via the syringe and or by other means), the amount, type, and/or time of medicament administration are input into the receiver by the host. Similarly, the receiver can be programmed with standard medicaments and dosages for easy selection by the host (for example, menus on the user interface). This information can be used by the receiver to increase the intelligence of the algorithms used in determining the glucose trends and patterns that can be useful in predicting and analyzing present, past, and future glucose trends, and in providing therapy recommendations, which will be described in more detail below. Additionally, by continuously monitoring the glucose concentration over time, the receiver provides valuable information about how a host responds to a particular medicament, which information can be used by a doctor, host, or by the algorithms within the receiver, to determine patterns and provide more personalized therapy recommendations. In other words, in some embodiments, the receiver includes programming that learns the patterns (for example, an individual's metabolic response to certain medicament deliveries and host behavior) and to determine an optimum time, amount, and type of medicament to delivery in a variety of conditions (e.g., glucose concentration, rate-of-change, and acceleration). While not wishing to be bound by theory, it is believed that by continuously monitoring an individual's response to various medicaments, the host's glucose levels can be more proactively treated, keeping the diabetic host within safe glucose ranges substantially all the time.

In some embodiments, the receiver includes programming to predict glucose trends, such as described in U.S. Patent Publication No. US-2005-0203360-A1, which is incorporated herein by reference in its entirety. In some embodiments, the predictive algorithms consider the amount, type, and time of medicament delivery in predicting glucose values. For example, a predictive algorithm that predicts a glucose value or trend for the upcoming 15 to 20 minutes uses a mathematical algorithm (for example, regression, smoothing, or the like) such as described in the above-cited U.S. Patent Publication No. US-2005-0203360-A1 to project a glucose value. However outside influences, including medicament delivery can cause this projection to be inaccurate. Therefore, some embodiments provide programming in the receiver that uses the medicament delivery information received from the delivery device 14, in addition to other mathematical equations, to more accurately predict glucose values in the future.

In some alternative embodiments, the medicament delivery device 16 includes one or more transdermal patches 58 suitable for administering medicaments as is appreciated by one skilled in the art. PCT International Publication No. WO02/43566 describes one such transdermal patch, which can be used in the preferred embodiments. Although the above-cited reference and description associated with the FIGS. 6A to 6C describe a medicament (for example, glucagon) useful for treating hypoglycemia, it is understood that transdermal patches that release a medicament (for example, insulin) useful for treating hyperglycemia are also contemplated within the scope of the preferred embodiments.

Figure 6A:
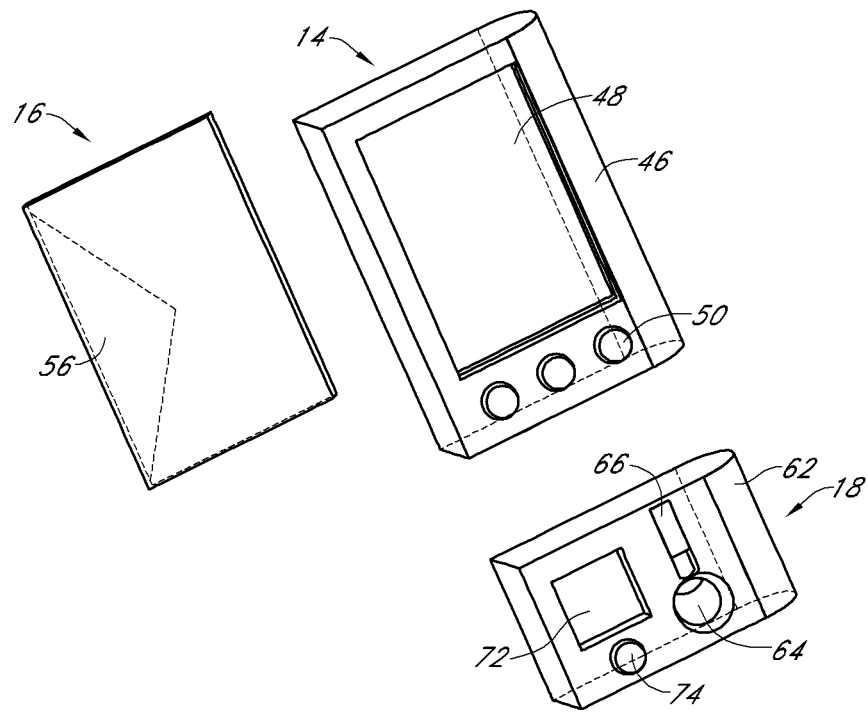
FIGS. 6A to 6C are perspective views of an integrated system in one embodiment, wherein a receiver is integrated with a medicament delivery device in the form of one or more transdermal patches housed within a holder, and optionally includes a single point glucose monitor.
Figure 6B:
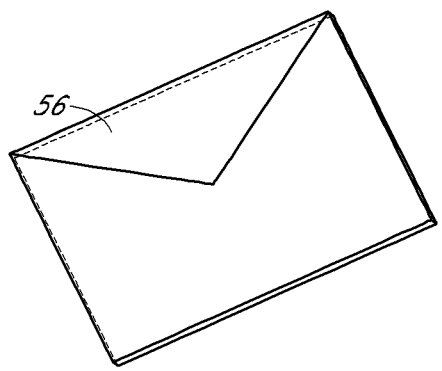
Figure 6C:
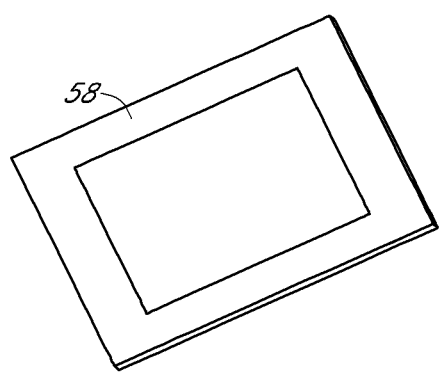

FIGS. 6A to 6C are perspective views of an integrated system 10 in one embodiment, wherein a receiver 14 is integrated with a medicament delivery device 16 in the form of one or more transdermal patches 58 housed within a holder 56, and optionally includes a single point glucose monitor 18, which will be described in more detail elsewhere herein. The receiver 14 receives, processes, and displays data from the continuous glucose monitor 12, such as described in more detail above. The medicament delivery device 16 is in the form of one or more transdermal patches 58 held in a holder 56, which can comprise any known patch configuration.

The integration of the patches 58 with the receiver 14 includes similar functionality and provides similar advantages as described with reference to other manual integrations including manual medicament delivery devices (for example, syringe and inhaler). However, a unique advantage can be seen in the integration of a continuous glucose sensor with a glucagon-type patch. Namely, a continuous glucose sensor, such as described in the preferred embodiments, provides more than single point glucose readings. In fact, because the continuous glucose sensor 12 knows the concentration, rate-of-change, acceleration, the amount of insulin administered (in some embodiments), and/or individual patterns associated with a host's glucose trends (learned over time as described in more detail elsewhere herein), the use of the glucagon patch can be iteratively optimized (inputting its usage into the receiver and monitoring the individual's metabolic response) to proactively preempt hypoglycemic events and maintain a more controlled range of glucose values. This can be particularly advantageous for nighttime hypoglycemia by enabling the diabetic host (and his/her caretakers) to improve overall nighttime diabetic health. While not wishing to be bound by theory, the integration of the continuous glucose sensor and transdermal glucagon-type patch can provide diabetic hosts with a long-term solution to reduce or avoid hypoglycemic events.

In some embodiments, the holder 58 is detachably connectable to the receiver 14 (for example on the side opposite the LCD), which enables convenient availability of the patch to the host when the receiver indicates that a medicament (for example, glucose or glucagon) is recommended. It is further noted that although this holder is shown without another medicament delivery device 16 in the illustrations of FIGS. 6A to 6C, other medicaments (for example, insulin pen, insulin pump, such as described with reference to FIGS. 7 and 8) can be integrated into the system in combination with the medicament patch illustrated herein. While not wishing to be bound by theory, it is believed that by combining medicaments that aid the diabetic host in different ways (for example, medicaments for treating hyper- and hypo-glycemic events, or, fast-acting and slow-acting medicaments), a simplified comprehensive solution for treating diabetes can be provided.

Manual integration of delivery devices with the continuous glucose sensor 12 of the preferred embodiments can additionally be advantageous because the continuous device of the preferred embodiments is able to track glucose levels long-term (for example weeks to months) and adaptively improve therapy decisions based on the host's response over time.

In some alternative embodiments, the medicament delivery device 16 includes an inhaler or spray device suitable for administering a medicament into the circulatory system, as is appreciated by one skilled in the art. Some examples of inhalers suitable for use with the preferred embodiments include U.S. Pat. Nos. 6,167,880, 6,051,551, and 6,024,090, which are incorporated herein by reference in their entirety. In some embodiments, the inhaler or spray device is considered a manual medicament delivery device, such as described with reference to FIGS. 5 and 6, wherein the inhaler or spray is manually administered by a host, and wherein the host manually enters data into the continuous receiver about the time, amount, and types of therapy. However, it is also possible that the inhaler or spray device used for administering the medicament can also comprise a processor module and operable connection to the receiver (for example, RF), such that data is sent and received between the receiver and inhaler or spray device, making it a semi-automated integration, which is described in more detail with reference to the integrated insulin pen below, for example.

In some embodiments, the inhaler or spray device is integrally housed within, detachably connected to, or otherwise physically associated with (for example, in a kit) to the receiver. The functionality and advantages of the integrated inhaler or spray device are similar to those described with reference to the syringe and/or patch integration, above. It is noted that the inhaler or spray device can be provided in combination with any other of the medicament delivery devices of the preferred embodiments, for example, a fast-acting insulin inhaler and a slow acting insulin pump can be advantageously integrated into the system of the preferred embodiments and utilized at the appropriate time as is appreciated by one skilled in the art. In some embodiments, wherein the inhaler or spray device includes a semi-automated integration with the receiver, the inhaler or spray device can by physically integrated with receiver such as described above and also operably connected to the receiver, for example via a wired (for example, via electrical contacts) or wireless (for example, via RF) connection.

In one alternative embodiment, a manual medicament delivery pump is implanted such as described in U.S. Pat. No. 6,283,944, which is incorporated herein by reference in its entirety. In this alternative embodiment, the host-controlled implantable pump allows the host to press on the device (through the skin) to administer a bolus injection of a medicament when needed. It is believed that providing glucagon or other medicament for treating hypoglycemia within this device will provide the ease and convenience that can be easily released by the host and/or his or her caretaker when the continuous glucose sensor indicates severe hypoglycemia, for example. In some alternative embodiments, the manual implantable pump is filled with insulin, or other medicament for treating hyperglycemia. In either case, the manual pump and continuous glucose sensor will benefit from manual integrations described in more detail above.

In another alternative embodiment, a cell transplantation device, such as described in U.S. Pat. Nos. 6,015,572, 5,964,745, and 6,083,523, which are incorporated herein by reference in their entirety, is manually integrated with the continuous sensor of the preferred embodiments. In this alternative embodiment, a host would be implanted with beta islet cells, which provide insulin secretion responsive to glucose levels in the body. The receiver associated with the implantable glucose sensor can be programmed with information about the cell transplantation (for example, time, amount, type, etc). In this way, the long-term continuous glucose sensor can be used to monitor the body's response to the beta islet cells. This can be particularly advantageous when a host has been using the continuous glucose sensor for some amount of time prior to the cell transplantation, and the change in the individual's metabolic patterns associated with the transplantation of the cells can be monitored and quantified. Because of the long-term continuous nature of the glucose sensor of the preferred embodiments, the long-term continuous effects of the cell transplantation can be consistently and reliably monitored. This integration can be advantageous to monitor any person's response to cell transplantation before and/or after the implantation of the cells, which can be helpful in providing data to justify the implantation of islet cells in the treatment of diabetes.

It is noted that any of the manual medicament delivery devices can be provided with an RF ID tag or other communication-type device, which allows semi-automated integration with that manual delivery device, such as described in more detail below.

Semi-Automated Integration

Semi-automated integration of medicament delivery devices 16 in the preferred embodiments includes any integration wherein an operable connection between the integrated components aids the user (for example, host or doctor) in selecting, inputting, or calculating the amount, type, or time of medicament delivery of glucose values, for example, by transmitting data to another component and thereby reducing the amount of user input required. In the preferred embodiments, semi-automated can also refer to a fully automated device (for example, one that does not require user interaction), wherein the fully automated device requires a validation or other user interaction, for example to validate or confirm medicament delivery amounts. In some embodiments, the semi-automated medicament delivery device is an inhaler or spray device, a pen or jet-type injector, or a transdermal or implantable pump.

Figure 7A:
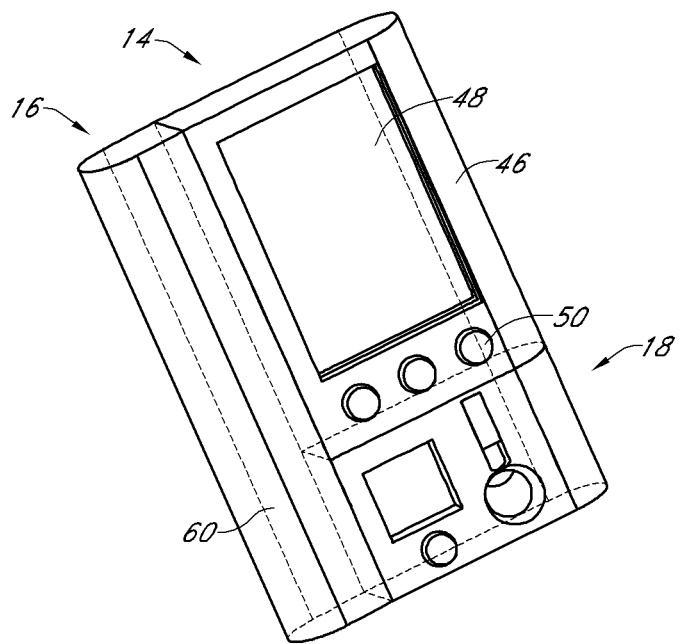
FIGS. 7A and 7B are perspective views of an integrated system in one embodiment, wherein a receiver is integrated with a medicament delivery device in the form of a pen or jet-type injector, and optionally includes a single point glucose monitor.
Figure 7B:
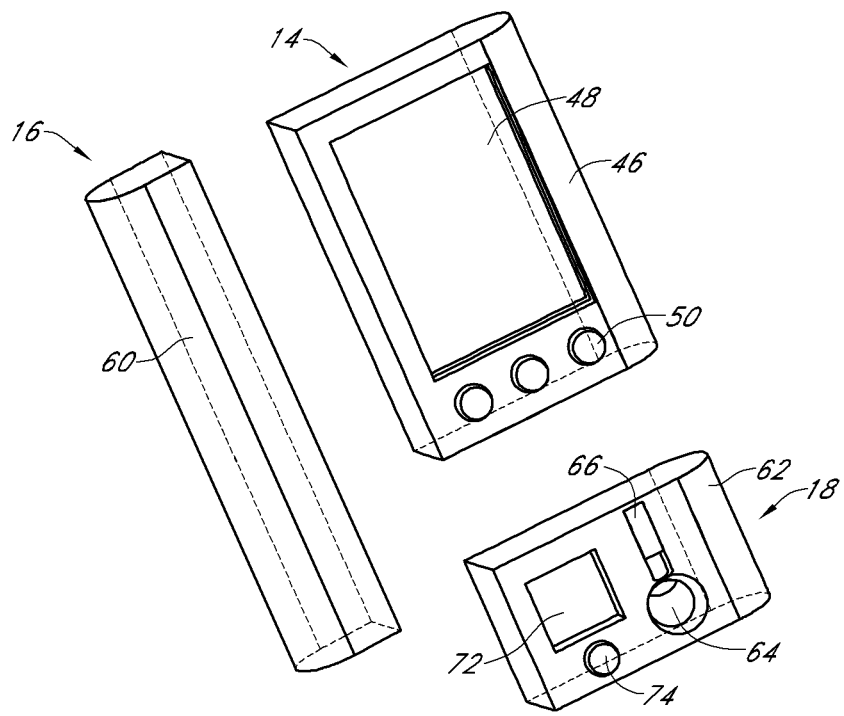

FIGS. 7A and 7B are perspective views of an integrated system 10 in one embodiment, wherein a receiver 14 is integrated with a medicament delivery device 16 in the form of a pen or jet-type injector, hereinafter referred to as a pen 60, and optionally includes a single point glucose monitor 18, which will be described in more detail elsewhere herein. The receiver 14 receives, processes, and displays data from the continuous glucose monitor 12, such as described in more detail above. The medicament delivery pen 60 of the preferred embodiments includes any pen-type injector, such as is appreciated by one skilled in the art. A few examples of medicament pens that can be used with the preferred embodiments, include U.S. Pat. Nos. 5,226,895, 4,865,591, 6,192,891, and 5,536,249, each of which are incorporated herein by reference in its entirety.

FIG. 7A is a perspective view of an integrated system 10 in embodiment. The integrated system 10 is shown in an attached state, wherein the various elements are held by a mechanical means, as is appreciated by one skilled in the art. The components 14, 16, and 18 (optional) are also in operable connection with each other, which can include a wired or wireless connection. In some embodiments, the components include electrical contacts that operably connect the components together when in the attached state. In some embodiments, the components are operably connected via wireless connection (for example, RF), and wherein the components may or may not be detachably connectable to each other. FIG. 7B shows the components in an unattached state, which can be useful when the host would like to carry minimal components and/or when the components are integrated via a wireless connection, for example.

Medicament delivery pen 60 includes at least a processor module and a wired or wireless connection to the receiver 14, which are described in more detail with reference to FIG. 9. In some embodiments, the pen 60 includes programming that receives instructions sent from the receiver 14 regarding type and amount of medicament to administer. In some embodiments, wherein the pen includes more than one type of medicament, the receiver provides the necessary instructions to determine which type or types of medicament to administer, and can provide instructions necessary for mixing the one or more medicaments. In some embodiments, the receiver provides the glucose trend information (for example, concentration, rate-of-change, acceleration, or other user input information) and pen 60 includes programming necessary to determine appropriate medicament delivery.

Subsequently, the pen 60 includes programming to send information regarding the amount, type, and time of medicament delivery to the receiver 14 for processing. The receiver 14 can use this information received from the pen 60, in combination with the continuous glucose data obtained from the sensor, to monitor and determine the host's glucose patterns to measure their response to each medicament delivery. Knowing the host's individual response to each type and amount of medicament delivery can be useful in adjusting or optimizing the host's therapy. It is noted that individual metabolic profiles (for example, insulin sensitivity) are variable from host to host. While not wishing to be bound by theory, it is believed that once the receiver has learned (for example, monitored and determined) the individual's metabolic patterns, including glucose trends and associated medicament deliveries, the receiver can be programmed to adjust and optimize the therapy recommendations for the host's individual physiology to maintain their glucose levels within a desired target range. In alternative embodiments, the pen 60 can be manually integrated with the receiver.

In some embodiments, the receiver includes algorithms that use parameters (e.g., data) provided by the continuous glucose sensor, such as glucose concentration, rate-ofchange of the glucose concentration, and acceleration of the glucose concentration to more particularly determine the type, amount, and time of medicament administration. In fact, all of the functionality of the above-described manual and semi-automated integrated systems, including therapy recommendations, adaptive programming for learning individual metabolic patterns, and prediction of glucose values, can be applied to the semi-automated integrated system 10, such as described herein. However, the semi-automated integrated sensing and delivery system additionally provides convenience by automation (for example, data transfer through operable connection) and reduced opportunity for human error than can be experienced with the manual integration.

In some alternative embodiments, the semi-automated integration provides programming that requires at least one of the receiver 14, single point glucose monitor 18, and medicament delivery device 16 to be validated or confirmed by another of the components to provide a fail safe accuracy check; in these embodiments, the validation includes algorithms programmed into any one or more of the components. In some alternative embodiments, the semi-automated integration provides programming that requires at least one of the receiver 14 and medicament delivery device 16 to be validated or confirmed by an a human (for example, confirm the amount and/or type of medicament). In these embodiments, validation provides a means by which the receiver can be used adjunctively, when the host or doctor would like to have more control over the host's therapy decisions, for example. See FIGS. 10 to 12 for processes that can be implemented herein.

Although the above description of semi-automated medicament delivery is mostly directed to an integrated delivery pen, the same or similar integration can be accomplished between a semi-automated inhaler or spray device, and/or a semi-automated transdermal or implantable pump device. Additionally, any combination of the above semi-automated medicament delivery devices can be combined with other manual and/or automated medicament delivery device within the scope of the preferred embodiments as is appreciated by one skilled in the art.

In some embodiments, the semi-automated integrated system 10 includes a dynamic bolus controller module that is configured to intelligently evaluate an engaged (e.g., selectable) bolus constraint (e.g., pre-set and/or programmable) and internally derived data, and to calculate an insulin therapy (e.g., dose) less than or equal to the maximum total insulin dose associated with the engaged bolus constraint, in response to the host engaging the bolus constraint, such as described in more detail elsewhere herein. Preferably, the determination of the insulin therapy is based solely on the internally derived data and the engaged bolus constraint. In some preferred embodiments, the evaluation and/or calculation of therapy are performed iteratively. In some embodiments, a bolus constraint can be engaged (e.g., selected, initiated, activated) by pressing a programmable button or key, actuating a switch, selecting from a menu (e.g., scroll, pop-up or tab) and the like. In some embodiments, the system includes two or more bolus constraints, such as constraints associated with different types of meals and/or with different events. For example, one or more bolus constraint buttons can be programmed by the user (e.g., the host or a caretaker of the host) for insulin therapies sufficient to cover an average breakfast, lunch or dinner, to cover a high carbohydrate or high fat meal, or as a corrective insulin dose and the like. In a further embodiment, the system is configured to request host validation of the calculated bolus insulin therapy (e.g., by selecting yes or no, OK).

In some embodiments, the system is configured to include an on/off controller module and/or a dynamic basal controller module. On/off and dynamic basal controller modules are discussed in detail elsewhere herein.

Automated Integration

Automated integration medicament delivery devices 16 in the preferred embodiments are any delivery devices wherein an operable connection between the integrated components provides for full control of the system without required user interaction. Transdermal and implantable pumps are examples of medicament delivery devices that can be used with the preferred embodiments of the integrated system 10 to provide automated control of the medicament delivery device 16 and continuous glucose sensor 12. Some examples of medicament pumps that can be used with the preferred embodiments include, U.S. Pat. No. 6,471,689, PCT International Publication No. WO81/01794, and European Patent No. EP-1281351-B, each of which is incorporated herein by reference in its entirety.

Figure 8A:
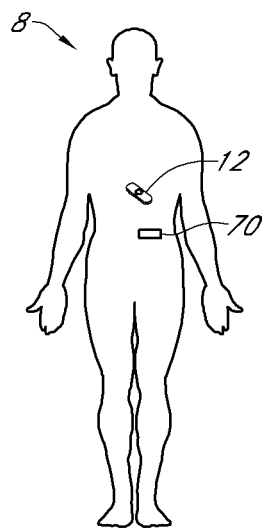
FIGS. 8A to 8C are perspective views of an integrated system in one embodiment, wherein a sensor and delivery pump, which are implanted or transdermally inserted into the patient, are operably connected to an integrated receiver, and optionally include a single point glucose monitor.
Figure 8B:
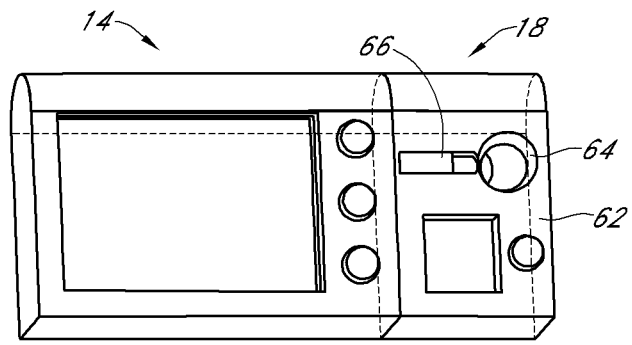
Figure 8C:
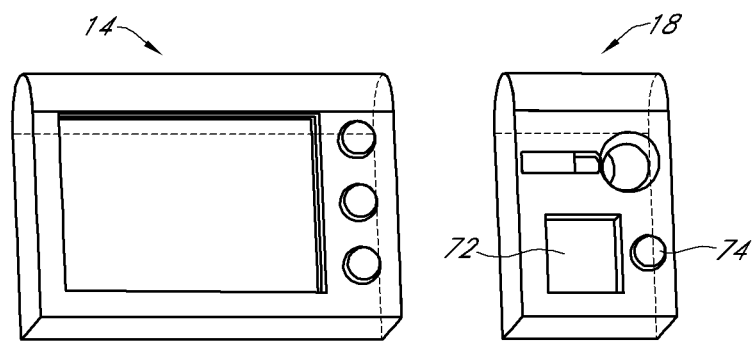

FIGS. 8A to 8C are perspective views of an integrated system in one embodiment, wherein a sensor and delivery pump, which are implanted or transdermally inserted into the host, are operably connected to an integrated receiver, and optionally include a single point glucose monitor. FIG. 8A is a perspective view of a host 8, in which is implanted or transdermally inserted a sensor 12 and a pump 70. FIGS. 8B and 8C are perspective views of the integrated receiver and optional single point glucose monitor in attached and unattached states. The pump 70 can be of any configuration known in the art, for example, such as cited above.

The receiver 14 receives, processes, and displays data associated with the continuous glucose monitor 12, data associated with the pump 70, and data manually entered by the host 8. In some embodiments, the receiver includes algorithms that use parameters provided by the continuous glucose sensor, such as glucose concentration, rate-of-change of the glucose concentration, and acceleration of the glucose concentration to determine the type, amount, and time of medicament administration. In fact, all of the functionality of the above-described manual and semi-automated integrated systems, including therapy recommendations, confirmation or validation of medicament delivery, adaptive programming for learning individual metabolic patterns, and prediction of glucose values, can be applied to the fully automated integrated system 10, such as described herein with reference to FIGS. 8A to 8C. However, the fully automated sensing and delivery system can run with or without user interaction. U.S. Patent Publication No. US-2003-0028089-A1 provides some systems and methods for providing control of insulin, which can be used with the preferred embodiments, and is incorporated herein by reference in its entirety.

In some embodiments of the automated integrated system 10, a fail-safe mode is provided, wherein the system is programmed with conditions whereby when anomalies or potentially clinically risky situations arise, for example when a reference glucose value (for example, from an SMBG) indicates a discrepancy from the continuous sensor that could cause risk to the host if incorrect therapy is administered. Another example of a situation that may benefit from a validation includes when a glucose values are showing a trend in a first direction that shows a possibility of "turn around," namely, the host may be able to reverse the trend with a particular behavior within a few minutes to an hour, for example. In such situations, the automated system can be programmed to revert to a semi-automated system requiring user validation or other user interaction to validate the therapy in view of the situation.

It is noted that in the illustrated embodiment, only one receiver 14 is shown, which houses the electronics for both the medicament delivery pump 70 and the continuous sensor 12. Although it is possible to house the electronics in two different receiver housings, providing one integrated housing 14 increases host convenience and minimizes confusion or errors. In some embodiments, the sensor receiver electronics and pump electronics are separate, but integrated. In some alternative embodiments, the sensor and pump share the same electronics.

Additionally, the integrated receiver for the sensor and pump, can be further integrated with any combination with the above-described integrated medicament delivery devices, including syringe, patch, inhaler, and pen, as is appreciated by one skilled in the art.

In some embodiments, the fully automated integrated system 10 includes an on/off controller module, as described elsewhere herein. Preferably, the on/off controller module is configured to intelligently and adaptively evaluate only internally derived data relative to a pre-programmed glucose boundary (e.g., about 70, 80, 90, 100, 110, 120, 130, 140, 150, or 160 mg/dl glucose) and to select between on and off instructions that actuate the system's integrated insulin delivery device. In one embodiment, integrated system 10 is configured to automatically (e.g., iteratively, continually or continuously) monitor and manage the host's glucose level in real-time, similarly to the glucose regulation by the pancreatic β-cells of a non-diabetic person. In generally, the glucose boundary is selected based on when insulin is, or is not, to be delivered to the host.

In some embodiments, the automated system includes an on/off controller and is configured for use with a flash insulin (e.g., an insulin having a substantially "instant on," rapid peak and short duration TAP, as described in the section entitled "Medicament Delivery Device"), such that the on/off controller can iteratively (e.g., automatically, periodically, or continually) evaluate the internally derived data, calculate and deliver flash insulin doses over a period of time (e.g., minutes, hours, days, etc.) and the effect of insulin dose stacking (e.g., to the host) is substantially negligible and/or can be algorithmically accounted for. On/off controller modules are described in greater detail in the section entitled "On/off Controller Module," and, for example, with reference to FIG. 15.

In some embodiments, the automated integrated system 10 includes a dynamic basal controller module configured to intelligently and adaptively evaluate solely internally derived data relative to a basal profile, and to calculate an insulin therapy within the basal profile, such that the host's glucose is substantially maintained within a target range over a period of hours, days or weeks, with the exception of expected increases in glucose associated with meals and the like. In general, the target range is a range of euglycemic glucose concentrations. Two exemplary target ranges are glucose concentrations from about 80 mg/dl to about 140 mg/dl and from about 100-mg-dl to about 160 mg/dl. Dynamic basal controller modules are described in greater detail in the section entitled "Dynamic Basal Controller Module," and, for example, with reference to FIG. 16.

In some embodiments, the fully automated integrated system is configured to continuously (e.g., intermittently, iteratively, periodically, or automatically) adaptively monitor and evaluate the host's metabolic profile and to determine (e.g., calculate) an insulin therapy. As is known to one skilled in the art, the host's metabolic profile can fluctuate over a period of days or weeks, depending upon the host's activity level and state of health, the types of foods the host is consuming, medications, and the like. Preferably, the controller module (e.g., on/off, basal and/or bolus controller modules) is configured to adaptively and intelligently adjust one or more system parameters (e.g., glucose boundary, basal profile, bolus constraint, insulin delivery rate, and the like) in response to internally derived data and the host's metabolic profile. While not wishing to be bound by theory, it is believed that configuring the fully automated integrated system to adaptively monitor and evaluate the user's metabolic profile promotes optimal insulin dosing, improves system accuracy and reduces the number of host hypoglycemic episodes, which ultimately promotes improved host health and safety.

Single Point Glucose Monitor

In the illustrated embodiments (FIGS. 5 to 8), the single point glucose monitor includes a meter for measuring glucose within a biological sample including a sensing region that has a sensing membrane impregnated with an enzyme, similar to the sensing membrane described with reference to U.S. Pat. Nos. 4,994,167 and 4,757,022, each which is incorporated herein in its entirety by reference. However, in alternative embodiments, the single point glucose monitor can use other measurement techniques such as conventional finger stick/test strip meters, optical devices, and the like. It is noted that the meter is optional in that a separate meter can be used and the glucose data downloaded or input by a user into the receiver. However the illustrated embodiments show an integrated system that exploits the advantages associated with integration of the single point glucose monitor with the receiver 14 and delivery device 16.

FIGS. 5 to 8 are perspective views of integrated receivers including a single point glucose monitor. It is noted that the integrated single point glucose monitor can be integral with, detachably connected to, and/or operably connected (wired or wireless) to the receiver 14 and medicament delivery device 16. The single point glucose monitor 18 integrates rapid and accurate measurement of the amount of glucose in a biological fluid and its associated processing with the calibration, validation, other processes associated with the continuous receiver 14, such as described in more detail with reference to U.S. Patent Publication No. US-2005-0154271-A1 which is incorporated herein by reference in its entirety.

In the illustrated embodiments, the single point glucose monitor 18, such as described in the above-cited U.S. Patent Publication No. US-2005-0154271-A1, includes a body 62 that houses a sensing region 64, which includes a sensing membrane located within a port. A shuttle mechanism 66 can be provided that preferably feeds a single-use disposable bioprotective film that can be placed over the sensing region 64 to provide protection from contamination. The sensing region includes electrodes, the top ends of which are in contact with an electrolyte phase (not shown), which is a free-flowing fluid phase disposed between the sensing membrane and the electrodes. The sensing region measures glucose in the biological sample in a manner such as described in more detail above, with reference the continuous glucose sensor, and as described in U.S. Pat. Nos. 4,994,167 and 4,757,022. The similarity of the measurement technologies used for the continuous glucose sensor and the single point glucose sensor provides an internal control that creates increased reliability by nature of consistency and decreased error potential that can otherwise be increased due to combining dissimilar measurement techniques. Additionally, the disclosed sensing membrane is known to provide longevity, repeatability, and cost effectiveness, for example as compared to single use strips, or the like. However, other single point glucose monitors can be used with the preferred embodiments.

In one alternative embodiment, the single point glucose monitor comprises an integrated lancing and measurement device such as described in U.S. Pat. No. 6,607,658. In another alternative embodiment, the single point glucose monitor comprises a near infrared device such as described in U.S. Pat. No. 5,068,536. In another alternative embodiment, the single point glucose monitor comprises a reflectance reading apparatus such as described in U.S. Pat. No. 5,426,032. In another alternative embodiment, the single point glucose monitor comprises a spectroscopic transflectance device such as described in U.S. Pat. No. 6,309,884. Each of the above patents and patent applications is incorporated in its entirety herein by reference.

In some embodiments, the single point glucose meter further comprises a user interface that includes a display 72 and a button 74; however, some embodiments utilize the display 48 and buttons 50 of the receiver 14 rather than providing a separate user interface for the monitor 18. In some embodiments the single point glucose monitor measured glucose concentration, prompts, and/or messages can be displayed on the user interface 48 or 72 to guide the user through the calibration and sample measurement procedures, or the like. In addition, prompts can be displayed to inform the user about necessary maintenance procedures, such as "Replace Sensor" or "Replace Battery." The button 74 preferably initiates the operation and calibration sequences. The button can be used to refresh, calibrate, or otherwise interface with the single point glucose monitor 18 as is appreciated by one skilled in the art.

Integrated Electronics

FIG. 9 is a block diagram that illustrates integrated system electronics in one embodiment. One embodiment is described wherein the processor module within the receiver performs much of the processing, however it is understood that all or some of the programming and processing described herein can be accomplished within the continuous glucose sensor, the receiver, the single point glucose monitor, and/or the delivery device, or any combination thereof. Similarly, displays, alarms, and other user interface functions can be incorporated into any of the individual components of the integrated delivery device.

A quartz crystal 76 is operably connected to an RF module 78 that together function to receive and synchronize data streams via an antenna 80 (for example, transmission 40 from the RF module 44 shown in FIG. 3). Once received, a processor module 82 processes the signals, such as described below. However, other methods of wired or wireless communication can be substituted for the RF communication described herein.

The processor module 82 is the central control unit that provides the processing for the receiver, such as storing data, analyzing continuous glucose sensor data stream, analyzing single point glucose values, accuracy checking, checking clinical acceptability, calibrating sensor data, downloading data, recommending therapy instructions, calculating medicament delivery amount, type and time, learning individual metabolic patterns, and controlling the user interface by providing prompts, messages, warnings and alarms, or the like. The processor module 82 can include all or part of the controller module, as described elsewhere herein, and with reference to FIGS. 13 to 17, for example. The processor module 82 can include hardware and software that performs the processing described herein, including for example, read only memory 84 (ROM), such as flash memory, provides permanent or semi-permanent storage of data, storing data such as sensor ID, receiver ID, and programming to process data streams (for example, programming for performing estimation and other algorithms described elsewhere herein), and random access memory 88 (RAM) stores the system's cache memory and is helpful in data processing. For example, the RAM 88 stores information from the continuous glucose sensor, delivery device, and/or single point glucose monitor for later recall by the user or a doctor; a user or doctor can transcribe the stored information at a later time to determine compliance with the medical regimen or evaluation of glucose response to medication administration (for example, this can be accomplished by downloading the information through the pc com port 90). In addition, the RAM 88 can also store updated program instructions and/or host specific information. FIGS. 10 and 11 describe more detail about programming that is preferably processed by the processor module 82. In some alternative embodiments, memory storage components comparable to ROM and RAM can be used instead of or in addition to the preferred hardware, such as SRAM, EEPROM, dynamic RAM, non-static RAM, rewritable ROMs, flash memory, or the like.

In some embodiments, the processor module 82 monitors the internally derived data (e.g., the continuous glucose sensor data stream) 40 to determine a preferable time for capturing glucose concentration values using the single point glucose monitor electronics 116 for calibration of the continuous sensor data stream. For example, when sensor glucose data (for example, observed from the data stream) changes too rapidly, a single point glucose monitor reading may not be sufficiently reliable for calibration during unstable glucose changes in the host; in contrast, when sensor glucose data are relatively stable (for example, relatively low rate of change), a single point glucose monitor reading can be taken for a reliable calibration. In some additional embodiments, the processor module can prompt the user via the user interface to obtain a single point glucose value for calibration at predetermined intervals. In some additional embodiments, the user interface can prompt the user to obtain a single point glucose monitor value for calibration based upon certain events, such as meals, exercise, large excursions in glucose levels, faulty or interrupted data readings, or the like. In some embodiments, certain acceptability parameters can be set for reference values received from the single point glucose monitor. For example, in one embodiment, the receiver only accepts reference glucose data between about 40 and about 400 mg/dL.

In some embodiments, the processor module 82 monitors the internally derived data, such as but not limited to the continuous glucose sensor data stream, to determine a preferable time for medicament delivery, including type, amount, and time. In some embodiments, the processor module is programmed to detect impending clinical risk and can request data input, a reference glucose value from the single point glucose monitor, or the like, in order to confirm a therapy recommendation. In some embodiments, the processor module is programmed to process internally derived data and medicament therapies to adaptive adjust to an individual's metabolic patterns. In some embodiments, the processor module is programmed to project glucose trends based on data from the integrated system (for example, medicament delivery information, user input, or the like). In some embodiments, the processor module is programmed to calibrate the continuous glucose sensor based on the integrated single point glucose monitor. Numerous other programming can be incorporated into the processor module, as is appreciated by one skilled in the art, as is described in cited patents and patent applications here, and as is described with reference to flowcharts of FIGS. 10 to 12.

It is noted that one advantage of integrated system of the preferred embodiments can be seen in the time stamp of the sensor glucose data, medicament delivery data, and reference glucose data. Namely, typical implementations of the continuous glucose sensor 12, wherein the medicament delivery 16 and/or single point glucose monitor 18 is not integral with the receiver 14, the reference glucose data or medicament delivery data can be obtained at a time that is different from the time that the data is input into the receiver 14. Thus, the user may not accurately input the "time stamp" of the delivery or, for example, the time or obtaining reference glucose value or administering the medicament, at the time of reference data input into the receiver. Therefore, the accuracy of the calibration of the continuous sensor, prediction of glucose values, therapy recommendations, and other processing is subject to human error (for example, due to inconsistencies in entering the actual time of the single point glucose test). In contrast, the preferred embodiments of the integrated system advantageously do no suffer from this potential inaccuracy when the time stamp is automatically and accurately obtained at the time of the event. Additionally, the processes of obtaining reference data and administering the medicament can be simplified and made convenient using the integrated receiver because of fewer loose parts (for example, cable, test strips, etc.) and less required manual data entry.

A battery 92 is operably connected to the processor module 82 and provides power for the receiver. In one embodiment, the battery is a standard AAA alkaline battery, however any appropriately sized and powered battery can be used. In some embodiments, a plurality of batteries can be used to power the system. In some embodiments, a power port (not shown) is provided permit recharging of rechargeable batteries. A quartz crystal 94 is operably connected to the processor module 168 and maintains system time for the computer system as a whole.

A PC communication (com) port 90 can be provided to enable communication with systems, for example, a serial communications port, allows for communicating with another computer system (for example, PC, PDA, server, and the like). In one exemplary embodiment, the receiver is able to download historical data to a physician's PC for retrospective analysis by the physician. The PC communication port 90 can also be used to interface with other medical devices, for example pacemakers, implanted analyte sensor patches, infusion devices, telemetry devices, and the like.

A user interface 96 comprises a keyboard 98, speaker 100, vibrator 102, backlight 104, liquid crystal display (LCD) 106, one or more buttons 108, and/or a scroll wheel (not shown). The components that comprise the user interface 96 provide controls to interact with the user. The keyboard 98 can allow, for example, input of user information about himself/herself, such as mealtime, exercise, insulin administration, and reference glucose values. The speaker 100 can provide, for example, audible signals or alerts for conditions such as present and/or predicted hyper- and hypoglycemic conditions. The vibrator 102 can provide, for example, tactile signals or alerts for reasons such as described with reference to the speaker, above. The backlight 104 can be provided, for example, to aid the user in reading the LCD in low light conditions. The LCD 106 can be provided, for example, to provide the user with visual data output. In some embodiments, the LCD is a touch-activated screen. The buttons 108 can provide for toggle, menu selection, option selection, mode selection, and reset, for example. In some alternative embodiments, a microphone can be provided to allow for voice-activated control.

The user interface 96, which is operably connected to the processor module 82, serves to provide data input and output for both the continuous glucose sensor, delivery mechanism, and/or for the single point glucose monitor. Data output includes a numeric estimated analyte value, an indication of directional trend of analyte concentration, a graphical representation of the measured analyte data over a period of time, alarms/alerts, therapy recommendations, actual therapy administered, event markers, and the like. In some embodiments, the integrated electronics are configured to display a representation of a target glucose value or target glucose range on the user interface. Some additional data representations are disclosed in U.S. Patent Publication No. US-2005-0203360-A1, which is incorporated herein by reference in its entirety.

In some embodiments, prompts or messages can be displayed on the user interface to guide the user through the initial calibration and sample measurement procedures for the single point glucose monitor. Additionally, prompts can be displayed to inform the user about necessary maintenance procedures, such as "Replace Sensing Membrane" or "Replace Battery." Even more, the glucose concentration value measured from the single point glucose monitor can be individually displayed.

In some embodiments, prompts or messages can be displayed on the user interface to convey information to the user, such as malfunction, outlier values, missed data transmissions, or the like, for the continuous glucose sensor. Additionally, prompts can be displayed to guide the user through calibration of the continuous glucose sensor. Even more, calibrated sensor glucose data can be displayed, which is described in more detail with reference to U.S. Patent Publication No. US-2005-0027463-A1 and U.S. Patent Publication No. US-2005-0203360-A1, each of which is incorporated herein by reference in its entirety.

In some embodiments, prompts or messages about the medicament delivery device can be displayed on the user interface to inform or confirm to the user type, amount, and time of medicament delivery. In some embodiments, the user interface provides historical data and analytes pattern information about the medicament delivery, and the host's metabolic response to that delivery, which may be useful to a host or doctor in determining the level of effect of various medicaments.

Electronics 110 associated with the delivery device 16 (namely, the semi-automated and automated delivery devices) are operably connected to the processor module 82 and include a processor module 112 for processing data associated with the delivery device 16 and include at least a wired or wireless connection (for example, RF module) 114 for transmission of data between the processor module 82 of the receiver 14 and the processor module 112 of the delivery device 16. Other electronics associated with any of the delivery devices cited herein, or other known delivery devices, may be implemented with the delivery device electronics 110 described herein, as is appreciated by one skilled in the art.

In some embodiments, the processor module 112 comprises programming for processing the delivery information in combination with the internally derived data (e.g., continuous sensor information). In some embodiments, the processor module 112 includes all or part of the controller module, as described elsewhere herein. In some alternative embodiments, the processor module 82 comprises programming for processing the delivery information in combination with the internally derived data. In some embodiments, both processor modules 82 and 112 mutually process information related to each component.

In some embodiments, the medicament delivery device 16 further includes a user interface (not shown), which may include a display and/or buttons, for example. U.S. Pat. Nos. 6,192,891, 5,536,249, and 6,471,689 describe some examples of incorporation of a user interface into a medicament delivery device, as is appreciated by one skilled in the art.

Electronics 116 associated with the single point glucose monitor 18 are operably connected to the processor module 120 and include a potentiostat 118 in one embodiment that measures a current flow produced at the working electrode when a biological sample is placed on the sensing membrane, such as described above. The current is then converted into an analog signal by a current to voltage converter, which can be inverted, level-shifted, and sent to an A/D converter. The processor module can set the analog gain via a control port (not shown). The A/D converter is preferably activated at one-second intervals. The processor module evaluates the converter output with any number of pattern recognition algorithms known to those skilled in the art until a glucose peak is identified. A timer is then preferably activated for about 30 seconds at the end of which time the difference between the first and last electrode current values is calculated. This difference is then divided by the value stored in the memory during instrument calibration and is then multiplied by the calibration glucose concentration. The glucose value in milligram per deciliter, millimoles per liter, or the like, is then stored in the processor module, displayed on the user interface, used to calibrate of the glucose sensor data stream, downloaded, etc.

Programming and Processing

FIG. 10 is a flow chart that illustrates the process 130 of validating therapy instructions prior to medicament delivery in one embodiment. In some embodiments, the therapy recommendations include a suggestion on the user interface of time, amount, and type of medicament to delivery. In some embodiments, therapy instructions include calculating a time, amount, and/or type of medicament delivery to administer, and optionally transmitting those instructions to the delivery device. In some embodiments, therapy instructions include that portion of a closed loop system wherein the determination and delivery of medicament is accomplished, as is appreciated by one skilled in the art.

Although computing and processing of data is increasingly complex and reliable, there are circumstances by which the therapy recommendations necessitate human intervention. Some examples include when a user is about to alter his/her metabolic state, for example due to behavior such as exercise, meal, pending manual medicament delivery, or the like. In such examples, the therapy recommendations determined by the programming may not have considered present or upcoming behavior, which may change the recommended therapy. Numerous such circumstances can be contrived; suffice it to say that a validation may be advantageous in order to ensure that therapy recommendations are appropriately administered.

At block 132, a sensor data receiving module, also referred to as the sensor data module, receives sensor data (e.g., a data stream), including one or more time-spaced sensor data points, from a sensor via the receiver, which may be in wired or wireless communication with the sensor. The sensor data point(s) may be raw or smoothed, such as described in U.S. Patent Publication No. US-2005-0043598-A1 which is incorporated herein by reference in its entirety.

At block 134, a medicament calculation module, which is a part of a processor module, calculates a recommended medicament therapy based on the received sensor data. A variety of algorithms may be used to calculate a recommended therapy as is appreciated by one skilled in the art.

At block 136, a validation module, which is a part of the processor module, optionally validates the recommended therapy. The validation may include a request from the user, or from another component of the integrated system 10, for additional data to ensure safe and accurate medicament recommendation or delivery. In some embodiments, the validation requests and/or considers additional input, such as time of day, meals, sleep, calories, exercise, sickness, or the like. In some embodiments, the validation module is configured to request this information from the user. In some embodiments, the validation module is responsive to a user inputting such information.

In some embodiments, when the integrated system 10 is in fully automated mode, the validation module is triggered when a potential risk is evaluated. For example, when a clinically risky discrepancy is evaluated, when the acceleration of the glucose value is changing or is low (indicative of a significant change in glucose trend), when it is near a normal meal, exercise or sleep time, when a medicament delivery is expected based on an individual's dosing patterns, and/or a variety of other such situations, wherein outside influences (meal time, exercise, regular medicament delivery, or the like) may deem consideration in the therapy instructions. These conditions for triggering the validation module may be pre-programmed and/or may be learned over time, for example, as the processor module monitors and patterns an individual's behavior patterns.

In some embodiments, when the integrated system 10 is in semi-automated mode, the system may be programmed to request additional information from the user regarding outside influences unknown to the integrated system prior to validation. For example, exercise, food or medicament intake, rest, or the like may input into the receiver for incorporation into a parameter of the programming (algorithms) that processing the therapy recommendations.

At block 138, the receiver confirms and sends (for example, displays, transmits and/or delivers) the therapy recommendations. In manual integrations, the receiver may simply confirm and display the recommended therapy, for example. In semi-automated integrations, the receiver may confirm, transmit, and optionally delivery instructions to the delivery device regarding the recommended therapy, for example. In automated integrations the receiver may confirm and ensure the delivery of the recommended therapy, for example. It is noted that these examples are not meant to be limiting and there are a variety of methods by which the receiver may confirm, display, transmit, and/or deliver the recommended therapy within the scope of the preferred embodiments.

FIG. 11 is a flow chart 140 that illustrates the process of providing adaptive metabolic control using an integrated system in one embodiment. In this embodiment, the integrated system is programmed to learn the patterns of the individual's metabolisms, including metabolic response to medicament delivery.

At block 142, a medicament data receiving module, which may be programmed within the receiver 14 and/or medicament delivery device 16, receives medicament delivery data, including time, amount, and/or type. In some embodiments, the user is prompted to input medicament delivery information into the user interface. In some embodiments, the medicament delivery device 16 sends the medicament delivery data to the medicament data-receiving module.

At block 144, a sensor data receiving module, also referred to as the sensor data module, receives sensor data (e.g., a data stream), including one or more time-spaced sensor data points, from a sensor via the receiver, which may be in wired or wireless communication with the sensor.

At block 146, the processor module, which may be programmed into the receiver 14 and/or the delivery device 16 is programmed to monitor the sensor data from the sensor data module 142 and medicament delivery from the medicament delivery module 144 to determine an individual's metabolic profile, including their response to various times, amounts, and/or types of medicaments. The processor module uses any pattern recognition-type algorithm as is appreciated by one skilled in the art to quantify the individual's metabolic profile.

At block 148, a medicament calculation module, which is a part of a processor module, calculates the recommended medicament based on the sensor glucose data, medicament delivery data, and/or individual's metabolic profile. In some embodiments, the recommended therapy is validated such as described with reference to FIG. 10 above. In some embodiments, the recommended therapy is manually, semi-automatically, or automatically delivered to the host.

At block 150, the process of monitoring and evaluation a host's metabolic profile is repeated with new medicament delivery data, wherein the processor monitors the sensor data with the associated medicament delivery data to determine the individual's metabolic response in order to adaptively adjust, if necessary, to newly determined metabolic profile or patterns. This process may be continuous throughout the life of the integrated system, may be initiated based on conditions met by the continuous glucose sensor, may be triggered by a host or doctor, or may be provided during a start-up or learning phase.

While not wishing to be bound by theory, it is believed that by adaptively adjusting the medicament delivery based on an individual's metabolic profile, including response to medicaments, improved long-term host care and overall health can be achieved.

Figure 12:
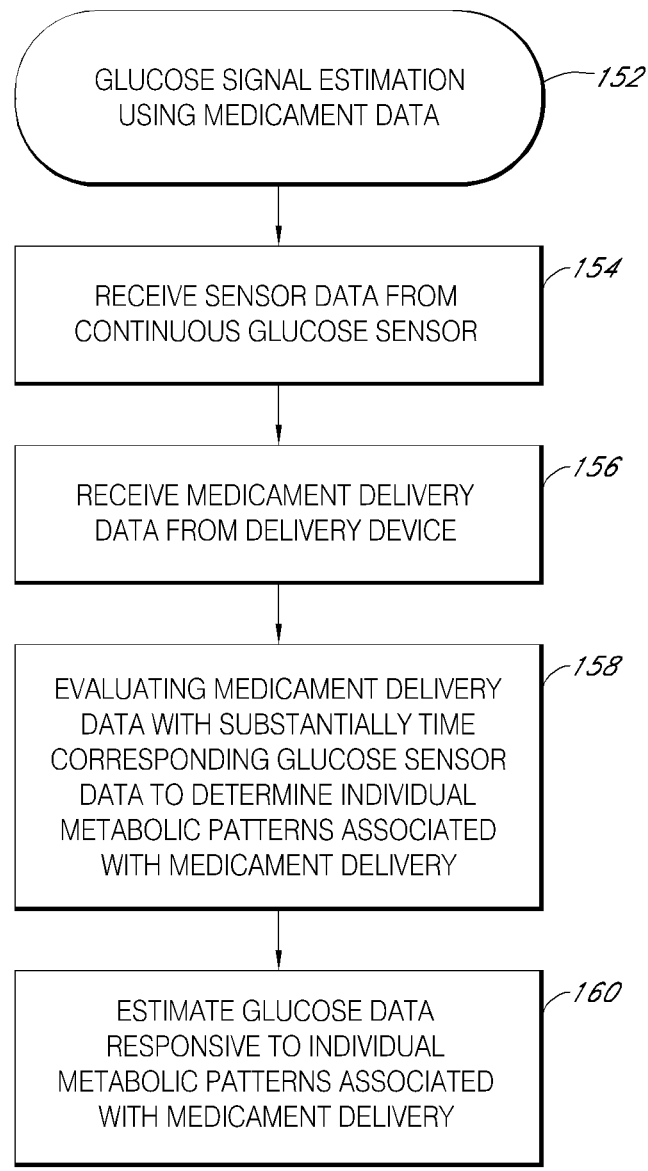
FIG. 12 is a flow chart that illustrates the process of glucose signal estimation using the integrated sensor and medicament delivery device in one embodiment.

FIG. 12 is a flow chart 152 that illustrates the process of glucose signal estimation using the integrated sensor and medicament delivery device in one embodiment. It is noted that glucose estimation and/or prediction are described in U.S. Patent Publication No. US-2005-0027463-A1 and U.S. Patent Publication No. US-2005-0203360-A1, each of which has been incorporated herein by reference in its entirety. However, the preferred embodiments described herein, further incorporated additional data of medicament delivery in estimating or predicting glucose trends.

At block 154, a sensor data receiving module, also referred to as the sensor data module, receives sensor data (e.g., a data stream), including one or more time-spaced sensor data points, from a sensor via the receiver, which may be in wired or wireless communication with the sensor.

At block 156, the medicament data receiving module, which may be programmed within the receiver 14 and/or medicament delivery device 16, receives medicament delivery data, including time, amount, and/or type.

At block 158, the processor module evaluates medicament delivery data with substantially time corresponding glucose sensor data to determine individual metabolic patterns associated with medicament delivery. "Substantially time corresponding data" refers to that time period during which the medicament is delivered and its period of release in the host.

At block 160, the processor module estimates glucose values responsive to individual metabolic patterns associated with the medicament delivery. Namely, the individual metabolic patterns associated with the medicament delivery are incorporated into the algorithms that estimate present and future glucose values, which are believed to increase accuracy of long-term glucose estimation.

Figure 13:
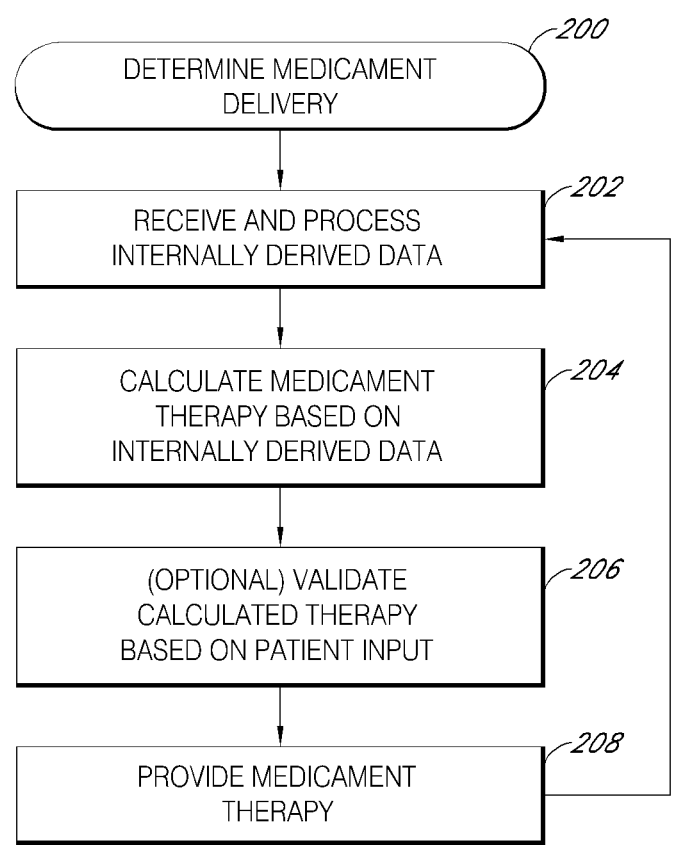
FIG. 13 is a flow chart that illustrates the process of determining medicament delivery in one embodiment.

FIG. 13 is a flow chart 200 that illustrates the process of determining medicament delivery using an integrated system 10, in one embodiment. In preferred embodiments, medicament (e.g., insulin or another drug) delivery is calculated to maintain the host substantially at and/or within a target range. In the case of insulin therapy, the target range is generally a range of preferred glucose concentrations within which the host is to maintain (at least to try) his blood sugar, as is discussed below. For example, in some circumstances, the target range is a range of euglycemic glucose concentrations. As is understood by those skilled in the art, glycemic ranges can vary, depending upon the therapy goals and the morbidity/mortality associated with a given glucose level (e.g., concentration). For example, according to the American Diabetes Association, a preferred target range is a euglycemic range that provides tight glucose control and substantially reduces diabetic morbidity and mortality, namely a fasting glucose of from 90 mg/dl to 130 mg/dl. Alternative target ranges can be used, such as from about 70, 80, 90, 100, 110 or 120 mg/dl to about 110, 120, 130, 140, 150 or 160 mg/dl or more. In some circumstances, the target range can be very wide (e.g., from about 80 mg/dl to about 160 mg/dl) or very narrow (e.g., 90 mg/dl to 120 mg/dl) or even a single glucose concentration. In some embodiments, the host and/or his health care professional select a target range. In some embodiments, the target range is programmable (e.g., pre-programmable, re-programmable), such as by the host, a caretaker of the host or the manufacturer. In some embodiments, the integrated system includes two or more target ranges. In some embodiments, the controller module is configured to adaptively/intelligently program (e.g., re-program) the target range, such as after evaluation of the internally derived data and the host's metabolic response to insulin therapy.

At block 202, the processor module is configured to receive and process internally derived data. Internally derived data can include but it not limited to continuous glucose sensor data, continuous glucose processed sensor data, auxiliary sensor data, processed auxiliary sensor data, delivery device data and processed delivery device data, including glucose concentration, glucose concentration range, change in glucose concentration, glucose concentration rate of change, acceleration of the glucose concentration rate of change, host insulin sensitivity, change in host insulin sensitivity, host metabolic response to insulin therapy, amount of insulin delivered, time of insulin delivery, insulin on board, time, acceleration, host activity level, pressure, a pH, a temperature, an oxygen level, the level of an analyte other than glucose, a proximity and orientation. In some embodiments, internally derived data can include data derived from algorithmic processing of continuous analyte sensor data and/or auxiliary sensor data and/or medicament delivery device data. In some embodiments, the system is configured to further received external data (e.g., meal occurrence/content, exercise, units of insulin delivered, time of insulin delivery, etc.) such as for historical purposes (e.g., as a diary or log).

At block 204, the system is configured to calculate (e.g., determine) a medicament therapy (e.g., insulin therapy) based solely on internally derived data and any constraint (e.g., range, boundary, profile and the like). In general, calculation of the medicament therapy is conducted by the system's controller module (e.g., on/off, dynamic basal and/or dynamic bolus controller module), as described elsewhere herein. In some embodiments, evaluation and calculation is iterative. In some embodiments, the calculated insulin therapy includes an instruction for delivery of the insulin therapy to the host.

At block 206, the system is optionally configured to validate the calculated therapy based on patient (e.g., host) input. For example, in some embodiments, the host must accept the calculated medicament therapy before the system can proceed to providing (e.g., delivering) the medicament therapy at block 208, and the system can return to block 202. If the host accepts calculated the medicament therapy (e.g., the dose is validated), the medicament therapy will be provided/delivered. Similarly, if the host does not accept the medicament therapy, no medicament will be given. In some embodiments, the system is configured such that the host can command the system to provide a manually calculated dose (e.g., calculated by the host). In some embodiments, the system is further configured to allow the system to adaptively and intelligently determine an appropriate and/or optimal delivery schedule for the commanded manually calculated dose.

At block 208, the system is configured to deliver the calculated insulin therapy, as described elsewhere herein. In some embodiments, the insulin delivery device is configured to deliver the calculated insulin therapy automatically upon receipt of an instruction from the controller module. After delivering the insulin therapy, the system is configured to return to block 202.

Figure 14:
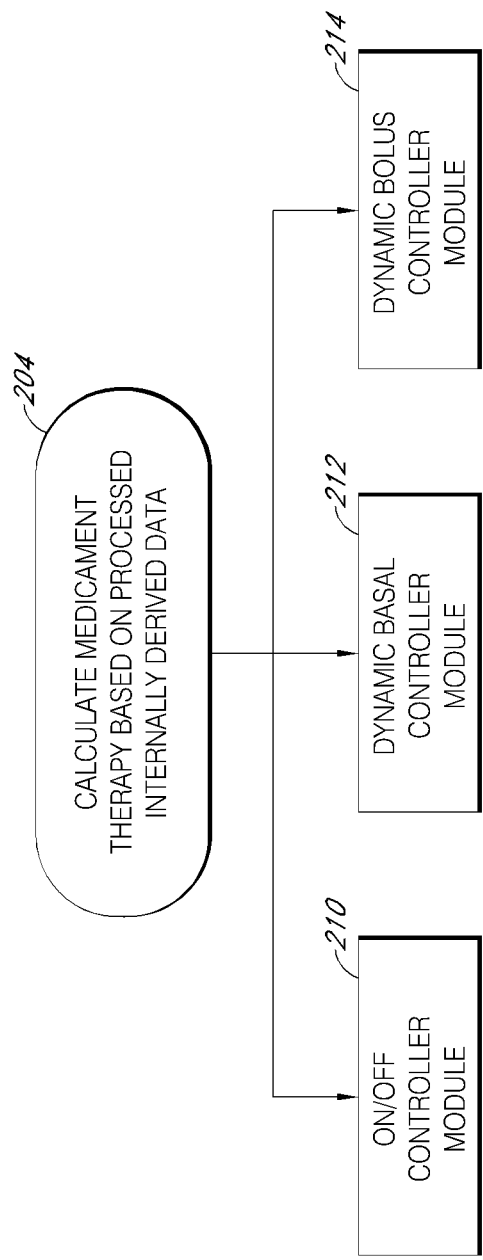
FIG. 14 is a flow chart that illustrates the process of calculating a medicament therapy based on internally derived data in one embodiment.

FIG. 14 is a flow chart 204 that illustrates calculation of a medicament therapy based on the internally derived data, in one embodiment. Generally, the system 10 is configured to use at least one controller module (all or in part) to calculate the insulin therapy, such as but not limited to an on/off controller module 210, a dynamic basal controller module 212 and a dynamic bolus controller module 214. In some embodiments, the system is configured with only one controller module. In other embodiments, the system is configured with two or all three of the controller modules. In one embodiment, the system includes two or more controller modules configured to work in concert (e.g., in conjunction, together, in combination). In some embodiments, the controller module is configured to provide all or some of the processing for block 204 of FIG. 13. The controller module can be incorporated into any portion of the integrated system, such as but not limited to the receiver, the medicament delivery device, a component separate from the receiver and the delivery device, or a combination thereof (e.g., integrated electronics, such as a processor module). In some embodiments, a controller module is included in processor module 82 and/or in processor module 112.

On/Off Controller Module

Figure 15:
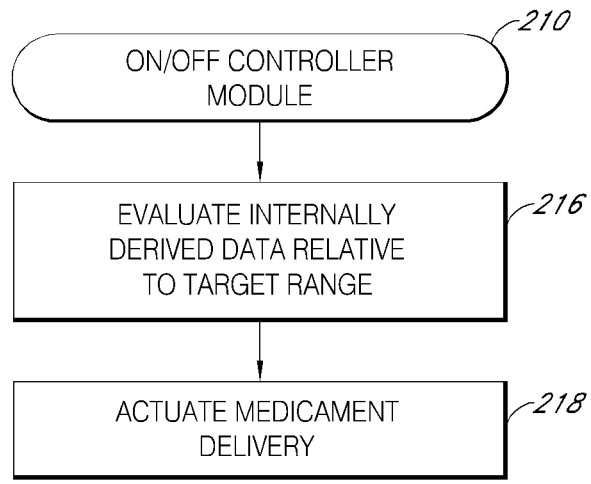
FIG. 15 is a flow chart that illustrates the process of calculating a medicament therapy based on internally derived data, using an on/off controller module, in one embodiment.

FIG. 15 is a flow chart that illustrates an on/off controller module 210, in one embodiment.

At block 216, the on/off controller module is configured to intelligently, adaptively and iteratively evaluate the internally derived data (e.g., raw and/or processed glucose sensor data) relative to a target range and/or a glucose boundary. In some embodiments, a glucose boundary is a host glucose concentration at which the system is configured to deliver insulin. In some embodiments, the target range and the glucose boundary are associated with each other. For example, the glucose boundary can be the upper limit of the target range. In some embodiments, the host does not validate either data or a calculated medicament therapy. In preferred embodiments, the system includes a continuous analyte sensor, and can include one or more auxiliary sensors, such as described elsewhere herein. In some embodiments, the glucose boundary can be programmable, such as by the host, a caretaker of the host and/or the manufacturer. In some embodiments, the glucose boundary is programmable by an intelligent/adaptive controller module.

At block 218, the on/off controller module is configured to actuate medicament delivery, such as by selecting between on and off instructions. The point at which the selection is made can be referred to as a setpoint. In some embodiments, the set point is the glucose boundary. In one exemplary embodiment, the system includes programming to select between the on and off instructions. When evaluation of the internally derived data indicates that the host's glucose is (or has) surpassing (or surpassed) a glucose boundary, the controller module selects the on instruction, which directs actuation of the insulin delivery device (e.g., turns on delivery). Conversely, when the host's glucose falls below a glucose boundary (as determined by evaluation of the internally derived data), the off instruction is selected and insulin delivery is terminated (e.g., turned off). In preferred embodiments, the insulin will be delivered at a programmable rate, which can be programmed by the host, a caretaker of the host, or the manufacturer, for example. In some embodiments, the on/off controller can include more than one setpoint, such as but not limited to a first set point to select the on instruction and a second setpoint to select the off instruction.

In some embodiments, the on/off controller module is configured to adjust the insulin delivery rate in response to evaluation of internally derived data and the host's metabolic response to insulin delivery (e.g., metabolic state). For example, the insulin can be delivered at relatively faster or slower rates, depending upon the evaluation of the internal data. In some circumstances, when the on instruction is selected, the medicament can be delivered substantially continuously and/or intermittently, such as but not limited to at a single rate (e.g., about 0.05 U, 0.1 U, 0.2 U, 0.3 U, 0.4 U, 0.5 U, 0.6 U, 0.7 U, 0.8 U or 0.9 U per hour or more).

In one exemplary embodiment, the integrated system 10 includes an on/off controller module configured to intelligently and adaptively evaluate the internally derived data relative to a programmed glucose boundary and then select between the on and off instructions. For example, if the glucose boundary is 140 mg/dl, then the controller module evaluates the internally derived data against the 140 mg/dl glucose boundary (block 216). If the host's glucose is above the 140 mg/dl glucose boundary, then the controller module selects the on instruction, which leads to actuation of insulin delivery at box 218. If the host's glucose is above the 140 mg/dl glucose boundary and insulin is currently being delivered (e.g., the on instruction was selected at an earlier time), then the controller module does nothing (e.g., insulin continues to be delivered). If the host's glucose is 140 mg/dl or less, the off instruction is selected (or the on instruction is de-selected/terminated), whereby insulin delivery is ceased. In some embodiments, the insulin is delivered (e.g., infused) substantially continuously, such as at a given rate (e.g., U/min), or substantially intermittently, such as small volumes every few minutes (e.g., 0.5-U every 6-minutes). In preferred embodiments, the system is configured, such that data evaluation and/or insulin delivery are iterative (e.g., cyclic, periodic, continuous, automatic, and the like). Because they system is configured to function intelligently and adaptively, in some embodiments, the system can modify (e.g., adjust, either with or without host validation) the glucose boundary and/or the insulin infusion rate, such that maintenance of the host within the target range is optimized.

In another exemplary embodiments, the system 10 includes an on/off controller module configured for use in combination with flash insulin. The flash insulin therapy can be delivered automatically, periodically, intermittently and/or substantially continually, in response to the on/off controller, such that the host is maintained substantially at and/or within the target range. For example, in some embodiments, the system is configured to intermittently deliver small doses of flash insulin when (while) the host's glucose is above the glucose boundary. The rate of flash insulin delivery is programmed such that when the host's glucose is rising and surpasses the glucose boundary, the on instruction is selected and a small amount of flash insulin is delivered. After delivery, the controller module can be configured to wait a brief period (e.g., a few minutes), and then evaluate the internally derived data relative the glucose boundary. If the internally derived data indicates that the host's glucose is still above the glucose boundary, then another small dose of flash insulin can be delivered. Alternatively, the system can be configured to wait until the delivered insulin has had a predetermined effect (e.g., time sufficient for the activity of about 50, 60, 70, 80, 90 or 95% of the delivered insulin to peak, or for the activity of about 50, 60, 70, 80, 90 or 95% of the delivered insulin to terminate), prior to returning to block 202 (FIG. 13). As is appreciated by one skilled in the art, the system can be configured to proceed through several cycles of these steps (e.g., iteratively evaluate and provide insulin doses using the on/off controller module), until the host's glucose level falls to/below the glucose boundary. When the host's glucose level falls to/below the glucose boundary, the on/off controller is configured to select the off instruction, which results in termination of insulin delivery. While not wishing to be bound by theory, it is believed that use of flash insulin in combination with an on/off controller module advantageously substantially prevents stacking of insulin doses and substantially avoids hypoglycemic episodes. Accordingly, improved host health and safety are promoted while diabetic complications are avoided or delayed during the host's lifetime.

In some embodiments, the integrated system is configured arranged for use with other insulins (e.g., regular (e.g., wild type), fast-acting or rapid-acting human insulin analogs, etc.), such that the on/off controller evaluates/tracks "insulin on-board" (e.g., the total amount of active insulin currently in the host's body).

Dynamic Basal Controller Module

As is understood by one skilled in the art, insulin needs vary between individuals and through out the day, both during and between meals. To take care of between meal glucose fluctuations, diabetic hosts generally employ a basal schedule (e.g., basal profile) for continuous delivery of low levels of insulin, such that, between meals, the host's glucose is relatively steady (e.g., remains within a target (e.g., euglycemic) range). Accordingly, in preferred embodiments, the integrated system 10 includes a dynamic basal controller module configured to iteratively evaluate internally derived data relative to a programmable basal profile and iteratively calculate a dynamic basal insulin therapy within the basal profile.

Figure 16:
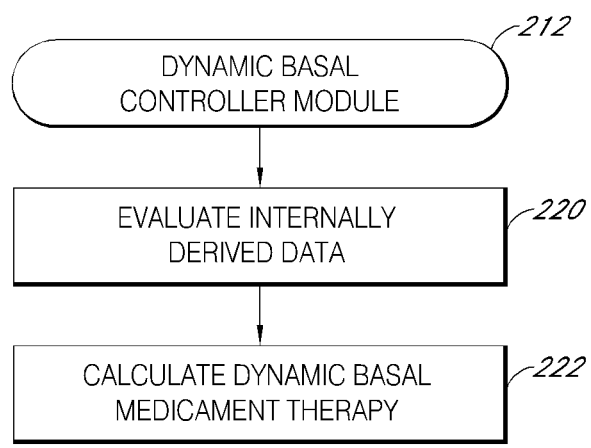
FIG. 16 is a flow chart that illustrates the process of calculating a medicament therapy based on internally derived data, using a dynamic basal controller module, in one embodiment.

FIG. 16 is a flow chart that illustrates a dynamic basal controller module 212, in one embodiment. In preferred embodiments, the dynamic basal controller module can be part of the electronics module and is configured to evaluate internally derived data relative to a basal profile 220 and to intelligently and adaptively calculate a dynamic basal medicament therapy 222, based on that evaluation. In preferred embodiments, the insulin therapy is determined solely on internally derived data and the basal profile.

A basal profile generally includes a schedule of time blocks, each block being associated with an insulin delivery rate. In general, a diabetic host can determine his basal profile by experimentation. For example, the basal insulin delivery rate for a particular time period can be determined by fasting while periodically evaluating the glucose level. Neither food nor bolus insulin can be taken for 4-hours prior to or during the evaluation period. If the blood sugar level changes dramatically during evaluation, then the basal rate can be adjusted to increase or decrease insulin delivery to keep the blood sugar level approximately steady. For instance, to determine the host's morning basal requirement, he must skip breakfast. On waking, he would test his glucose level periodically until lunch. Changes in blood glucose level are compensated with adjustments in the morning basal rate. The process is repeated over several days, varying the fasting period, until a 24-hour basal profile (which keeps fasting blood sugar levels relatively steady) has been built up. As used herein, a basal profile includes a schedule of one or more time blocks, wherein each time block is associated with a maximum insulin delivery rate. As is described herein, in some embodiments, the dynamic basal controller module is constrained by the basal profile. Accordingly, in some embodiments, the controller module is configured to evaluate internally derived data (e.g., including re-evaluate internally derived data as it is received) and to iteratively calculate an insulin delivery rate (e.g., insulin therapy) up to the maximum rate of a current time block. Accordingly, the insulin therapy can include a delivery rate less than the maximum insulin delivery rate associated with the current time block. In some embodiments, the basal profile includes a 24-hour schedule. In some embodiments, the schedule can be shorter or longer than 24-hours. In some embodiments, the schedule is repeatable and/or cyclic (e.g., iterative). In some embodiments, the host, a caretaker of the host, and/or the manufacturer can program a basal profile. In some circumstances, an intelligent/adaptive controller module can be configured to program the basal profile.

At block 220, in preferred embodiments, the dynamic basal controller module is configured to evaluate solely internally derived data (e.g., from an operably connect continuous glucose sensor, from an auxiliary sensor and/or an insulin delivery device) relative to a programmed basal profile. Internally derived data includes but is not limited to glucose concentration, change in concentration, rate of change of concentration, acceleration (or deceleration) of the change, direction of the change, predicted analyte concentration for a future time, estimated analyte concentration, possible variations of analyte data (e.g., based on maximum possible error), trend information and the like. For example, in some circumstances, a low rate of change (in glucose concentration/level) is from about ±0 mg/dl/min to about 1 mg/dl/min, a moderate rate of change is from about 1 mg/dl/min to about 2 mg/dl/min, and a high rate of change is from about 3 mg/dl/min to about 6 mg/dl/min. In some embodiments, the calculation can include evaluation of the host's metabolic response to insulin therapy, which can depend upon a variety of factors, such as but not limited to the type of insulin delivered, the mode and/or location of delivery, and the like.

In some embodiments, internally derived data can include data received from one or more auxiliary sensors, such as but not limited to sensors for glucose, an analyte other than glucose, pH, temperature, pressure, host movement, host body position, proximity, and the like. For example, an accelerometer can provide data regarding the host's activity level (e.g., sedentary versus exercising versus sleeping), which can affect the host's insulin requirement. In one exemplary embodiment, the dynamic basal controller module is configured to evaluate accelerometer data in conjunction with internally derived data, depending upon if the accelerometer data is within or without a programmed range (e.g., whether or not the host is very active). For example, the system can be configured such that if the accelerometer data is above a setpoint (e.g., indicates that the host is very active or exercising), then the accelerometer data is considered by the controller module; if the accelerometer data is below the set point, the accelerometer is not considered. In one exemplary embodiment, the system is configured such that the basal controller module intelligently monitors the host's activity level (e.g., over a period of days and/or weeks) and adaptively adjusts the basal profile to maintain the host substantially within the target range during both active and inactive periods of the day. For example, in some embodiments, the controller module is configured to intelligently determine when the host is generally very active (e.g., exercising), less active (e.g., working at the computer) or sedentary (e.g., sleeping). Some hosts will tend to be more active than others. Advantageously, because the controller module responds to changes in the host's metabolic state, each host can have a basal profile optimized to his personal needs.

At block 222, in some embodiments, the dynamic basal controller module is configured to calculate (e.g., determine) a dynamic basal medicament therapy (also referred to as the "insulin therapy") based solely on the internally derived data and the basal profile (e.g., the evaluation thereof), wherein the calculated insulin therapy falls within the basal profile. The insulin therapy calculated by the dynamic basal controller module is a rate of insulin delivery less than or equal to the insulin delivery rate associated with the basal profile (e.g., at the current block of time). Preferably, the delivery rate is sufficient to bring the host's glucose concentration substantially within a pre-programmed target range (e.g., a euglycemic range). Over time, the insulin therapy can include a plurality of delivery rates at different time blocks calculated to maintain the host within the target range. In some embodiments, the maximum insulin therapy (e.g., delivery rate) is from about 0.01 U/hour or less to about 6.0 U/hour or more. For example, in some embodiments, the maximum insulin therapy is from about 0.01 U/hr to about 0.2 U/hr. In some embodiments, the maximum insulin therapy is from about 0.21 U/hr to about 0.3 U/hr. In some embodiments, the maximum insulin therapy is from about 0.31 U/hr to about 0.4 U/hr. In some embodiments, the maximum insulin therapy is from about 0.41 U/hr to about 0.5 U/hr. In some embodiments, the maximum insulin therapy is from about 0.51 U/hr to about 1.0 U/hr. In some embodiments, the maximum insulin therapy is about 1.5 U/hr, 2.0 U/hr, 2.5 U/hr, 3.0 U/hr, 3.5 U/hr, 4.0 U/hr, 4.5 U/hr, 5.0 U/hr, or 5.5 U/hr. In preferred embodiments, instructions for delivery of the calculated insulin therapy are sent to the insulin delivery device, which then automatically delivers the instructed insulin therapy. In some embodiments, dynamic basal controller module can include one or more instructions for calculation and/or delivery of the basal insulin therapy. The calculated insulin delivery rate can be an instruction provided to an insulin delivery device to delivery the insulin therapy, such as to automatically deliver the therapy.

In preferred embodiments, the system 10 is configured to iteratively (e.g., cyclic, periodic, and the like) evaluate the internally derived data (e.g., including past and newly/more recently received internally derived data) and to iteratively calculate an insulin delivery rate. Because the system is configured to function intelligently and adaptively, in some embodiments, the system can respond to changes in the host's metabolic state by modifying (e.g., adjusting, programming, re-programming, either with or without host validation) the basal profile, such that maintenance of the host within the selected target range is optimized. In some embodiments, the controller module includes programming to adjust the basal profile in response to internally derived data and the host's metabolic response. In some embodiments, the insulin therapy substantially maintains the host's glucose concentration within the target range without driving the host into a hyper- or hypoglycemic range. In some embodiments, the dynamic basal controller module includes one or more instructions configured to process the internally derived data and iteratively provide the therapy instructions. In a further embodiment, these instructions include instructions for evaluating the internally derived data and calculating the insulin therapy based solely on the internally derived data.

In one exemplary embodiment, the integrated system includes a dynamic basal controller module configured to iteratively (continually, automatically, periodically, or intermittently) evaluate the internally derived data relative to a programmable basal profile and calculate an insulin therapy that falls within the basal profile. For example, if the current time block of the basal profile specifies 2 U of insulin per hour, then the controller module can calculate an insulin therapy up to that amount. Preferably, the calculated insulin therapy is optimal for maintaining the host within the selected (e.g., preferred, engaged, programmed) target range. As the system receives additional internal data, it is configured to adjust the insulin delivery rate in an intelligent and adaptive manner. For example, if the evaluation of currently received internal data indicates that for optimal control (e.g., of blood sugar) the insulin delivery rate should be increased from 0.5 U/hr to 1 U/hr, then the controller module can both send instructions to the integrated insulin delivery device to do so and reprogram the basal profile with the new delivery rate for that time block. In another example, if the evaluation might indicates that the delivery rate should be reduced to maintain optimal control, and then the controller module can calculate a new insulin therapy and instruct the delivery device accordingly. Internally derived data can include trend information, such as but not limited to changes in the host's insulin needs (e.g., response to delivered insulin, insulin sensitivity, or metabolic profile) over time. Accordingly, in preferred embodiments, the dynamic basal controller module is configured to evaluate this trend information and make intelligent adjustments to (e.g., re-program) the insulin therapy and/or the basal profile, such that between meal glucose control can be optimized (e.g., continually). In some embodiments, the system is configured to request validation of such a change (e.g., re-programming) in insulin therapy and/or the basal profile.

In some embodiments, the dynamic basal controller module can be configured to evaluate the internally derived data 220 with respect to one or more target ranges (which can overlap) to intelligently and adaptively direct calculation of the dynamic basal medicament therapy. For example, in one exemplary embodiment, as a first step, the dynamic basal controller module evaluates the internally derived data with respect to glycemic ranges (e.g., hypoglycemic, euglycemic, hyperglycemic or very hyperglycemic). If, for example, the host is euglycemic, a first calculation can be made; if the host is hyperglycemic a second calculation can be made; and if the host is hypoglycemic a third calculation can be made. In some embodiments, the controller evaluates the rate and/or direction of glucose concentration change and/or acceleration of the change (e.g., if glucose concentration has changed, if it is going up or down, if it is changing slowly or rapidly, etc.). For example, if the glucose level is very hyperglycemic and increasing rapidly, a first dynamic basal insulin dose (e.g., dose #1) can be calculated. If the glucose level is very hyperglycemic and decreasing slowly, a second dynamic basal insulin dose (e.g., dose #2), which might be smaller than dose #1, can be calculated. If the glucose level is slightly hyperglycemic and increasing slowly, a third dynamic basal insulin dose (dose #3) can be calculated. Dose #3 may be smaller than both dose #1 and dose #2. If, on the other hand, the glucose level is in the euglycemic range and decreasing slowly, insulin delivery can be terminated (e.g., until the glucose level was again above the euglycemic range). In another example, if the glucose level is in euglycemic range and decreasing rapidly, or in the hypoglycemic range, the controller can be configured to alert the host, such as by an alarm, for example so that he can eat some sugar to raise his glucose level.

In some embodiments, the dynamic basal controller module is configured for use in conjunction with a flash-acting insulin, as described elsewhere herein. In one exemplary embodiment, the onset of activity of the flash insulin is less than about 5-minutes as determined by plasma insulin concentration according to the methods of Frohnauer et al). In some embodiments, the flash insulin's activity peaks within about 10 to 30-minutes. In some embodiments, the flash insulin's duration of activity is about 30-minutes or less and up to about 1-hour. In some embodiments, the flash insulin's activity peaks within about 5-minutes of delivery and terminates within about 10-20 minutes.

In some embodiments, the dynamic basal controller module is configured for use in conjunction with a regular, rapid-acting or fast-acting insulin (including analogs), as described elsewhere herein. In a further embodiment, the dynamic basal controller module is configured to track the amount of insulin "on board" (e.g., the total amount of active insulin currently within the host and the insulin activity associated with that amount), and to evaluate the insulin on board when calculating a dynamic basal therapy.

Dynamic Bolus Controller Module

Conventionally, when a host is going to eat a meal, he calculates a bolus insulin dose that should be sufficient to cover the glucose increase anticipated due to consumption of the meal. He then gives himself the calculated bolus dose and eats the meal. Without careful measurement of carbohydrate and fat content of the meal and the host's insulin sensitivity, the calculated bolus dose can only estimate the amount of insulin to be taken for that meal. Thus, in general, the calculated bolus dose will not be the optimal dose to cover the actual glucose increase that occurs when the meal is eaten. The host's sugar may increase more than he thought it would, in which case the calculated bolus dose could be too small, which could lead to hyperglycemia. Alternatively, the host's sugar might not rise as high as he thought it would, in which case the calculated bolus dose may be too large, and could lead to hypoglycemia. Accordingly, in preferred embodiments, the integrated system 10 includes a dynamic bolus controller module configured to iteratively evaluate internally derived data relative to a programmable bolus constraint and iteratively calculate a dynamic bolus insulin therapy, upon host activation of the programmable bolus constraint.

Figure 17:
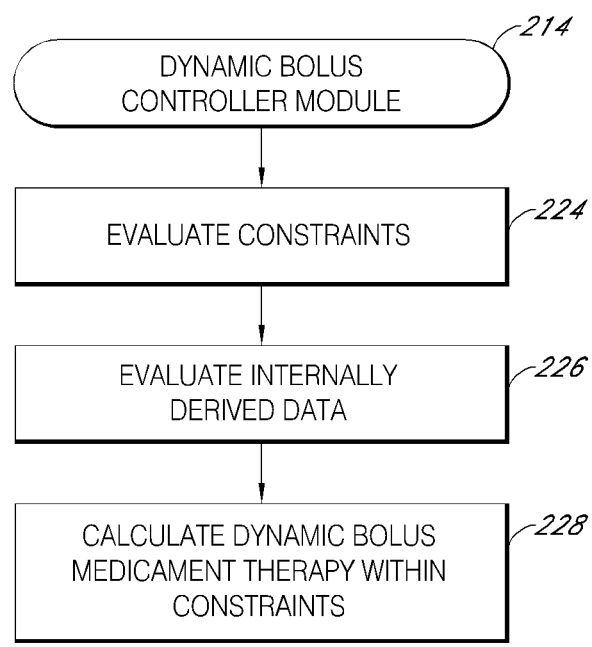
FIG. 17 is a flow chart that illustrates the process of calculating a medicament therapy based on internally derived data, using a dynamic bolus module, in one embodiment.

FIG. 17 is a flow chart illustrating a dynamic bolus controller module 214, in one embodiment. In preferred embodiments, the dynamic bolus controller module is included in the electronics module and is configured to evaluate an engageable constraint 224 as well as internally derived data 226. In some embodiments, the dynamic bolus controller module is configured to intelligently provide a dynamic bolus medicament therapy (e.g., insulin therapy) within a pre-set (e.g., programmable) constraint 228, such as in response to the host engaging the bolus constraint. Preferably, the dynamic bolus controller module is configured to iteratively calculate an insulin therapy based solely on evaluation of internally derived data (e.g., re-evaluation of internally derived data as it is received) and the bolus constraint. In some embodiments, the dynamic bolus controller module 214 allows host validation of the dynamic bolus medicament therapy (e.g., FIG. 13, box 206), which is believed to promote increased user confidence, increased host compliance and improved health status. Advantageously, the dynamic bolus controller module 214 can be configured to use a variety of insulins, including but not limited to regular or rapid/quick-acting insulins (e.g., slower onset and peak of activity, longer duration of activity) and flash insulins, described elsewhere herein.

In preferred embodiments, an engageable bolus constraint is associated with a programmable dynamic bolus insulin therapy. In preferred embodiments, the dynamic bolus insulin therapy is the maximum total insulin that can be delivered to the host over a specified period of time, in response to the host engaging (e.g., selecting) the bolus constraint associated with the insulin therapy. In some embodiments, the insulin therapy comprises one or more portions of the maximum total insulin dose, as described below. In some embodiments, the bolus constraint can be programmed (e.g., pre-programmed and/or pre-set), programmable and/or re-programmable. In some embodiments, the host and/or a caretaker of the host can program the bolus constraint. In some embodiments, the bolus constraint can be programmed by the manufacturer or the dynamic bolus controller module.

At block 224, the dynamic bolus controller module is configured to evaluate a bolus constraint (e.g., engageable/selectable, and programmable, re-programmable and/or pre-set limit), such as one that has been engaged by the host. In general, a bolus constraint is associated with an insulin therapy that has been calculated and/or estimated to be sufficient to cover an average expected rise in blood sugar, such as an increase in glucose that occurs (on average) when a host eats a given meal, such as but not limited to breakfast, lunch, dinner and the like. For example, on most days, the host may eat very similar breakfasts (e.g., an average (e.g., usual) breakfast), which can cause very similar glucose increases (e.g., an average increase in glucose). Accordingly, a "breakfast" bolus constraint can be calculated to cover the average rise in glucose associated with an average breakfast. In some embodiments, a bolus constraint can be associated with a host activity (e.g., to cover the glucose rise associated with host performance of about 30-minutes of vigorous exercise) or condition (e.g., a corrective bolus for when the insulin delivered is insufficient to cover an actual rise in glucose). In preferred embodiments, the system includes one or more selectable bolus constraints. The constraints can be selected by any means known in the art, such as by pushing a pre-programmed push-button or scrolling through a menu of selectable constraints with a slider or a scroll wheel.

In some embodiments, the controller module is configured (e.g., includes programming) to intelligently evaluate the internally derived data and the host's metabolic response to insulin therapy, and to adjust the bolus constraint based on that evaluation. Advantageously, a calculated insulin therapy is based on internally derived data, an engaged bolus constraint and the host's metabolic response to insulin therapy, which enables the system to optimize the insulin therapy to the host, who's metabolic response varies over time, depending upon a variety of factors, such as but not limited to changes in the host's activity level, dietary changes, medications (e.g., insulin-sensitizing agents, new insulin type), and the like. Depending upon the circumstances, the controller module can re-program a bolus constraint by adjusting the rate of insulin delivery, the amount of insulin that can be delivered and/or the time period over which the insulin can be delivered.

At block 226, in preferred embodiments, the dynamic bolus controller module is configured to evaluate the internally derived data. The internally derived data is evaluated in the context of (e.g., relative to) a selected bolus constraint and in response to selection (activation, engagement) of the bolus constraint. Returning to the example of the "Breakfast" bolus constraint, in general, the host will engage the breakfast bolus constraint (e.g., by pressing a pre-programmed button that is labeled "Breakfast") at the beginning of a breakfast meal. In general, as the host consumes his breakfast, his glucose will begin to change (e.g., rise), which the integrated system's continuous glucose sensor detects (e.g., measures, senses). Internally derived data will be generated as the system's continuous glucose sensor monitors the changes in the host's glucose level. The dynamic bolus controller module evaluates the sensor data (e.g., internally derived data) against (e.g., in the context of, relative to) the engaged breakfast constraint.

At block 228, the dynamic bolus controller module calculates a dynamic bolus medicament (e.g., insulin) therapy within the selected bolus constraint. Preferably, the dynamic bolus controller module adaptively determines a substantially optimal insulin therapy, such as for example, delivery of all or a portion (e.g., in one large dose or a plurality of smaller doses) of the maximum total insulin dose (associated with the engaged constraint) over the specified time period. For example, if the breakfast constraint is associated with a maximum of 10 U of insulin to be delivered over 30-minutes, then, when the host engages the breakfast constraint, the controller module evaluates the internally derived data and determines an insulin therapy (including instructions sent to the insulin delivery device, which automatically delivers the instructed insulin therapy). For example, in some circumstances, the calculated insulin therapy can include delivery of the entire total dose (e.g., 10 U) within the specified 30-minutes (or a shorter length of time). In other circumstances, the calculated insulin therapy can include dividing the total insulin therapy into two or more partial (e.g., smaller) doses, some or all of which can be delivered over the 30-minute period. Delivery of a partial dose depends upon the controller module's evaluation of internally derived data. For example, as the 30-minutes progress, the controller module continually (e.g., continuously, iteratively, intermittently, automatically) receives and iteratively re-evaluates internally derived data (e.g., as it becomes available) and determines, based thereon, if additional partial doses are needed to handle the rise (e.g., the actual rise) in glucose (e.g., up until the maximum dose has been delivered). In preferred embodiments, the system is configured to slow and/or stop insulin delivery in circumstances wherein the host is entering a severely hypoglycemic range (e.g., programmable, such as less than about 70 mg/dl).

In one exemplary embodiment, the dynamic bolus controller module is configured to calculate a percentage (e.g., portion, fraction) of the engaged bolus constraint (e.g., total insulin therapy) associated with a meal. For example, if the engaged bolus constraint is programmed for a total insulin dose (e.g., $D_0$) of 10 U in 1-hour, the controller module can calculate a first dose, such as about 7 U of insulin (e.g., dose $D_1$ at time $T_1$), based on the controller module's evaluation of the internally derived data relative to the engaged constraint. Instructions are sent to the integrated insulin delivery device and the partial dose is automatically delivered to the host. After an appropriate waiting period (e.g., depending upon the insulin's TAP), the controller module evaluates internally derived data (e.g., at time $T_2$, data more recent than data used to initially calculate $D_1$) and determines an additional insulin dose (e.g., dose $D_2$) required to bring the host's glucose concentration into a target range (at time $T_2$). For example, in some circumstances, an additional insulin dose may be necessary to bring the host's glucose concentration into the target range. In some other circumstances, no additional doses may be required (e.g., $D_2=0$). Suppose that, in this example, additional insulin is required, then the controller module can calculate and instruct delivery of up to 2 more units of insulin (e.g., $D_0-D_1-D_2=2$ U insulin remaining). In preferred embodiments, the insulin therapy delivered to the host is smallest total insulin dose necessary to maintain the host substantially within the target range (e.g., an euglycemic range).

In some embodiments, the system is configured for user validation of the dynamic bolus therapy, such as before delivery of the insulin (e.g., FIG. 13, box 206). In one exemplary embodiment, the system is configured to alert the host (e.g., that a dynamic bolus therapy has been calculated) and request host validation (e.g., that the host accepts the dynamic bolus therapy, such as a maximum amount of insulin to be delivered over a given period of time). Upon host validation, the calculated therapy is delivered.

In one exemplary embodiment, semi-automated integrated system 10 is configured such that the host can select a bolus constraint associated with a meal, such as by pressing one of a plurality of labeled, pre-programmed buttons or making a selection from a menu. For example, in this embodiment, each button is labeled with an icon of a food (e.g., cereal bowl, sandwich, slice of pizza, ice cream cone) and is associated with an insulin therapy calculated to be sufficient to cover that food (e.g., a meal) on average. For example, the sandwich bolus constraint is associated with an insulin dose that is generally sufficient to cover the glucose rise associated with host consumption of an average sandwich (e.g., a maximum total of up to 10 U of insulin to be delivered over 1-hour). When the host presses the sandwich button, the dynamic bolus controller module evaluates internally derived data and intelligently and adaptively determines a substantially optimal way (e.g., schedule of one or more insulin doses) to deliver a bolus insulin therapy (e.g., constrained by the sandwich constraint), preferably such that the host will not substantially enter a dangerous hypoglycemic state (e.g., glucose less than about 70 mg/dl) when the therapy is delivered. In preferred embodiments, the bolus controller module is configured to substantially continuously (e.g., constantly, automatically, iteratively, periodically, and/or intermittently) receive and evaluate internal data and to iteratively (e.g., automatically, periodically, and/or intermittently) determine an insulin therapy. For example, in some embodiments, the bolus controller module is configured to calculate a bolus therapy (e.g., based on solely the internally derived data) every about 5, 10, 15, 20, 30, 40 or 50-minutes. In some embodiments, the bolus controller module calculates a bolus therapy about every hour or longer. The calculated insulin therapy is then delivered (e.g., administered, such as automatically) to the host. In some embodiments, the insulin therapy associated with the engaged bolus constraint can be divided into portions (e.g., a total therapy of 10 U to be delivered in 1-hour is divided into two 5 U portions, five 2 U portions, or a 5 U portion, two 2 U portions and one 1 U portion) that can be delivered over time period associated with the engaged bolus constraint. In general, if portions of the total bolus therapy are delivered, the controller module is configured to wait a period of time for the delivered insulin to become active and to lower the host's blood sugar a pre-determined amount. The length of wait varies, depending upon the insulin's TAP and mode of delivery (e.g., injected subcutaneously by a pump versus by a syringe, inhaled, and the like) or the location of delivery, the type of meal being consumed, the host's insulin sensitivity and metabolic state, and the like. After the wait time, the controller module again evaluates the internally derived data and determines if additional insulin is required. For example, if the host's glucose is still increasing, another partial dose can be delivered. This cycle can be repeated until either the total bolus therapy has been delivered the delivery time has expired. In some embodiments, the system is further configured to request host validation of the therapy, such as by selection of either a YES or NO button, and the like, as is appreciated by one skilled in the art.

In some embodiments, the system is configured such that the host can manually enter a bolus insulin dose and the dynamic bolus controller module can evaluate the internally derived data and determine an insulin therapy within the entered bolus dose. For example, suppose the host wants to eat something for which there is no pre-programmed bolus constraint, such as a candy bar. In this circumstance, the host can calculate a bolus dose to cover the glucose increase that will probably occur when he eats that candy bar. He can enter the bolus dose he calculated and then have the system monitor his glucose and deliver the entered bolus dose as necessary (e.g., based upon evaluation of the internally derived data; to maintain and/or return the host within/to a target range). Preferably, the calculated therapy is substantially optimal for handling the glucose rise that will likely occur upon consumption of the meal for which the host calculated the bolus dose.

In some circumstances, a selected constraint may be insufficient to handle a meal that the host has consumed. For example, a meal can have more carbohydrates than the average meal the engaged constraint was pre-programmed to handle. Accordingly, is the controller module can be configured to alert the host to a need for additional insulin. As is understood by one in the art, a number of alerts and/or alarms can be built into the system, such as but not limited to safety alarms. The system can be configured to allow the selection of an additional meal constraint or a corrective bolus constraint and/or to allow the host to enter a manually calculated and enter a corrective bolus dose.

In preferred embodiments, the dynamic bolus controller module is configured to evaluate trend information (e.g., derived from the internally derived data; the host's metabolic response to delivered insulin) and to adapt accordingly, such as by adjusting (e.g., re-programming) the time and/or amount of an insulin therapy associated with a bolus constraint. As is understood by one skilled in the art, trend information can fluctuate over time, depending upon the host's health, activity level, medications consumed, and the like. In one exemplary embodiment, the controller module is configured to evaluate the host's insulin sensitivity over time, and to re-program a bolus constraint such that a substantially optimal insulin therapy can be delivered to the host upon engagement of the bolus constraint. For example, suppose the host is relatively insulin resistant and has a correction factor of 10:1 (e.g., 1 U of insulin will lower glucose by 10 mg/dl). Accordingly, 10 U of insulin would be required to lower the glucose level by 100 mg/dl. Suppose the host becomes more insulin sensitive, such as by increasing exercise, which would change his insulin needs. The controller module monitors these metabolic changes and adjusts calculation of the insulin therapy accordingly, such by modifying the correction factor (e.g., increase to 20:1) during insulin therapy calculation, for example. In preferred embodiments, intelligent and dynamic tracking of trends and calculation of bolus insulin therapies enables the dynamic bolus controller module to substantially minimize the risk of driving the host into a potentially dangerous state, such as but not limited to a severely hypoglycemic state (e.g., glucose concentration less than about 60 mg/dl).

In one exemplary embodiment, the controller module continually receives information (e.g., internally derived data) related to the host's glucose level and iteratively evaluates the data relative to a target glycemic range (e.g., a euglycemic range pre-set by the host, a caretaker of the host, or by the manufacturer, such as 80-120 mg/dl or 100-140 mg/dl). When the host selects a bolus constraint (e.g., 15 U to be delivered over the next hour, selected at the start of a meal), the controller module evaluates the internally derived data relative to the engaged constraint and calculates an insulin therapy that both 1) is sufficient to lower the host's glucose level to and/or within the target range and 2) is within the therapy associated with the engaged bolus constraint (e.g., will not exceed 15 U to be delivered over the next hour). If the calculated dose is less than or equal to the dose associated with the engaged constraint, the system delivers the calculated dose (e.g., a portion of the bolus dose). Generally, it will take some time for the insulin to have its effect (e.g., related to the insulin's TAP). In this embodiment, the controller module is configured to wait the appropriate period of time and then evaluate the host's response to the delivered insulin dose. In some circumstances, the host's response to the delivered insulin therapy may be insufficient (e.g., his glucose was not lowered to and/or maintained within the target range), so, the controller module will calculate and deliver an additional insulin dose (e.g., another portion of the dynamic bolus dose), based upon evaluation of the internally derived data. This iterative process continues until the time defined by the engaged bolus constraint expires (e.g., the 1-hour has passed). In some circumstances, the host's response to the initial insulin dose may be sufficient to maintain the host's blood glucose within the target range and additional insulin doses will not be calculated/delivered. While not wishing to be bound by theory, it is believed that the dynamic bolus controller module enables the use of less insulin while at the same time reducing the number of host hypoglycemic events than is possible using model-based systems or manual bolus calculation.

In one exemplary embodiment, the controller module of the system 10 is configured to continuously (e.g., continually, iteratively, intermittently, automatically, periodically) collect and/or evaluate internally derived data, including trend data, such as but not limited to the host's insulin sensitivity and metabolic profile. The controller module can be an on/off, dynamic basal and/or dynamic bolus controller module, and is configured to adaptively adjust to a newly determined metabolic profile when calculating an insulin therapy. In some embodiments, the system is configured to adjust the target range, the set point, the basal profile and/or the bolus constraint, so as to improve the accuracy of host glucose control. In some embodiments, the system (e.g., the electronics module) includes one controller module. In other embodiments, the system includes two controller modules, which are configured to work in concert with each other. For example, the system can include an on/off controller module and either the dynamic basal or dynamic bolus controller modules. In another example, the system can include the dynamic basal and dynamic bolus controller modules. In yet another embodiment, the system includes all three controller modules, which are configured to work in concert with each other.

In some embodiments, the system is configured such that the user can enter an insulin dose to be delivered. In some further embodiments, the system can be configured such that the controller module evaluates the internally derived data and calculates an appropriate and/or optimal delivery schedule for the entered dose. In some further embodiments, the system can be configured to deliver the entered dose substantially immediately.

Intelligent and Adaptive Data Evaluation and Therapy Calculation

A host's insulin requirements can fluctuate over time, due to changes in a variety of factors, such as but not limited to changes in the host's health, weight and/or exercise routine, changes in the type of insulin used and medications, dietary changes, and the like. Additionally, the condition of some components of the integrated system 10 can vary, either over time or from lot to lot. For example, many glucose sensors have some error in their function. This error can vary through out the sensor's lifetime and/or from manufacturing lot to manufacturing lot. Similarly, insulin formulations can vary between manufacturing lots, such as due to small variations in dilution or activity. In yet another example, the insulin deliver device can have some amount of error in measurement of insulin being delivered and/or remaining. Accordingly, in some embodiments, the system is configured to intelligently and adaptively adjust to changing circumstances (e.g., account for error in different system components when determining an insulin therapy), such that the host can be continuously provided with substantially optimum glucose control.

In some circumstances, one or more of the system 10 components have some amount of error. For example, in some circumstances, glucose data from a continuous glucose sensor may include some sensor error, such as about 1%, 2%, 5%, 10%, 15%, 20% or more error. In another example, in some circumstances, an insulin infusion device can have some error in measurement of the amount of insulin delivered (e.g., number of units, rate, volume, and the like) such as about 1%, 2%, 5%, 10%, 15%, 20% or more error. In yet another example, there can be small errors made when the insulin is formulated, such that it can have a slightly different activity or concentration than as labeled. Such system error can make it more difficult to control and host's glucose concentration, unless the system is configured to handle this error.

Accordingly, in some embodiments, the system 10 is configured such that the controller module (e.g., on/off, dynamic basal or dynamic bolus controller module) considers system error (e.g., sensor error, insulin activity/delivery errors) when calculating an insulin therapy (e.g., an insulin delivery rate, an insulin dose, selecting between the on and off instructions). In one exemplary embodiment, if an average sensor error is initially ±20%, then the controller module is configured to adjust the target glucose range by a similar amount up or down. Accordingly, if the original target range is 100-150 mg/dl, then the target range can be increased by 20% to about 120-180-gm/dl. This can prevent inadvertently driving the host too low (e.g., wherein the host's blood sugar is too close to a dangerous hypoglycemic level), such as by overshooting the target range (e.g., 100- to 150 mg/dl reduced by 20% would be 80- to 130 mg/dl). In another exemplary embodiment, the controller module is configured to track and/or evaluate system error (e.g., over time) and adjust one or more system parameters (e.g., target range, glucose boundary, bolus constraint, basal profile, rate if insulin delivery, time of insulin delivery and the like) such that the host is maintained substantially within the target range a substantial portion of the time the system 10 is in use (e.g., 50, 60, 70, 80, 90, or 99% of the time). For example, if sensor error increases to 30% on day-3 of use, the controller module is configured to adjust the target range a corresponding amount (e.g., increase the target range by 30%).

In some embodiments, the system 10 is includes two or all three controller modules which are configured to work in concert (e.g., switch therebetween), such that the host is maintained substantially within the target range a substantial portion of the time (e.g., 50%, 60%, 70%, 80%, 90%, 95% or more of the time) that the system is in use by the host. For example, in some embodiments, the system includes an on/off controller module and either a dynamic bolus controller module or a dynamic basal controller module. In some embodiments, the system includes both the dynamic basal and dynamic bolus controller modules, but not an on/off controller module. In some embodiments, the system includes the on/off controller module as well as both the dynamic basal and dynamic bolus controller modules.

In one exemplary embodiment, the system includes on/off and basal controller modules, and is configured such that determination of insulin therapy occurs in at least two steps. In a first step, the on/off controller module evaluates the internally derived data relative to a glucose boundary, and selects between the on and off instructions. If the on instruction is selected, the dynamic basal controller module evaluated the internally derived data relative to a programmed basal profile and calculated/determines an insulin therapy within the current time block of the basal profile. If the off instruction is selected, then insulin delivery is terminated. In a further exemplary embodiment, the system also includes a dynamic bolus controller module. In general, the on/off and basal controller modules can be configured to function automatically (e.g., perform their functions automatically and in concert with each other) until the user engages a programmable bolus constraint. When the user engages the bolus constraint, the bolus controller module calculates an insulin therapy within the engaged constraint. The system can be further configured to return to operation by the on/off and basal controller modules, until such time that the user again engages a bolus constraint. While not wishing to be bound by theory, it is believed that an intelligent, adaptive integrated system, which can switch between controller modules, can substantially improve consistency and accuracy of glucose control, which enables tight control by the host, and thereby improving the host's health and delaying diabetic complications.

In an exemplary embodiment of a fully automated integrated system 10, the system includes on/off, dynamic basal and dynamic bolus controller modules, is configured for use in conjunction with a flash insulin, and is configured to adaptively and intelligently switch (e.g., automatically, as described herein) between controller modules, depending upon evaluation of the internally derived data, system parameters (e.g., glucose boundary, target range, basal profile, bolus constraints, and the like) and system constraints, such that the host is maintained substantially at within a programmed target range at least 50% of the time the system is in use. In preferred embodiments, the host is maintained within the target range at least 60, 70, 80, 90, or 99% of the time the system is in use. More preferably, the system is further configured to maintain the host within the programmed target range regardless of the host's activity level, metabolic state and/or meal consumption. In such a system, a substantial portion of the host's day, he may experience only moderate increases/decreases in glucose. During these portions of his day, the on/off controller can select either the on or off instructions (e.g., to turn insulin delivery on and off), and when the on instruction is selected, the basal controller module can calculate delivery of basal levels of insulin. A portion of the host's day, an unexpected rapid rise in glucose concentration (e.g., the internally derived data) may occur, which may indicate that a meal is being or has been consumed. Generally, the host would require a bolus insulin therapy to handle the increased glucose that can result from meal consumption. Accordingly, the system can be configured such that the on/off controller can select the on instruction (e.g., turns on insulin delivery) and then the dynamic bolus controller module can calculate an appropriate bolus insulin therapy (e.g., within pre-programmed bolus constraints, non-host engageable). Similarly, as the glucose concentration is brought into the target range, the system can intelligently recognize a decreased requirement for insulin, and can switch from the dynamic bolus controller module, back to the dynamic basal controller module, which can calculate a basal insulin therapy (e.g., for the host's current needs). If the glucose is brought within the target range, the on/off controller can select the off instruction to terminate insulin delivery.

EXAMPLES

In one exemplary implementation of the preferred embodiments, the continuous glucose sensor (and its receiver) comprises programming to track a host during hypoglycemic or near-hypoglycemic conditions. In this implementation, the processor (e.g., controller module) includes programming that sends instructions to administer a hypoglycemic treating medicament, such as glucagon, via an implantable pump or the like, when the glucose level and rate of change surpass a predetermined threshold (for example, 80 mg/dL and 2 mg/dL/min). In this situation, the sensor waits a predetermined amount of time (for example, 40 minutes), while monitoring the glucose level, rate of change of glucose, and/or acceleration/deceleration of glucose in the host, wherein if the rate of change and/or acceleration shows a changing trend away from hypoglycemia (for example, decreased deceleration of glucose levels to non-hypoglycemia, then the host need not be alarmed. In this way, the automated glucagon delivery device can proactively preempt hypoglycemic conditions without alerting or awaking the host.

In one exemplary implementation of the preferred embodiments, a continuous glucose sensor is integrated with a continuous medicament delivery device (for example, an insulin pump) and a bolus medicament delivery device (for example, and insulin pen) and a controller module. In this embodiment, the integration exploits the benefits of automated and semi-automated device, for example, providing an automated integration with an infusion pump, while provide semi-automated integration with an insulin pen as necessary.

In one exemplary implementation of the preferred embodiments, a medicament delivery device is provided that includes reservoirs of both fast acting insulin and slow acting insulin. The medicament delivery device is integrated with a controller module as described elsewhere herein, however in this implementation, the controller module determines an amount of fast acting insulin and an amount of slow acting insulin, wherein the medicament delivery device is configured to deliver the two insulins separately and/or in combination, such that the host is maintained substantially at and/or within the target range. In this way, the receiver and medicament delivery device can work together in a feedback loop to iteratively optimize amounts of slow and fast acting insulin for a variety of situations (for example, based on glucose level, rate of change, acceleration, and behavioral factors such as diet, exercise, time of day, etc.) adapted to the individual host's metabolic profile.

In one exemplary implementation of the preferred embodiments, an integrated hypo- and hyper-glycemic treating system is provided. In this implementation, a manual-, semi-automated, or automated integration of an insulin delivery device is combined with a manual-, semi-automated, or automated integration of a glucose or glucagon delivery device. These devices are integrated with the receiver for the continuous glucose sensor and a controller module in any manner described elsewhere herein. While not wishing to be bound by theory, it is believed that the combination of a continuous glucose sensor, integrated insulin device, and integrated glucose or glucagon device provides a simplified, comprehensive, user friendly, convenient, long-term and continuous method of monitoring, treating, and optimizing comprehensive care for diabetes.

In one exemplary implementation of the preferred embodiments, an integrated hypo- and hyper-glycemic treating system is provided, including a continuous glucose sensor, an insulin infusion device and a dynamic controller module, wherein the system is configured to adaptively and intelligently evaluate the host's metabolic state (e.g., historical profile) and adjust the insulin therapy accordingly, in response to an unexpected increase in glucose above a programmed target range. In some circumstances, the boundaries between low, target and high glucose levels, between slow and fast rates of change, and between small and large insulin dose adjustments can be substantially sharp. Accordingly, in this embodiment, the dynamic controller module is configured to evaluate weighted sums (e.g., derived by processing the data collected from the continuous glucose sensor, use of a Kalman filter) to provide a suggested dynamic insulin therapy that is substantially adjusted for the host's current glucose profile (e.g., concentration, rate of change, acceleration, etc.). One skilled in the art understands that, generally, the weighting of a control action depends upon the degree to which its input condition is true. Thus, at the present time ($T_1$), the condition that best describes the glucose level and rate of change (e.g., at $T_1$) will have the largest influence on the control action (e.g., the amount of insulin to be calculated). For exemplary purposes, suppose the following conditions are defined: a very high glucose concentration is greater than 140 mg/dl; a moderately high glucose concentration is from 110 mg/dl to 140 mg/dl; a slow rise in glucose concentration is from 0.5 mg/dl/min to 1.0 mg/dl/min; and a stable glucose concentration is from −0.5-mg/di/min to 0.5 mg/di/min. Thus, if the measured glucose concentration is 140 mg/dl and it is rising at a rate of 0.5=mg/dl/min, then the host's current glucose profile falls on the boundary between very high and a little high glucose concentrations, as well as between rising slowly and stable rates. Accordingly, if a large insulin dose increase is defined as from 1-U/h to 2-U/h; a moderate dose increase as from 0.5-U/h to 1-U/h; and small dose increase as from 0.1-U/h to 0.5-U/h; then an optimal increase in insulin dose (e.g., to maintain the host in the target range) may be about 1.2-U/h, for example. Similarly, if the host is relatively insulin insensitive (e.g., resistant), a larger dose can be calculated; and if the host is relatively insulin sensitive, then a smaller dose can be calculated. Thus, the dynamic controller module is configured to adapt (e.g., adjust, modify, re-program) insulin therapy (e.g., dosing) to a given host and his current metabolic conditions. For example, the dynamic controller module can be configured to monitor (e.g., learn) the host's insulin sensitivity by comparing substantially more recent (prior minutes to hours) changes in glucose and insulin dose, and adjust the current dose boundaries accordingly. In a further example, the system can consider system error (e.g., sensor error, drug delivery error and the like) as a weighted sum, when determining the dynamic insulin therapy. For example, if the sensor error is very high and the rate of change is rising slowly, then the insulin therapy can be adjusted by a large increase; if the sensor error is very high and the rate of change is stable, then the insulin therapy can be adjusted by a medium increase; if the sensor error is a little high and the rate of change is stable, then the insulin therapy can be adjusted by a small increase. Advantageously, because any definition of boundaries between low, target and high glucose levels, between slow and fast rates of change, and between small and large insulin therapy adjustments is artificially sharp, the weighted sum provides a graded dose adjustment. Because the dynamic controller module is configured adaptively learn and track trends, the dose boundaries can be intelligently adjusted accordingly. While not wishing to be bound by theory, it is believed that due to its non-model-based nature, smooth transitions between ranges and adaptive learning, the dynamic controller module substantially increases accuracy for each host, which leads to a higher level of safety and improved host health.

In one exemplary implementation of the preferred embodiments, an integrated hypo- and hyper-glycemic treating system is provided, including a continuous glucose sensor, an insulin infusion device and a controller module (on/off, dynamic basal, dynamic bolus) configured to monitor and evaluate system error (e.g., errors in sensor readings and/or evaluation of the internally derived data) and to titrate the insulin therapy, such that the host substantially does not overshoot the euglycemic range (e.g., enter the hypoglycemic range) during delivery of the calculated dose. For example, if the sensor readings include a ±30% error, the target range is set an equivalent percent (e.g., ±30%) above the target range. For example, in some circumstances, if the preferred target range is 80-100 mg/dl, the target can be increased by 30%, to 110-140 mg/dl glucose. In other circumstances, the internally derived data can indicate that the target range should be lowered. Accordingly, the target range can be adjusted up or down, depending upon the error of the system, such that the host substantially does not enter a hypoglycemic (e.g., unsafe) glucose range.

In one exemplary implementation of the preferred embodiments, an integrated hypo- and hyper-glycemic treating system is provided, including a continuous glucose sensor, an insulin infusion device and a controller module configured to provide and/or evaluate trending information. Trend information can include changes in glucose concentration (increasing or decreasing), the rate of change, and the acceleration. Generally, consideration of trend information in insulin therapy calculation can direct relative increases and/or decreases in the calculated therapy and its delivery. For example, in a first exemplary circumstance, the host's glucose concentration is 200 mg/dl and slowly increasing; 5 U of insulin might be insufficient to bring his glucose down to the target level (e.g., 100 mg/dl). In a second exemplary circumstance, in contrast, if the host's glucose concentration is 200 mg/dl and rapidly decreasing, that same insulin dose (e.g., 5 U) might be too large and cause him to overshoot the target range (e.g., become hypoglycemic). In still another example, if the host's glucose concentration is 200 mg/dl and increasing rapidly, a larger insulin dose (e.g., 6, 7, 8, 9 or 10 U or more) may be required to bring his glucose substantially to the target range, relative to the dose required in the first exemplary circumstance. Accordingly, the controller module is configured to evaluate the trend information when calculating a medicament therapy.

In one exemplary implementation of the preferred embodiments, an integrated hypo- and hyper-glycemic treating system is provided, including a continuous glucose sensor, an insulin infusion device and a controller module, wherein the target range is a euglycemic glucose range (e.g., about 90 mg/dl to 140 mg/dl), a dynamic insulin therapy is an amount of a given insulin required to lower a hyperglycemic host's glucose concentration substantially to within about 90 mg/dl to 140 mg/dl glucose (e.g., at the time of calculation), substantially without reducing the host's glucose to a hypoglycemic range. Suppose the target range is 100-140 mg/dl, the host's current glucose concentration is 120 mg/dl and he has just consumed a meal (e.g., including an amount of carbohydrate). Generally, in response to the meal, the host's glucose will begin to rise. Preferably, the integrated system monitor's the host's glucose substantially continuously. If the host's glucose exceeds 140 mg/dl (e.g., at $T_1$), then the dynamic controller module will calculate a dynamic insulin dose (e.g., $D_1$) sufficient (at time $T_1$) to lower the host's glucose to at least 140 mg/dl. After delivery of $D_1$, the system will continue to monitor the host's glucose. Generally, a period of time sufficient for the insulin to act (e.g., depending upon the insulin's TAP) is allowed to pass. If, at a later time (e.g., $T_2$), the host's glucose exceeds 140 mg/dl, the dynamic controller module can calculate another dynamic insulin dose (e.g., $D_2$), sufficient (at time $T_2$) to lower the host's glucose to at least 140 mg/dl. If, at $T_2$, the host's glucose is within the target range, then no additional dynamic insulin doses will be calculated and/or delivered. This process can be repeated (e.g., iteratively), such that the host's glucose is maintained substantially within the target range (e.g., 100-140 mg/dl in this example). In preferred embodiments, the system is configured to stop insulin delivery and/or sound an alarm, if the host's glucose falls below the target range and/or within a dangerous range (e.g., hypoglycemic, such as less than 70 mg/dl).

In one exemplary implementation of the preferred embodiments, an integrated hypo- and hyper-glycemic treating system is provided, including a continuous glucose sensor, an insulin infusion device and a controller module, the dynamic controller module is configured to calculate an insulin therapy that, in a worst-case scenario, is not sufficient (e.g., insufficient) to drive the host into a severely hypoglycemic state (e.g., less than about 65 mg/dl). For exemplary purposes, let's suppose that the host's target glucose is 110 mg/dl, and his glucose level is currently increasing at ≥1 mg/dl/min and is projected to rise (based on the internally derived data) to 170 mg/dl. The dynamic controller module can be programmed such that at a programmed threshold level (e.g., 140 mg/dl), it calculates an insulin therapy that will be sufficient to lower the host's glucose concentration from the expected 170 mg/dl down to the target range (110 mg/dl; lowered by ~60 mg/dl). Suppose that the host's glucose actually does not rise above 140 mg/dl. In this circumstance, the 60-point correction will lower glucose to about 80 mg/dl, which is still about 20-30 mg/dl above what would be a dangerously hypoglycemic glucose concentration. On the other hand, in a best-case scenario, the dynamic controller module can anticipate and correct/prevent an expected rise in glucose concentration, such that the host is substantially maintained within a target blood glucose range, such as a euglycemic range. If the host's glucose concentration continues to rise after delivery of the insulin therapy (e.g., to 200 mg/dl), the dynamic controller module can calculate an additional insulin therapy sufficient to lower the host's glucose concentration the additional amount (e.g., 30-points). In some embodiments, the dynamic controller module is configured to divide the insulin therapy into two or more portions to be delivered over a given period of time. For example, if the insulin therapy is divided into two portions, the first portion can be delivered, and the host's response monitored. If, after the monitoring period has passed, the host's glucose concentration is still above the target, the second portion (all or a part thereof) can be delivered. If, on the other hand, the host's glucose concentration has been lowered to within a threshold (e.g., 110-140 mg/dl) or to the target range (e.g., 110 mg/dl), the second portion can be not delivered.

Methods and devices that are suitable for use in conjunction with aspects of the preferred embodiments are disclosed in U.S. Pat. Nos. 4,994,167; 4,757,022; 6,001,067; 6,741,877; 6,702,857; 6,558,321; 6,931,327; 6,862,465; 7,074,307; 7,081,195; 7,108,778; and 7,110,803.

Methods and devices that are suitable for use in conjunction with aspects of the preferred embodiments are disclosed in U.S. Patent Publication No. US-2005-0176136-A1; U.S. Patent Publication No. US-2005-0251083-A1; U.S. Patent Publication No. US-2005-0143635-A1; U.S. Patent Publication No. US-2005-0181012-A1; U.S. Patent Publication No. US-2005-0177036-A1; U.S. Patent Publication No. US-2005-0124873-A1; U.S. Patent Publication No. US-2005-0115832-A1; U.S. Patent Publication No. US-2005-0245799-A1; U.S. Patent Publication No. US-2005-0245795-A1; U.S. Patent Publication No. US-2005-0242479-A1; U.S. Patent Publication No. US-2005-0182451-A1; U.S. Patent Publication No. US-2005-0056552-A1; U.S. Patent Publication No. US-2005-0192557-A1; U.S. Patent Publication No. US-2005-0154271-A1; U.S. Patent Publication No. US-2004-0199059-A1; U.S. Patent Publication No. US-2005-0054909-A1; U.S. Patent Publication No. US-2005-0112169-A1; U.S. Patent Publication No. US-2005-0051427-A1; U.S. Patent Publication No. US-2003-0032874-A1; U.S. Patent Publication No. US-2005-0103625-A1; U.S. Patent Publication No. US-2005-0203360-A1; U.S. Patent Publication No. US-2005-0090607-A1; U.S. Patent Publication No. US-2005-0187720-A1; U.S. Patent Publication No. US-2005-0161346-A1; U.S. Patent Publication No. US-2006-0015020-A1; U.S. Patent Publication No. US-2005-0043598-A1; U.S. Patent Publication No. US-2003-0217966-A1; U.S. Patent Publication No. US-2005-0033132-A1; U.S. Patent Publication No. US-2005-0031689-A1; U.S. Patent Publication No. US-2004-0186362-A1; U.S. Patent Publication No. US-2005-0027463-A1; U.S. Patent Publication No. US-2005-0027181-A1; U.S. Patent Publication No. US-2005-0027180-A1; U.S. Patent Publication No. US-2006-0020187-A1; U.S. Patent Publication No. US-2006-0036142-A1; U.S. Patent Publication No. US-2006-0020192-A1; U.S. Patent Publication No. US-2006-0036143-A1; U.S. Patent Publication No. US-2006-0036140-A1; U.S. Patent Publication No. US-2006-0019327-A1; U.S. Patent Publication No. US-2006-0020186-A1; U.S. Patent Publication No. US-2006-0020189-A1; U.S. Patent Publication No. US-2006-0036139-A1; U.S. Patent Publication No. US-2006-0020191-A1; U.S. Patent Publication No. US-2006-0020188-A1; U.S. Patent Publication No. US-2006-0036141-A1; U.S. Patent Publication No. US-2006-0020190-A1; U.S. Patent Publication No. US-2006-0036145-A1; U.S. Patent Publication No. US-2006-0036144-A1; U.S. Patent Publication No. US-2006-0016700-A1; U.S. Patent Publication No. US-2006-0142651-A1; U.S. Patent Publication No. US-2006-0086624-A1; U.S. Patent Publication No. US-2006-0068208-A1; U.S. Patent Publication No. US-2006-0040402-A1; U.S. Patent Publication No. US-2006-0036142-A1; U.S. Patent Publication No. US-2006-0036141-A1; U.S. Patent Publication No. US-2006-0036143-A1; U.S. Patent Publication No. US-2006-0036140-A1; U.S. Patent Publication No. US-2006-0036139-A1; U.S. Patent Publication No. US-2006-0142651-A1; U.S. Patent Publication No. US-2006-0036145-A1; U.S. Patent Publication No. US-2006-0036144-A1; U.S. Patent Publication No. US-2006-0200022-A1; U.S. Patent Publication No. US-2006-0198864-A1; U.S. Patent Publication No. US-2006-0200019-A1; U.S. Patent Publication No. US-2006-0189856-A1; U.S. Patent Publication No. US-2006-0200020-A1; U.S. Patent Publication No. US-2006-0200970-A1; U.S. Patent Publication No. US-2006-0183984-A1; U.S. Patent Publication No. US-2006-0183985-A1; U.S. Patent Publication No. US-2006-0195029-A1; U.S. Patent Publication No. US-2006-0229512-A1; U.S. Patent Publication No. US-2006-0222566-A1; U.S. Patent Publication No. US-2007-0032706-A1; U.S. Patent Publication No. US-2007-0016381-A1; U.S. Patent Publication No. US-2007-0027370-A1; U.S. Patent Publication No. US-2007-0027384-A1; U.S. Patent Publication No. US-2007-0032717-A1; and U.S. Patent Publication No. US-2007-0032718-A1.

Methods and devices that are suitable for use in conjunction with aspects of the preferred embodiments are disclosed in U.S. application Ser. No. 09/447,227 filed Nov. 22, 1999 and entitled "DEVICE AND METHOD FOR DETERMINING ANALYTE LEVELS"; U.S. application Ser. No.

11/515,342 filed Sep. 1, 2006 and entitled "SYSTEMS AND METHODS FOR PROCESSING ANALYTE SENSOR DATA"; U.S. application Ser. No. 11/654,135 filed Jan. 17, 2007 and entitled "POROUS MEMBRANES FOR USE WITH IMPLANTABLE DEVICES"; U.S. application Ser. No. 11/675,063 filed Feb. 14, 2007 and entitled "ANALYTE SENSOR"; U.S. application Ser. No. 11/543,734 filed Oct. 4, 2006 and entitled "DUAL ELECTRODE SYSTEM FOR A CONTINUOUS ANALYTE SENSOR"; U.S. application Ser. No. 11/654,140 filed Jan. 17, 2007 and entitled "MEMBRANES FOR AN ANALYTE SENSOR"; U.S. application Ser. No. 11/654,327 filed Jan. 17, 2007 and entitled "MEMBRANES FOR AN ANALYTE SENSOR";U.S. application Ser. No. 11/543,396 filed Oct. 4, 2006 and entitled "ANALYTE SENSOR"; U.S. application Ser. No. 11/543,490 filed Oct. 4, 2006 and entitled "ANALYTE SENSOR"; U.S. application Ser. No. 11/543,404 filed Oct. 4, 2006 and entitled "ANALYTE SENSOR"; U.S. application Ser. No. 11/681,145 filed Mar. 1, 2007 and entitled "ANALYTE SENSOR"; and U.S. application Ser. No. 11/690,752 filed Mar. 23, 2007 and entitled "TRANSCUTANEOUS ANALYTE SENSOR".

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

What is claimed is:

1. A method for diabetes management of a host, the method comprising:
receiving sensor data generated by a continuous glucose monitoring device, wherein the sensor data is indicative of a glucose concentration; tracking and/or evaluating a system error of the continuous glucose monitoring device over time;
determining an insulin therapy instruction, using a controller module of a processor, based on the sensor data and a system error; and
delivering insulin, using an insulin infusion device, to the host based on the insulin therapy instruction from the controller module.

2. The method of claim 1, wherein the sensor data comprises a possible variation of glucose concentration based on the system error.

3. The method of claim 1, comprising monitoring an error associated with the system, whereby the system error is determined.

4. The method of claim 3, comprising iteratively evaluating the determined system error over time and adjusting one or more system parameters based on the iterative evaluation.

5. The method of claim 4, wherein the one or more system parameters are selected from the group consisting of target range, glucose boundary, bolus constraint, basal profile, rate of insulin delivery, and time of insulin delivery.

6. The method of claim 1, wherein the system error is associated with the sensor data.

7. The method of claim 1, wherein determining an insulin therapy instruction is further based on a comparison of the sensor data to a target glucose range, and wherein the target glucose range is adjusted based on the system error.

8. The method of claim 1, wherein the determining an insulin therapy instruction based on the sensor data and a system error comprises applying the system error as a weighted sum for providing a graded dose adjustment.

9. A system for diabetes management of a host, the system comprising:
a processor comprising a controller module configured to track and/or evaluate a system error of a continuous glucose monitoring device over time, and determine an insulin therapy instruction based on sensor data and the system error, wherein the sensor data is generated by a continuous analyte sensor associated with a glucose concentration of a host; and
an insulin delivery device configured to deliver insulin to the host based on the insulin therapy instruction from the processor.

10. The system of claim 9, wherein the sensor data comprises a possible variation of glucose concentration based on the system error.

11. The system of claim 9, wherein the processor is configured to monitor an error associated with the system, whereby the system error is determined.

12. The system of claim 11, wherein the processor is configured to iteratively evaluate the determined system error over time and to adjust one or more system parameters based on the iterative evaluation.

13. The system of claim 12, wherein the one or more system parameters are selected from the group consisting of target range, glucose boundary, bolus constraint, basal profile, rate of insulin delivery, and time of insulin delivery.

14. The system of claim 9, wherein the system error is associated with the sensor data.

15. The system of claim 9, wherein the controller module is configured to determine an insulin therapy instruction based on a comparison of the sensor data to a target glucose range, and wherein the target glucose range is adjusted based on the system error.

16. The system of claim 9, wherein the controller module is configured to determine an insulin therapy instruction based on the sensor data and a system error by applying the system error as a weighted sum to provide a graded dose adjustment.

17. The system of claim 9, further comprising a continuous glucose monitoring device.

18. The system of claim 9, wherein the continuous glucose monitoring device is configured to monitor an error associated with the system, whereby the system error is determined.

19. A system for diabetes management of a host, the system comprising:
- a continuous glucose monitoring device;
- a processor comprising a controller module configured to track and/or evaluate a system error of the continuous glucose monitoring device over time, and determine an insulin therapy instruction based on sensor data and the system error, wherein the sensor data is generated by the continuous analyte sensor and is associated with the glucose concentration of the host; and
- an insulin delivery device configured to deliver insulin to the host based on the insulin therapy instruction from the processor.

* * * * *

UNITED STATES PATENT AND TRADEMARK OFFICE
CERTIFICATE OF CORRECTION

| | |
|---|---|
| PATENT NO. | : 9,452,259 B2 |
| APPLICATION NO. | : 14/063941 |
| DATED | : September 27, 2016 |
| INVENTOR(S) | : Mike Dobbles |

Page 1 of 2

It is certified that error appears in the above-identified patent and that said Letters Patent is hereby corrected as shown below:

On the Title Page

Column 2 (page 2, item (56)) Line 70, Under Other Publications, change "Pancrease:" to --Pancreas:--.

Column 1 (page 3, item (56)) Line 3, Under Other Publications, change "Therpeutics" to --Therapeutics--.

In the Specification

Column 1 Line 11, Change "May 15, 2013," to --Sep. 11, 2013,--.

Column 5 Line 11, Change "as" to --at--.

Column 5 Line 14, Change "as" to --at--.

Column 14 Line 33 (Second Occurrence), Change "delivery" to --deliver--.

Column 16 Line 50, Change "and or" to --and/or--.

Column 28 Line 39, Change "and or" to --and/or--.

Column 30 Line 64, Change "by" to --be--.

Column 33 Line 26, Change "an a" to --a--.

Column 50 Line 7, Change "delivery" to --deliver--.

Signed and Sealed this
Nineteenth Day of December, 2017

Joseph Matal
*Performing the Functions and Duties of the
Under Secretary of Commerce for Intellectual Property and
Director of the United States Patent and Trademark Office*

CERTIFICATE OF CORRECTION (continued)
U.S. Pat. No. 9,452,259 B2

Column 61 Line 12, Change "di" to --dl--.

Column 61 Line 12, Change "di" to --dl--.